(12) United States Patent
Hilpert et al.

(10) Patent No.: US 9,556,117 B2
(45) Date of Patent: Jan. 31, 2017

(54) INDOLE CARBOXAMIDE DERIVATIVES AS P2X₇ RECEPTOR ANTAGONISTS

(71) Applicant: ACTELION PHARMACEUTICALS LTD, Allschwil (CH)

(72) Inventors: Kurt Hilpert, Allschwil (CH); Francis Hubler, Allschwil (CH); Dorte Renneberg, Allschwil (CH); Simon Stamm, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/653,363

(22) PCT Filed: Dec. 17, 2013

(86) PCT No.: PCT/IB2013/061029
§ 371 (c)(1),
(2) Date: Jun. 18, 2015

(87) PCT Pub. No.: WO2014/097140
PCT Pub. Date: Jun. 26, 2014

(65) Prior Publication Data
US 2015/0344425 A1    Dec. 3, 2015

(30) Foreign Application Priority Data
Dec. 18, 2012 (EP) .................... 12197880

(51) Int. Cl.
| | |
|---|---|
| *C07D 209/08* | (2006.01) |
| *C07D 209/30* | (2006.01) |
| *C07D 401/12* | (2006.01) |
| *C07D 403/12* | (2006.01) |
| *A61K 31/404* | (2006.01) |
| *A61P 29/00* | (2006.01) |
| *A61K 31/4045* | (2006.01) |
| *C07D 209/18* | (2006.01) |
| *C07D 209/24* | (2006.01) |

(52) U.S. Cl.
CPC .......... *C07D 209/08* (2013.01); *C07D 209/18* (2013.01); *C07D 209/24* (2013.01); *C07D 209/30* (2013.01); *C07D 401/12* (2013.01); *C07D 403/12* (2013.01)

(58) Field of Classification Search
CPC A61K 31/4045; A61K 31/404; C07D 209/08; C07D 209/30; C07D 209/24; C07D 401/12; C07D 209/18; C07D 403/12
See application file for complete search history.

(56) References Cited

U.S. PATENT DOCUMENTS

| | | |
|---|---|---|
| 7,407,956 B2 | 8/2008 | Dombrowski et al. |
| 2010/0137428 A1* | 6/2010 | Bozzoli ............... C07D 317/48 514/465 |
| 2011/0144153 A1* | 6/2011 | Nozawa ................ C07C 233/47 514/307 |
| 2011/0263566 A1* | 10/2011 | Matsuo ................ C07D 235/08 514/210.21 |
| 2012/0157494 A1 | 6/2012 | Harris et al. |
| 2013/0224151 A1* | 8/2013 | Pearson ................. A61K 31/00 424/85.6 |
| 2015/0322008 A1* | 11/2015 | Hilpert ................ C07D 403/12 514/210.21 |

FOREIGN PATENT DOCUMENTS

| | | |
|---|---|---|
| EP | 2243772 | 10/2010 |
| WO | WO 00/61569 | 10/2000 |
| WO | WO 01/42194 | 6/2001 |
| WO | WO 01/44170 | 6/2001 |
| WO | WO 01/94338 | 12/2001 |
| WO | WO 03/041707 | 5/2003 |
| WO | WO 03/042190 | 5/2003 |
| WO | WO 03/042191 | 5/2003 |
| WO | WO 03/080579 | 10/2003 |
| WO | WO 2004/058270 | 7/2004 |

(Continued)

OTHER PUBLICATIONS

Abberley et al,. "Identification of 2-Oxo-N-(Phenylmethyl)-4-Imidazolidinecarboxamide Antagonists Of The P2x7 Receptor" Bioorganic & Medicinal Chemistry Letters, vol. 20, (2010), p. 6370-6374.

Abdi, et al. "Discovery and Structure-Activity Relationships Of A Series Of Pyroglutamic Acid Amide Antagonists Of The P2x7 Receptor" Bioorganic & Medicinal Chemistry Letters vol. 20, (2010) p. 5080-5084.

Brown, et al. "1,3,6-Trisubstituted Indoles As Peptidoleukotriene Antagonists: Benefits Of A Second, Polar, Pyrrole Substituent", Journal Of Medicinal Chemistry, vol. 35 (13) (1992) p. 2419-2439.

Chen, et al. "Discovery of 2-Chloro-N-((4,4-Difluoro-1-Hdroxycyclohexyl)Methyl)-5-(5-Fluoropyrimidin-2-Yl)Benzamide As A Portent And Cns Penetrable P2x7 Receptor Antagonist" Bioorganic & Medicinal Chemistry Letters vol. 20, (2010), p. 3107-3111.

Chessell, et al. "Disruption Of The P2x7 Purinoceptor Gene Abolishes Chronic Inflammatory And Neuropathic Pain", Pain, vol. 114 (2005) p. 386-396.

Cho, et al,. "Gold(Iii)-Catalyzed Cyanosilylation Of Ketones And Aldehydes" Synthesis, vol. 4 (2008) p. 507-510.

(Continued)

*Primary Examiner* — Nyeemah A Grazier
*Assistant Examiner* — Amanda L Aguirre
(74) *Attorney, Agent, or Firm* — Hoxie & Associates LLC

(57) ABSTRACT

The invention relates to indole carboxamide derivatives of formula (I),

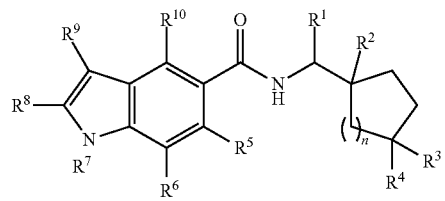

wherein $R^1$, $R^2$, $R^3$, $R^4$, $R^5$, $R^6$, $R^7$, $R^8$, $R^9$, $R^{10}$ and n are as defined in the description, their preparation and their use as pharmaceutically active compounds.

14 Claims, No Drawings

(56) References Cited

FOREIGN PATENT DOCUMENTS

| | | |
|---|---|---|
| WO | WO 2004/058731 | 7/2004 |
| WO | WO 2004/074224 | 9/2004 |
| WO | WO 2004/099146 | 11/2004 |
| WO | WO 2004/106305 | 12/2004 |
| WO | WO 2005/009968 | 2/2005 |
| WO | WO 2005/014529 | 2/2005 |
| WO | WO 2005/111003 | 11/2005 |
| WO | WO 2006/025783 | 3/2006 |
| WO | WO 2006/059945 | 6/2006 |
| WO | WO 2006/080884 | 8/2006 |
| WO | WO 2006/102610 | 9/2006 |
| WO | WO 2007/055374 | 5/2007 |
| WO | WO 2007/109154 | 9/2007 |
| WO | WO 2007/109160 | 9/2007 |
| WO | WO 2007/109172 | 9/2007 |
| WO | WO 2007/109182 | 9/2007 |
| WO | WO 2007/109192 | 9/2007 |
| WO | WO 2007/109201 | 9/2007 |
| WO | WO 2007/141267 | 12/2007 |
| WO | WO 2007/141269 | 12/2007 |
| WO | WO 2008/003697 | 1/2008 |
| WO | WO 2008/066789 | 6/2008 |
| WO | WO 2008/112205 | 9/2008 |
| WO | WO 2008/114002 | 9/2008 |
| WO | WO 2008/116814 | 10/2008 |
| WO | WO 2008/116845 | 10/2008 |
| WO | WO 2008/119685 | 10/2008 |
| WO | WO 2008/119825 | 10/2008 |
| WO | WO 2008/124153 | 10/2008 |
| WO | WO 2008/125600 | 10/2008 |
| WO | WO 2008/138876 | 11/2008 |
| WO | WO 2009/012482 | 1/2009 |
| WO | WO 2009/023623 | 2/2009 |
| WO | WO 2009/070116 | 6/2009 |
| WO | WO 2009/074518 | 6/2009 |
| WO | WO 2009/074519 | 6/2009 |
| WO | WO 2009/077362 | 6/2009 |
| WO | WO 2009/077559 | 6/2009 |
| WO | WO 2009/108551 | 9/2009 |
| WO | WO 2009/118175 | 10/2009 |
| WO | WO 2009/132000 | 10/2009 |
| WO | WO 2010/118921 | 10/2010 |
| WO | WO 2011/054947 | 5/2011 |
| WO | WO 2012/114268 | 8/2012 |
| WO | WO 2012/163792 | 12/2012 |
| WO | WO 2013/014587 | 1/2013 |
| WO | WO 2013/108227 | 7/2013 |
| WO | WO 2014/057078 | 4/2014 |
| WO | WO 2014/057080 | 4/2014 |
| WO | WO 2014/091415 | 6/2014 |
| WO | WO 2014/115072 | 7/2014 |
| WO | WO 2014/115078 | 7/2014 |

OTHER PUBLICATIONS

Degraffenreid, et al. "An Efficient And Scalable One-Pot Double Michael Addition-Dieckmann Condensation For The Synthesis of 4,4-Disubstituted Cyclohexane B-Keto Esters", Journal of Organic Chemistry, vol. 72 (19) (2007) p. 7455-7458.

Deuchars, et al. "Neuronal P2x7 Receptors Are Targeted To Presynaptic Terminals In The Central And Peripheral Nervous Systems" The Journal Of Neuroscience, vol. 21 (18) (2001), p. 7143-7152.

Duplantier, et al. "Optimization Of The Physicochemical And Pharmacokinetic Attributes In A 6-Azauracil Series Of P2x7 Receptor Antagonists Leading To The Discovery Of The Clinical Candidate Ce-224,535", Bioorganic & Medicinal Chemistry Letters, vol. 21 (2011), p. 3708-3711.

Ferrari, et al. "Atp-Mediated Cytotoxicity In Microglial Cells" Neuropharmacology, vol. 36 (9), (1997), p. 1295-1301.

Furber, et al. "Discovery Of Potent and Selective Adamantane-Based Small-Molecule P2x7 Receptor Antagonistss/Interleukin-1β Inhibitors", Journal Of Medicinal Chemistry, vol. 50 (2007), p. 5882-5885.

Goldstein, et al., "Sur L'aeide 4,5-Dinitro-2-Ehloro-Benzolque Par Henri Goldstein Et Andre Studer", Helv. Cim. Acta, vol. 20 (1937), p. 1407-1412.

Gould et al., "Salt selection for basic drugs" International Journal of Pharmaceutics, vol. 33 (1986), p. 201-217.

Greene, et al. "Protective Groups In Organic Synthesis" Wiley Interscience (1999).

Guile, et al. "Antagonists Of The P2x7 Receptor. From Lead Identification To Drug Development", Journal Of Medicinal Chemistry, vol. 52 (10), (2009), p. 3123-3141.

International Search Report of International Application No. PCT/IB2013/061029, mailed Mar. 18, 2014, 4 pages.

Ito, et al. "Cyanation of acetals with t-butyl isocyanide-tic14 system" The Chemical Society of Japan, (1984), p. 937-940.

J.S. Wiley, et al. "Transduction mechanisms of p2z purinoceptors" Ciba Foundation Symposia, vol. 198, (1996), p. 149-160 and 160-165.

Jacobs, et al. "Synthesis, Structure-Activity Relationships, And Pharmacological Evaluation Of A Series Of Luorinated 3-Benzyl-5-Indolecarboxamides: Identification Of 4[[5-[((2r)-2-Methyl-4,4,4-Trifluorobutyl)Carbamoyl]-1-Methylindo1-3-Y1]Methyl]-3-Methoxy-N-[(2-Methylphenyl)Sulfonyl]Benzamide, A Potent, Orally Active Antagonist Of Leukotrienes D4 and E4", Journal Of Medicinal Chemistry, vol. 37 (1994), p. 1282-1297.

Kitamura, et al. "Powerful chiral phase-transfer catalysts for the asymmetric synthesis of α-alkyl- and α,α-dialkyl-α-amino acids", Angewandte Chemie. Int. ed, vol. 44, (2005), p. 1549-1551.

Letavic, et al. "Synthesis And Pharmacological Characterization Of Two Novel, Brain Penetrating P2x7 Antagonists", American Chemical Society Medicinal Chemistry Letters, vol. 4, (2013), p. 419-422.

North, et al., "Molecular physiology of p2x receptors", Physiology Review, vol. 82 (2002), p. 1013-1067.

Parmee, et al. "4-Amino cyclohexylglycine analogues as potnt dipeptidyl peptidase iv inhibitors" Bioorganic & Medicinal Chemistry Letters, vol. 14, (2004), p. 43-46.

Remington, The science and practice of pharmacy, 21st edition (2005).

Solle, et al. "Mechanisms of signal transduction: altered cytokine production in mice lacking p2x7 receptors", The Journal of Biological Chemistry, vol. 276(1) (2001), p. 125-132.

Sperlagh, et al. "Involvement of p2x7 receptors in the regulation of neurotransmitter release in the rat hippocampus", Journal of Neurochemistry, vol. 81 (2002), p. 1196-1211.

Subramanyam, et al. "Discovery, synthesis and sar of azinyl- and azolylbenzamides antagonists of the p2x7 receptor", bioorganic & Medicinal Chemistry Letters, vol. 21 (2011) pp. 5475-5479.

Surprenant, et al. "The cytolytic p2z receptor for extracellular atp identified as a p2x receptor (p2x7)" science, vol. 272 (1996), p. 735-738.

Velcicky, et al. "Palladium-Catalyzed Cyanomethylation Of Aryl Halides Through Domino Suzuki Coupling-Isoxazole Fragmentation" Journal Of The American Chemical Society vol. 133, (2011), p. 6948-6951.

Virginio, et al. "Kinetics Of Cell Lysis, Dye Uptake And Permeability Changes In Cells Expressing The Rat P2x7 Receptor", Journal Of Physiology, vol. 519 (2), (1999), p. 335-346.

Wang, et al. "Palladium-Catalyzed One-Pot Synthesis of 2-Alkyl-2-Arylcyanoacetates" Journal Organic Chemistry, vol. 73 (4), (2008), p. 1643-1645.

Yu, et al. "Cellular Localization Of P2x7 Receptor Mrna In The Rat Brain" Brain Research, vol. 1194, (2008), p. 45-55.

\* cited by examiner

INDOLE CARBOXAMIDE DERIVATIVES AS P2X₇ RECEPTOR ANTAGONISTS

CROSS REFERENCE TO RELATED APPLICATIONS

This application is a U.S. National Phase Application filed under 35 U.S.C. 371 of International Application No. PCT/IB2013/061029 filed Dec. 17, 2013, which claims priority to European Application No. 12197880.3 filed Dec. 18, 2012.

The present invention relates to indole carboxamide derivatives of formula (I) and their use as pharmaceuticals. The invention also concerns related aspects including processes for the preparation of the compounds, pharmaceutical compositions containing one or more compounds of formula (I), and especially their use as $P2X_7$ receptor antagonists.

The $P2X_7$ receptors (P2RX7) belong to the family of P2X ionotropic receptors that are activated by extracellular nucleotides, in particular adenosine triphosphate (ATP). P2RX7 is distinguished from other P2X family members by the high concentrations (mM range) of ATP required to activate it and its ability to form a large pore upon prolonged or repeated stimulation (North, R. A., Physiol. Rev. 2002, 82(4), 1013-67; Surprenant, A., Rassendren, F. et al., Science 1996, 272(5262), 735-8; Virginio, C., MacKenzie, A. et al., J. Physiol., 1999, 519, 335-46). P2RX7 is present on many cell types, especially ones known to be involved in inflammatory and immune processes. This is reflected within both the periphery and the CNS as Lipopolysaccharide S (LPS) priming of monocytes and microglia followed by ATP stimulation has been shown to lead to the local release and processing of IL1β and other family members including IL18 through a P2RX7 mediated mechanism. Indeed mice lacking the P2X7 receptor are unable to release IL1β following LPS priming and ATP stimulation providing further evidence of its role in this pathway (Solle, M., Labasi, J. et al., J. Biol. Chem., 2001, 276(1), 125-32). In addition L-selectin shedding from monocytes, macrophages and lymphocytes, degranulation in mast cells and apoptosis in lymphocytes are all associated with P2RX7 stimulation. P2RX7 is also expressed on epithelial and endothelial cells (Ferrari, D., Chiozzi, P. et al., Neuropharmacology 1997, 36(9), 1295-301; Wiley, J. S., Chen, J. R. et al., Ciba Found Symp. 1996, 198, 149-60 and 160-5; North, R. A., Physiol. Rev. 2002, 82(4), 1013-67). In addition to its role in the periphery it may have an important function in neurotransmission within the CNS through its activation on postsynaptic and/or presynaptic central and peripheral neurons and glia (Deuchars, S. A., Atkinson, L. et al., J. Neurosci. 2001, 21(18), 7143-52; Sperlagh, B., Kofalvi, A. et al., J. Neurochem. 2002, 81(6), 1196-211). Recent data that has emerged using in situ hybridization demonstrated that P2X7 receptor mRNA was widely distributed throughout the rat brain. Specifically, among the areas of high P2X7mRNA expression noted were the piriform cortex, hippocampus, pontine nuclei and the anterior horn of the spinal cord (Yu, Y., Ugawa, S. et al., Brain. Res. 2008, 1194, 45-55). Hence there is therapeutic rationale for the use of P2X7 ion channel blockers in the treatment of a variety of disease states. These include but are not limited to diseases associated with the central nervous system such as stroke or injury and diseases associated with neuro-degeneration and neuroinflammation such as Alzheimer's disease, Huntington's disease, epilepsy, Amyotrophic lateral sclerosis, acute spinal cord injury additionally to meningitis, sleep disorders, mood and anxiety disorders as well as chronic and neuropathic and inflammatory pain. Furthermore, peripheral inflammatory disorders and autoimmune diseases including but not limited to rheumatoid arthritis, osteoarthritis, psoriasis, allergic dermatitis, asthma, chronic obstructive pulmonary disease, airways hyper-responsiveness, septic shock, bronchitis, glomerulonephritis, irritable bowel disease, skin injury, lung emphysema, Limb girdle dystrophy type 2B, fibrosis, Syndrome of synovitis Acne Pustulosis, atherosclerosis, burn injury, spinal cord injury, Hyperostosis Osteitis, Crohn's disease, ulcerative colitis, growth and metastases of malignant cells, myoblastic leukaemia, diabetes, trauma, meningitis, osteoporosis, burn injury, ischemic heart disease, and varicose veins and trauma, are all examples where the involvement of P2X7 channels has been implicated. In addition a recent report suggests a link between P2RX7 and chronic, inflammatory and neuropathic pain (Chessell, I. P., Hatcher, J. P. et al., Pain, 2005, 114(3), 386-96). Overall, these findings indicate a role for the P2X7 receptor in the process of neuronal synaptic transmission and therefore a potential role for P2X7 antagonists as novel therapeutic tools to treat neuropathic pain.

In view of the above observations, there is significant requirement for P2X7 antagonists that can be efficiently used in treating neuropathic pain, chronic inflammatory pain, inflammation, and neurodegenerative conditions.

Different indole carboxamide derivatives, which are also $P2X_7$ receptor antagonists, have been disclosed in WO 2009/023623, WO 2009/108551 and WO 2009/118175.

1) The present invention relates to indole carboxamide derivatives of formula (I),

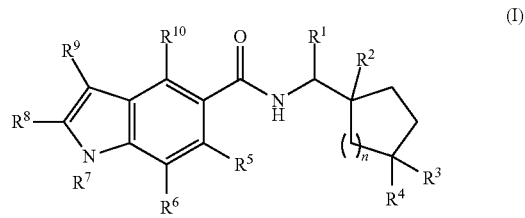

wherein n represents 1, 2, 3 or 4;

$R^1$ represents hydrogen and $R^2$ represents hydroxy; hydroxy-$(C_1$-$C_3)$alkyl; $(C_1$-$C_3)$alkoxy; —$NHR^{11}$; —$N(CH_3)_2$; —CN; —$CONH_2$; $(C_1$-$C_4)$alkoxy-carbonyl; $(C_1$-$C_4)$alkylamino-carbonyl; aryl which is unsubstituted or mono- or di-substituted with $(C_1$-$C_3)$fluoroalkyl or halogen; or heteroaryl which is unsubstituted or mono- or di-substituted with $(C_1$-$C_4)$alkyl, $(C_1$-$C_3)$fluoroalkyl or halogen; or $R^1$ represents $(C_1$-$C_3)$alkyl or hydroxy-$(C_1$-$C_3)$alkyl and $R^2$ represents hydrogen;

$R^3$ represents hydrogen or fluoro;

$R^4$ represents hydrogen or fluoro;

$R^5$ represents hydrogen, $(C_1$-$C_4)$alkyl or halogen;

$R^6$ represents hydrogen, $(C_1$-$C_4)$alkyl, $(C_1$-$C_4)$alkoxy, $(C_1$-$C_4)$alkyl-carbonyl, hydroxy-$(C_1$-$C_4)$alkyl, hydroxy-$(C_2$-$C_4)$alkoxy, $(C_1$-$C_2)$alkoxy-$(C_1$-$C_4)$alkyl, $(C_1$-$C_4)$alkoxy-$(C_2$-$C_4)$alkoxy, hydroxy, amino, nitro or halogen;

$R^7$ represents hydrogen or $(C_1$-$C_3)$alkyl;

$R^8$ represents hydrogen, $(C_1$-$C_4)$alkyl or hydroxy;

$R^9$ represents hydrogen, $(C_1$-$C_4)$alkyl, $(C_1$-$C_4)$alkylthio, formyl or halogen;

$R^{10}$ represents fluoro, chloro, methyl, ethyl, $(C_1$-$C_2)$fluoroalkyl or methoxy; and $R^{11}$ represents hydrogen, benzyl, $(C_1-C_4)$alkyl-carbonyl, $(C_1-C_4)$alkoxy-carbonyl or $(C_1-C_4)$alkyl-sulfonyl which is unsubstituted or mono-substituted with hydroxy or $(C_1-C_4)$alkoxy-carbonyl;

and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

Definitions provided herein are intended to apply uniformly to the compounds of formulae (I), $(I_{St1})$, $(I_{HET})$ and $(I_{OH})$ as defined in any one of embodiments 1) to 42), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "alkyl", used alone or in combination, refers to a straight or branched chain alkyl group containing one to four carbon atoms. The term "$(C_x-C_y)$alkyl" (x and y each being an integer), refers to an alkyl group as defined before containing x to y carbon atoms. For example a $(C_1-C_4)$alkyl group contains from one to four carbon atoms. Representative examples of alkyl groups include methyl, ethyl, n-propyl, iso-propyl, n-butyl, iso-butyl, sec.-butyl and tert.-butyl.

In case "$R^1$" represents "$(C_1-C_3)$alkyl" the term means $(C_1-C_3)$alkyl groups as defined above. Examples of said groups are methyl, ethyl, n-propyl and iso-propyl. Preferred is methyl.

In case "$R^5$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec.-butyl and tert.-butyl. Preferred is methyl.

In case "$R^6$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec.-butyl and tert.-butyl and notably methyl, ethyl, n-propyl and iso-butyl. Preferred are methyl and iso-butyl.

In case "$R^7$" represents "$(C_1-C_3)$alkyl" the term means $(C_1-C_3)$alkyl groups as defined above. Examples of said groups are methyl, ethyl, n-propyl and iso-propyl. Preferred is methyl.

In case "$R^8$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec.-butyl and tert.-butyl. Preferred is methyl.

In case "$R^9$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec.-butyl and tert.-butyl. Preferred is methyl.

In case a $(C_1-C_4)$alkyl group is a substituent to a heteroaryl group, the term "$(C_1-C_4)$alkyl" means $(C_1-C_4)$alkyl groups as defined above. Examples of said groups are methyl, ethyl, n-propyl, iso-propyl, n-butyl, iso-butyl, sec.-butyl and tert.-butyl. Preferred is methyl.

The term "alkoxy", used alone or in combination, refers to an alkyl-O— group wherein the alkyl group is as defined above. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec.-butoxy and tert.-butoxy.

In case "$R^2$" represents "$(C_1-C_3)$alkoxy" the term means $(C_1-C_3)$alkoxy groups as defined above. Examples of said groups are methoxy, ethoxy, n-propoxy and iso-propoxy. Preferred is methoxy.

In case "$R^6$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec.-butoxy and tert.-butoxy and notably methoxy and ethoxy. Preferred is methoxy.

The term "hydroxy-$(C_1-C_4)$alkyl", used alone or in combination, refers to an alkyl group as defined before containing from one to four carbon atoms in which one hydrogen atom has been replaced with hydroxy. Examples of said groups are hydroxy-methyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl, 2-hydroxy-prop-2-yl, 1-hydroxy-but-1-yl, 2-hydroxy-but-1-yl, 3-hydroxy-but-1-yl, 4-hydroxy-but-1-yl, 1-hydroxy-but-2-yl, 2-hydroxy-but-2-yl, 3-hydroxy-but-2-yl, 4-hydroxy-but-2-yl, 1-hydroxy-2-methyl-prop-1-yl, 2-hydroxy-2-methyl-prop-1-yl, 3-hydroxy-2-methyl-prop-1-yl, and 2-hydroxy-1,1-dimethyl-eth-1-yl. In analogy, the term "hydroxy-$(C_1-C_3)$alkyl", used alone or in combination, refers to an alkyl group as defined before containing one to three carbon atoms in which one hydrogen atom has been replaced with hydroxy. Examples of said groups are hydroxy-methyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl and 2-hydroxy-prop-2-yl.

In case "$R^1$" represents "hydroxy-$(C_1-C_3)$alkyl" the term means hydroxy-$(C_1-C_3)$alkyl groups as defined above. Representative examples of said groups are hydroxy-methyl, 2-hydroxy-ethyl and 3-hydroxy-prop-1-yl. Preferred is hydroxy-methyl.

In case "$R^2$" represents "hydroxy-$(C_1-C_3)$alkyl" the term means hydroxy-$(C_1-C_3)$alkyl groups as defined above. Representative examples of said groups are hydroxy-methyl, 2-hydroxy-ethyl and 3-hydroxy-prop-1-yl. Preferred is hydroxy-methyl.

In case "$R^6$" represents "hydroxy-$(C_1-C_4)$alkyl" the term means hydroxy-$(C_1-C_4)$alkyl groups as defined above. Examples of said groups are hydroxy-methyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl, 2-hydroxy-prop-2-yl, 1-hydroxy-but-1-yl, 2-hydroxy-but-1-yl, 3-hydroxy-but-1-yl, 4-hydroxy-but-1-yl, 1-hydroxy-but-2-yl, 2-hydroxy-but-2-yl, 3-hydroxy-but-2-yl, 4-hydroxy-but-2-yl, 1-hydroxy-2-methyl-prop-1-yl, 2-hydroxy-2-methyl-prop-1-yl, 3-hydroxy-2-methyl-prop-1-yl, and 2-hydroxy-1,1-dimethyl-eth-1-yl. Preferred are 1-hydroxy-ethyl and 2-hydroxy-prop-2-yl.

The term "hydroxy-$(C_2-C_4)$alkoxy", used alone or in combination, refers to an alkoxy group as defined before containing from two to four carbon atoms in which one hydrogen atom has been replaced with hydroxy. Examples of said groups are 2-hydroxy-ethoxy, 2-hydroxy-prop-1-yloxy, 3-hydroxy-prop-1-yloxy, 1-hydroxy-prop-2-yloxy, 2-hydroxy-but-1-yloxy, 3-hydroxy-but-1-yloxy, 4-hydroxy-but-1-yloxy, 1-hydroxy-but-2-yloxy, 3-hydroxy-but-2-yloxy, 4-hydroxy-but-2-yloxy, 2-hydroxy-2-methyl-prop-1- yloxy, 3-hydroxy-2-methyl-prop-1-yloxy, and 2-hydroxy-1,1-dimethyl-eth-1-yloxy. Preferred is 2-hydroxy-ethoxy.

The term "$(C_1-C_2)$alkoxy-$(C_1-C_4)$alkyl", used alone or in combination, refers to an alkyl group as defined before containing from one to four carbon atoms in which one hydrogen atom has been replaced with $(C_1-C_2)$alkoxy as defined before. Examples of said groups are methoxy-methyl, methoxy-ethyl, methoxy-propyl, methoxy-butyl, ethoxy-methyl, ethoxy-ethyl, ethoxy-propyl and ethoxy-butyl.

In case "$R^6$" represents "$(C_1-C_2)$alkoxy-$(C_1-C_4)$alkyl" the term means "$(C_1-C_2)$alkoxy-$(C_1-C_4)$alkyl groups as defined above. Representative examples of said groups are methoxy-methyl, 2-methoxy-ethyl, 3-methoxy-prop-1-yl, 4-methoxy-but-1-yl, ethoxy-methyl, 2-ethoxy-ethyl, 3-ethoxy-prop-1-yl and 4-ethoxy-but-1-yl. Preferred is 3-methoxy-prop-1-yl. In another embodiment preferred $(C_1-C_2)$alkoxy-$(C_1-C_4)$alkyl groups representing $R^6$ are 2-ethoxy-ethyl, 2-methoxy-prop-2-yl and 3-methoxy-prop-1-yl.

The term "$(C_1-C_4)$alkoxy-$(C_2-C_4)$alkoxy", used alone or in combination, refers to an alkoxy group as defined before containing from two to four carbon atoms in which one hydrogen atom has been replaced with $(C_1-C_4)$alkoxy as defined before. A preferred example of said groups is 2-tert-butoxy-ethoxy.

The term "alkylthio", used alone or in combination, refers to an alkyl-S— group wherein the alkyl group is as defined above. The term "$(C_x-C_y)$alkylthio" (x and y each being an integer) refers to an alkylthio group as defined before containing x to y carbon atoms. For example a $(C_1-C_4)$ alkylthio group contains from one to four carbon atoms. Examples of alkylthio groups include methylthio, ethylthio, n-propylthio, iso-propylthio, n-butylthio, iso-butylthio, sec.-butylthio and tert.-butylthio.

In case "$R^9$" represents "$(C_1-C_4)$alkylthio" the term means $(C_1-C_4)$alkylthio groups as defined above. Examples of said groups are methylthio, ethylthio, n-propylthio, iso-propyl-thio, n-butylthio, iso-butylthio, sec.-butylthio and tert.-butylthio. Preferred is methylthio. The term "alkyl-sulfonyl", used alone or in combination, refers to an alkyl-$S(O)_2$— group wherein the alkyl group is as defined above, which is attached to the rest of the molecule via the sulfonyl-S-atom. The term "$(C_x-C_y)$alkyl-sulfonyl" (x and y each being an integer) refers to an alkyl-sulfonyl group as defined before containing x to y carbon atoms. For example a $(C_1-C_4)$alkyl-sulfonyl group contains from one to four carbon atoms. Examples of alkyl-sulfonyl groups include methyl-sulfonyl, ethyl-sulfonyl, n-propyl-sulfonyl, iso-propyl-sulfonyl, n-butyl-sulfonyl, iso-butyl-sulfonyl, sec.-butyl-sulfonyl and tert.-butyl-sulfonyl.

In case "$R^{11}$" represents "$(C_1-C_4)$alkyl-sulfonyl" the term means $(C_1-C_4)$alkyl-sulfonyl groups as defined above. Examples of said groups are methyl-sulfonyl, ethyl-sulfonyl, n-propyl-sulfonyl, iso-propyl-sulfonyl, n-butyl-sulfonyl, iso-butyl-sulfonyl, sec.-butyl-sulfonyl and tert.-butyl-sulfonyl. Preferred are methyl-sulfonyl and ethyl-sulfonyl.

The term "alkyl-carbonyl", used alone or in combination, refers to an alkyl-C(O)— group wherein the alkyl group is as defined before, which is attached to the rest of the molecule via the carbonyl-C-atom. The term "$(C_x-C_y)$alkyl-carbonyl" (x and y each being an integer) refers to an alkyl-carbonyl group as defined before containing in the alkyl radical x to y carbon atoms. For example a $(C_1-C_4)$ alkyl-carbonyl group contains in the alkyl radical one to four carbon atoms. Examples of alkyl-carbonyl groups include methyl-carbonyl, ethyl-carbonyl, n-propyl-carbonyl, iso-propyl-carbonyl, n-butyl-carbonyl, iso-butyl-carbonyl, sec.-butyl-carbonyl and tert.-butyl-carbonyl.

In case "$R^6$" represents "$(C_1-C_4)$alkyl-carbonyl" the term means $(C_1-C_4)$alkyl-carbonyl groups as defined above. Examples of said groups are methyl-carbonyl, ethyl-carbonyl, n-propyl-carbonyl, iso-propyl-carbonyl, n-butyl-carbonyl, iso-butyl-carbonyl, sec.-butyl-carbonyl and tert.-butyl-carbonyl. Preferred is methyl-carbonyl.

In case "$R^{11}$" represents "$(C_1-C_4)$alkyl-carbonyl" the term means $(C_1-C_4)$alkyl-carbonyl groups as defined above. Examples of said groups are methyl-carbonyl, ethyl-carbonyl, n-propyl-carbonyl, iso-propyl-carbonyl, n-butyl-carbonyl, iso-butyl-carbonyl, sec.-butyl-carbonyl and tert.-butyl-carbonyl. Preferred is methyl-carbonyl.

The term "alkoxy-carbonyl", used alone or in combination, refers to an alkoxy-C(O)— group wherein the alkoxy group is as defined before, which is attached to the rest of the molecule via the carbonyl-C-atom. The term "$(C_x-C_y)$ alkoxy-carbonyl" (x and y each being an integer) refers to an alkoxy-carbonyl group as defined before containing in the alkoxy radical x to y carbon atoms. For example a $(C_1-C_4)$ alkoxy-carbonyl group contains in the alkoxy radical one to four carbon atoms. Examples of alkoxy-carbonyl groups include methoxy-carbonyl, ethoxy-carbonyl, n-propoxy-carbonyl, iso-propoxy-carbonyl, n-butoxy-carbonyl, iso-butoxy-carbonyl, sec.-butoxy-carbonyl and tert.-butoxy-carbonyl.

In case "$R^2$" represents "$(C_1-C_4)$alkoxy-carbonyl" the term means $(C_1-C_4)$alkoxy-carbonyl groups as defined above. Examples of said groups are methoxy-carbonyl, ethoxy-carbonyl, n-propoxy-carbonyl, iso-propoxy-carbonyl, n-butoxy-carbonyl, iso-butoxy-carbonyl, sec.-butoxy-carbonyl and tert.-butoxy-carbonyl. Preferred is methoxy-carbonyl.

In case "$R^{11}$"represents "$(C_1-C_4)$alkoxy-carbonyl" the term means $(C_1-C_4)$alkoxy-carbonyl groups as defined above. Examples of said groups are methoxy-carbonyl, ethoxy-carbonyl, n-propoxy-carbonyl, iso-propoxy-carbonyl, n-butoxy-carbonyl, iso-butoxy-carbonyl, sec.-butoxy-carbonyl and tert.-butoxy-carbonyl. Preferred is tert.-butoxy-carbonyl.

In case a $(C_1-C_4)$alkoxy-carbonyl group is a substituent to a $(C_1-C_4)$alkyl-sulfonyl group representing $R^{11}$, the term "$(C_1-C_4)$alkoxy-carbonyl" means $(C_1-C_4)$alkoxy-carbonyl groups as defined above. Examples of said groups are methoxy-carbonyl, ethoxy-carbonyl, n-propoxy-carbonyl, iso-propoxy-carbonyl, n-butoxy-carbonyl, iso-butoxy-carbonyl, sec.-butoxy-carbonyl and tert.-butoxy-carbonyl. Preferred is methoxy-carbonyl.

The term "alkylamino-carbonyl", used alone or in combination, refers to an alkyl-NH—C(O)— group wherein the alkyl group is as defined before, which is attached to the rest of the molecule via the —NH—C(O)— group. The term "$(C_x-C_y)$alkylamino-carbonyl" (x and y each being an integer) refers to an alkylamino-carbonyl group as defined before containing in the alkyl radical x to y carbon atoms. For example a $(C_1-C_4)$alkylamino-carbonyl group contains in the alkyl radical one to four carbon atoms. Examples of alkylamino-carbonyl groups include methylamino-carbonyl, ethylamino-carbonyl, n-propylamino-carbonyl, iso-propylamino-carbonyl, n-butylamino-carbonyl, iso-butylamino-carbonyl, sec.-butylamino-carbonyl and tert.-butylamino-carbonyl.

In case "$R^2$" represents "$(C_1-C_4)$alkylamino-carbonyl" the term means $(C_1-C_4)$alkylamino-carbonyl groups as defined above. Examples of said groups are methylamino-carbonyl, ethylamino-carbonyl, n-propylamino-carbonyl, iso-propylamino-carbonyl, n-butylamino-carbonyl, iso-butylamino-carbonyl, sec.-butylamino-carbonyl and tert.-butylamino-carbonyl. Preferred is methylamino-carbonyl.

The term "$(C_x\text{-}C_y)$fluoroalkyl" (x and y each being an integer) refers to an alkyl group as defined before containing x to y carbon atoms in which one or more (and possibly all) hydrogen atoms have been replaced with fluoro. For example a $(C_1\text{-}C_3)$fluoroalkyl group contains from one to three carbon atoms in which one to seven hydrogen atoms have been replaced with fluoro. In case "$R^{10}$" represents "$(C_1\text{-}C_2)$fluoroalkyl" the term means $(C_1\text{-}C_2)$fluoroalkyl groups as defined above. Representative examples of said groups are difluoromethyl, trifluoromethyl, 2,2-difluoroethyl and 2,2,2-trifluoroethyl. Preferred is trifluoromethyl.

In case "$(C_1\text{-}C_3)$fluoroalkyl" is a substituent to an aryl or a heteroaryl group, the term "$(C_1\text{-}C_3)$fluoroalkyl" means $(C_1\text{-}C_3)$fluoroalkyl groups as defined above. Representative examples of said groups are difluoromethyl, trifluoromethyl, 2,2-difluoroethyl and 2,2,2-trifluoroethyl. Preferred is trifluoromethyl.

The term halogen means fluoro, chloro, bromo or iodo.

In case "$R^5$" represents "halogen" the term means fluoro, chloro, bromo or iodo. Preferred is chloro.

In case "$R^6$" represents "halogen" the term means fluoro, chloro, bromo or iodo. Preferred is iodo. In another embodiment chloro is preferred.

In case "$R^9$" represents "halogen" the term means fluoro, chloro, bromo or iodo. Preferred is fluoro.

In case "halogen" is a substituent to an aryl or a heteroaryl group, the term "halogen" means fluoro, chloro, bromo or iodo. Preferred is chloro.

The term "aryl", used alone or in any combination, means a phenyl or a naphthyl group. Preferred is a phenyl group. The aryl group is unsubstituted or substituted as explicitly defined. Examples are 4-chloro-phenyl and 4-trifluoromethyl-phenyl.

The term "heteroaryl", used alone or in combination, means a 5- to 10-membered monocyclic or bicyclic aromatic ring containing 1, 2 or 3 heteroatoms independently selected from oxygen, nitrogen and sulfur. Preferred is a 5- or 6-membered monocyclic heteroaryl group. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, cinnolinyl, quinazolinyl, quinoxalinyl and phthalazinyl. Preferred are pyridyl and pyrimidyl. The heteroaryl groups are unsubstituted or substituted as explicitly defined. Examples of such unsubstituted or substituted heteroaryl groups are pyridyl (notably pyridin-3-yl), 2-chloro-pyridyl (notably 2-chloro-pyridin-5-yl), 2-trifluoromethyl-pyridyl (notably 2-trifluoromethyl-pyridyl (notably 2-trifluoromethyl-pyridin-5-yl), 2-methyl-pyrimidyl (notably 2-methyl-pyrimidin-5-yl) and 2-trifluoromethyl-pyrimidyl (notably 2-trifluoromethyl-pyrimidin-5-yl).

The term "5- or 6-membered monocyclic heteroaryl group", used alone or in combination, means a 5- or 6-membered monocyclic aromatic ring containing one nitrogen atom and optionally one additional heteroatom selected from oxygen, nitrogen and sulfur. Preferred are 6-membered monocyclic aromatic rings containing one or two nitrogen atoms. Examples of such heteroaryl groups are oxazolyl, isoxazolyl, thiazolyl, isothiazolyl, pyrrolyl, imidazolyl, pyrazolyl, pyridyl, pyrimidyl, pyridazinyl and pyrazinyl. Preferred are pyridyl and pyrimidyl. The heteroaryl groups are unsubstituted or substituted as explicitly defined. Examples of such unsubstituted or substituted 5- or 6-membered monocyclic heteroaryl groups are pyridyl (notably pyridin-3-yl), 2-chloro-pyridyl (notably 2-chloro-pyridin-5-yl), 2-trifluoromethyl-pyridyl (notably 2-trifluoromethyl-pyridin-5-yl), 2-methyl-pyrimidyl (notably 2-methyl-pyrimidin-5-yl) and 2-trifluoromethyl-pyrimidyl (notably 2-trifluoromethyl-pyrimidin-5-yl).

The term "6-membered monocyclic heteroaryl group", used alone or in combination, means a 6-membered monocyclic aromatic ring containing one or two nitrogen atoms. Examples of such heteroaryl groups are pyridyl, pyrimidyl, pyridazinyl and pyrazinyl.

Preferred are pyridyl and pyrimidyl. The heteroaryl groups are unsubstituted or substituted as explicitly defined. Examples of such unsubstituted or substituted 6-membered monocyclic heteroaryl groups are pyridyl (notably pyridin-3-yl), 2-chloro-pyridyl (notably 2-chloro-pyridin-5-yl), 2-trifluoromethyl-pyridyl (notably 2-trifluoromethyl-pyridin-5-yl), 2-methyl-pyrimidyl (notably 2-methyl-pyrimidin-5-yl) and 2-trifluoromethyl-pyrimidyl (notably 2-trifluoromethyl-pyrimidin-5-yl).

1P) A further embodiment of the invention relates to compounds according to embodiment 1), wherein n represents 1, 2, 3 or 4;

$R^1$ represents hydrogen and $R^2$ represents hydroxy; hydroxy-$(C_1\text{-}C_3)$alkyl; $(C_1\text{-}C_3)$alkoxy; —$NHR^{11}$; —$N(CH_3)_2$; —CN; —$CONH_2$; $(C_1\text{-}C_4)$alkoxy-carbonyl; $(C_1\text{-}C_4)$alkylamino-carbonyl; aryl which is unsubstituted or mono- or di-substituted with $(C_1\text{-}C_3)$fluoroalkyl or halogen; or heteroaryl which is unsubstituted or mono- or di-substituted with $(C_1\text{-}C_4)$alkyl, $(C_1\text{-}C_3)$fluoroalkyl or halogen; or $R^1$ represents $(C_1\text{-}C_3)$alkyl or hydroxy-$(C_1\text{-}C_3)$alkyl and $R^2$ represents hydrogen;

$R^3$ represents hydrogen or fluoro;

$R^4$ represents hydrogen or fluoro;

$R^5$ represents hydrogen, $(C_1\text{-}C_4)$alkyl or halogen;

$R^6$ represents hydrogen, $(C_1\text{-}C_4)$alkyl, $(C_1\text{-}C_4)$alkoxy, $(C_1\text{-}C_2)$alkoxy-$(C_1\text{-}C_4)$alkyl, amino, nitro or halogen;

$R^7$ represents hydrogen or $(C_1\text{-}C_3)$alkyl;

$R^8$ represents hydrogen, $(C_1\text{-}C_4)$alkyl or hydroxy;

$R^9$ represents hydrogen, $(C_1\text{-}C_4)$alkyl, $(C_1\text{-}C_4)$alkylthio, formyl or halogen;

$R^{10}$ represents chloro, methyl or methoxy; and $R^{11}$ represents hydrogen, benzyl, $(C_1\text{-}C_4)$alkyl-carbonyl, $(C_1\text{-}C_4)$alkoxy-carbonyl or $(C_1\text{-}C_4)$alkyl-sulfonyl which is unsubstituted or mono-substituted with hydroxy or $(C_1\text{-}C_4)$alkoxy-carbonyl;

and to the salts (in particular pharmaceutically acceptable salts) of such compounds.

2) A further embodiment of the invention relates to compounds according to any one of embodiments 1) or 1P), wherein n represents 2, 3 or 4;

$R^1$ represents hydrogen and $R^2$ represents hydroxy; hydroxy-$(C_1\text{-}C_3)$alkyl; —$NHR^{11}$; —CN; or a 5- or 6-membered monocyclic heteroaryl group which group is unsubstituted or mono-substituted with $(C_1\text{-}C_4)$alkyl, $(C_1\text{-}C_3)$fluoroalkyl or halogen; or $R^1$ represents $(C_1\text{-}C_3)$alkyl or hydroxy-$(C_1\text{-}C_3)$alkyl and $R^2$ represents hydrogen;

$R^3$ represents hydrogen or fluoro;

$R^4$ represents hydrogen or fluoro;

$R^5$ represents hydrogen;

$R^6$ represents hydrogen, $(C_1\text{-}C_4)$alkyl, $(C_1\text{-}C_4)$alkoxy, $(C_1\text{-}C_2)$alkoxy-$(C_1\text{-}C_4)$alkyl or amino;
$R^7$ represents hydrogen;
$R^8$ represents hydrogen;
$R^9$ represents hydrogen, $(C_1\text{-}C_4)$alkyl or halogen;
$R^{10}$ represents chloro or methyl; and
$R^{11}$ represents $(C_1\text{-}C_4)$alkyl-sulfonyl which is unsubstituted or mono-substituted with hydroxy or $(C_1\text{-}C_4)$alkoxy-carbonyl;
and to the salts (in particular pharmaceutically acceptable salts) of such compounds.

3) A further embodiment of the invention relates to compounds according to any one of embodiments 1) or 1P), wherein
n represents 2, 3 or 4;
$R^1$ represents hydrogen and $R^2$ represents hydroxy; hydroxy-methyl; —NHR$^{11}$; —CN; or a 5- or 6-membered monocyclic heteroaryl group which group is unsubstituted or mono-substituted with methyl, trifluoromethyl or chloro; or
$R^1$ represents methyl or hydroxy-methyl and $R^2$ represents hydrogen;
$R^3$ represents hydrogen or fluoro;
$R^4$ represents hydrogen or fluoro;
$R^5$ represents hydrogen;
$R^6$ represents hydrogen, methyl, iso-butyl, methoxy or 3-methoxy-prop-1-yl;
$R^7$ represents hydrogen;
$R^8$ represents hydrogen;
$R^9$ represents hydrogen, methyl or fluoro;
$R^{10}$ represents chloro or methyl; and
$R^{11}$ represents methyl-sulfonyl which is unsubstituted or mono-substituted with methoxy-carbonyl; or ethyl-sulfonyl which is mono-substituted with hydroxy;
and to the salts (in particular pharmaceutically acceptable salts) of such compounds.

4) A further embodiment of the invention relates to compounds according to any one of embodiments 1) or 1P), wherein
n represents 1, 2, 3 or 4;
$R^1$ represents hydrogen;
$R^2$ represents hydroxy; hydroxy-$(C_1\text{-}C_3)$alkyl; $(C_1\text{-}C_3)$alkoxy; —NHR$^{11}$; —N(CH$_3$)$_2$; —CN; —CONH$_2$; $(C_1\text{-}C_4)$alkoxy-carbonyl; $(C_1\text{-}C_4)$alkylamino-carbonyl; aryl which is unsubstituted or mono- or di-substituted with $(C_1\text{-}C_3)$fluoroalkyl or halogen; or heteroaryl which is unsubstituted or mono- or di-substituted with $(C_1\text{-}C_4)$alkyl, $(C_1\text{-}C_3)$fluoroalkyl or halogen;
$R^3$ represents hydrogen or fluoro;
$R^4$ represents hydrogen or fluoro;
$R^5$ represents hydrogen, $(C_1\text{-}C_4)$alkyl or halogen;
$R^6$ represents hydrogen, $(C_1\text{-}C_4)$alkyl, $(C_1\text{-}C_4)$alkoxy, $(C_1\text{-}C_2)$alkoxy-$(C_1\text{-}C_4)$alkyl, amino, nitro or halogen;
$R^7$ represents hydrogen or $(C_1\text{-}C_3)$alkyl;
$R^8$ represents hydrogen, $(C_1\text{-}C_4)$alkyl or hydroxy;
$R^9$ represents hydrogen, $(C_1\text{-}C_4)$alkyl, $(C_1\text{-}C_4)$alkylthio, formyl or halogen;
$R^{10}$ represents chloro, methyl or methoxy; and
$R^{11}$ represents hydrogen, benzyl, $(C_1\text{-}C_4)$alkyl-carbonyl, $(C_1\text{-}C_4)$alkoxy-carbonyl or $(C_1\text{-}C_4)$alkyl-sulfonyl which is unsubstituted or mono-substituted with hydroxy or $(C_1\text{-}C_4)$alkoxy-carbonyl;
and to the salts (in particular pharmaceutically acceptable salts) of such compounds.

5) A further embodiment of the invention relates to compounds according to any one of embodiments 1) or 1P), wherein
n represents 2, 3 or 4;
$R^1$ represents hydrogen;
$R^2$ represents hydroxy; hydroxy-$(C_1\text{-}C_3)$alkyl; —NHR$^{11}$; —CN; or a 5- or 6-membered monocyclic heteroaryl group which group is unsubstituted or mono-substituted with $(C_1\text{-}C_4)$alkyl, $(C_1\text{-}C_3)$fluoroalkyl or halogen;
$R^3$ represents hydrogen or fluoro;
$R^4$ represents hydrogen or fluoro;
$R^5$ represents hydrogen;
$R^6$ represents hydrogen, $(C_1\text{-}C_4)$alkyl, $(C_1\text{-}C_4)$alkoxy or $(C_1\text{-}C_2)$alkoxy-$(C_1\text{-}C_4)$alkyl;
$R^7$ represents hydrogen;
$R^8$ represents hydrogen;
$R^9$ represents hydrogen, $(C_1\text{-}C_4)$alkyl or halogen;
$R^{10}$ represents chloro or methyl; and
$R^{11}$ represents $(C_1\text{-}C_4)$alkyl-sulfonyl which is unsubstituted or mono-substituted with hydroxy or $(C_1\text{-}C_4)$alkoxy-carbonyl;
and to the salts (in particular pharmaceutically acceptable salts) of such compounds.

6) A further embodiment of the invention relates to compounds according to any one of embodiments 1) or 1P), wherein
n represents 2, 3 or 4;
$R^1$ represents hydrogen;
$R^2$ represents hydroxy; hydroxy-methyl; —NHR$^{11}$; —CN; or a 5- or 6-membered monocyclic heteroaryl group which group is unsubstituted or mono-substituted with methyl, trifluoromethyl or chloro;
$R^3$ represents hydrogen or fluoro;
$R^4$ represents hydrogen or fluoro;
$R^5$ represents hydrogen;
$R^6$ represents hydrogen, methyl, iso-butyl, methoxy or 3-methoxy-prop-1-yl;
$R^7$ represents hydrogen;
$R^8$ represents hydrogen;
$R^9$ represents hydrogen, methyl or fluoro;
$R^{10}$ represents chloro or methyl; and
$R^{11}$ represents methyl-sulfonyl which is unsubstituted or mono-substituted with methoxy-carbonyl; or ethyl-sulfonyl which is mono-substituted with hydroxy;
and to the salts (in particular pharmaceutically acceptable salts) of such compounds.

7) A further embodiment of the invention relates to compounds according to any one of embodiments 1) or 1P), wherein
n represents 2 or 3;
$R^1$ represents hydrogen;
$R^2$ represents hydroxy; or a 6-membered monocyclic heteroaryl group which group is unsubstituted or mono-substituted with methyl, trifluoromethyl or chloro;
$R^3$ represents hydrogen or fluoro;
$R^4$ represents hydrogen or fluoro;
$R^5$ represents hydrogen;
$R^6$ represents hydrogen, methyl, iso-butyl, methoxy or 3-methoxy-prop-1-yl;
$R^7$ represents hydrogen;
$R^8$ represents hydrogen;
$R^9$ represents hydrogen; and
$R^{10}$ represents chloro;
and to the salts (in particular pharmaceutically acceptable salts) of such compounds.

8) A further embodiment of the invention relates to compounds according to any one of embodiments 1) or 1P), wherein n represents 2 or 3;
$R^1$ represents $(C_1-C_3)$alkyl or hydroxy-$(C_1-C_3)$alkyl;
$R^2$ represents hydrogen;
$R^3$ represents hydrogen or fluoro;
$R^4$ represents hydrogen or fluoro;
$R^5$ represents hydrogen;
$R^6$ represents hydrogen;
$R^7$ represents hydrogen or $(C_1-C_3)$alkyl;
$R^8$ represents hydrogen;
$R^9$ represents hydrogen or formyl; and
$R^{10}$ represents chloro;
and to the salts (in particular pharmaceutically acceptable salts) of such compounds.

9) A further embodiment of the invention relates to compounds according to any one of embodiments 1) or 1P), wherein
n represents 2 or 3;
$R^1$ represents methyl or hydroxy-methyl;
$R^2$ represents hydrogen;
$R^3$ represents hydrogen or fluoro;
$R^4$ represents hydrogen or fluoro;
$R^5$ represents hydrogen;
$R^6$ represents hydrogen;
$R^7$ represents hydrogen or methyl;
$R^8$ represents hydrogen;
$R^9$ represents hydrogen; and
$R^{10}$ represents chloro;
and to the salts (in particular pharmaceutically acceptable salts) of such compounds.

10) A further embodiment of the invention relates to compounds according to any one of embodiments 1) to 6), wherein
n represents 2 or 3;
and to the salts (in particular pharmaceutically acceptable salts) of such compounds.

11) A further embodiment of the invention relates to compounds according to any one of embodiments 1) to 3), 8) or 9), wherein
$R^1$ represents hydroxy-methyl;
and to the salts (in particular pharmaceutically acceptable salts) of such compounds.

12) A further embodiment of the invention relates to compounds according to any one of embodiments 1) to 2), 4), 5) or 10), wherein
$R^2$ represents hydroxy; hydroxy-$(C_1-C_3)$alkyl; —$NHR^{11}$; or —CN; and
$R^{11}$ represents methyl-sulfonyl which is unsubstituted or mono-substituted with methoxy-carbonyl; or ethyl-sulfonyl which is mono-substituted with hydroxy;
and to the salts (in particular pharmaceutically acceptable salts) of such compounds.

13) A further embodiment of the invention relates to compounds according to any one of embodiments 1) to 7) or 10), wherein
$R^2$ represents hydroxy;
and to the salts (in particular pharmaceutically acceptable salts) of such compounds.

14) A further embodiment of the invention relates to compounds according to any one of embodiments 1) to 2), 4), 5) or 10), wherein
$R^2$ represents a 5- or 6-membered monocyclic heteroaryl group which group is unsubstituted or mono-substituted with $(C_1-C_4)$alkyl, $(C_1-C_3)$fluoroalkyl or halogen; and to the salts (in particular pharmaceutically acceptable salts) of such compounds.

15) A further embodiment of the invention relates to compounds according to any one of embodiments 1) to 7) or 10), wherein
$R^2$ represents a 6-membered monocyclic heteroaryl group which group is unsubstituted or mono-substituted with methyl, trifluoromethyl or chloro;
and to the salts (in particular pharmaceutically acceptable salts) of such compounds.

16) A further embodiment of the invention relates to compounds according to any one of embodiments 1) to 15), wherein
$R^3$ and $R^4$ represent hydrogen;
and to the salts (in particular pharmaceutically acceptable salts) of such compounds.

17) A further embodiment of the invention relates to compounds according to any one of embodiments 1) to 15), wherein
$R^3$ and $R^4$ represent fluoro;
and to the salts (in particular pharmaceutically acceptable salts) of such compounds.

18) A further embodiment of the invention relates to compounds according to any one of embodiments 1), 1P), 4) or 10) to 17), wherein
$R^5$ represents hydrogen;
and to the salts (in particular pharmaceutically acceptable salts) of such compounds.

19) A further embodiment of the invention relates to compounds according to any one of embodiments 1) to 7) or 10) to 18), wherein
$R^6$ represents hydrogen;
and to the salts (in particular pharmaceutically acceptable salts) of such compounds.

20) A further embodiment of the invention relates to compounds according to any one of embodiments 1) to 2), 4), 5) or 10) to 18), wherein
$R^6$ represents $(C_1-C_4)$alkyl, $(C_1-C_4)$alkoxy or $(C_1-C_2)$alkoxy-$(C_1-C_4)$alkyl;
and to the salts (in particular pharmaceutically acceptable salts) of such compounds.

21) A further embodiment of the invention relates to compounds according to any one of embodiments 1), 1P), 4), 8), 9) or 10) to 20), wherein
$R^7$ represents hydrogen;
and to the salts (in particular pharmaceutically acceptable salts) of such compounds.

22) A further embodiment of the invention relates to compounds according to any one of embodiments 1), 1P), 4) or 10) to 21), wherein
$R^8$ represents hydrogen;
and to the salts (in particular pharmaceutically acceptable salts) of such compounds.

23) A further embodiment of the invention relates to compounds according to any one of embodiments 1) to 6), 8) or 10) to 22), wherein
$R^9$ represents hydrogen;
and to the salts (in particular pharmaceutically acceptable salts) of such compounds.

24) A further embodiment of the invention relates to compounds according to any one of embodiments 1) to 6) or 10) to 22), wherein
$R^9$ represents methyl or fluoro;
and to the salts (in particular pharmaceutically acceptable salts) of such compounds.

25) A further embodiment of the invention relates to compounds according to any one of embodiments 1) to 6), 8), 10) to 17), 19) or 20), wherein $R^5$, $R^7$, $R^8$ and $R^9$ represent hydrogen;
and to the salts (in particular pharmaceutically acceptable salts) of such compounds.

26) A further embodiment of the invention relates to compounds according to any one of embodiments 1) to 6) or 10) to 25), wherein $R^{10}$ represents chloro;
and to the salts (in particular pharmaceutically acceptable salts) of such compounds.

27) A further embodiment of the invention relates to compounds according to any one of embodiments 1) to 2), 4), 5), 10) or 16) to 26), wherein $R^{11}$ represents methyl-sulfonyl which is unsubstituted or mono-substituted with methoxy-carbonyl; or ethyl-sulfonyl which is mono-substituted with hydroxy;
and to the salts (in particular pharmaceutically acceptable salts) of such compounds.

28) A further embodiment of the invention relates to compounds according to any one of embodiments 1) to 3), 8) to 11) or 16) to 26), wherein, in case $R^1$ is different from hydrogen, the stereogenic center is as depicted in formula $(I_{St1})$

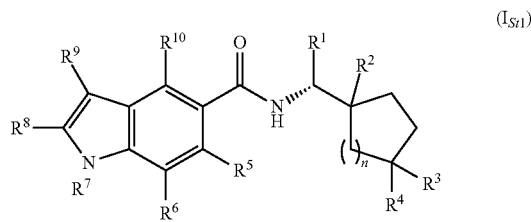

and to the salts (in particular pharmaceutically acceptable salts) of such compounds.

29) Preferred compounds of formula (I) as defined in embodiment 1) are selected from the group consisting of:

4-Chloro-1H-indole-5-carboxylic acid ((S)-1-cyclohexyl-2-hydroxy-ethyl)-amide;
4-Chloro-1H-indole-5-carboxylic acid (1-hydroxy-cyclohexylmethyl)-amide;
4-Chloro-1H-indole-5-carboxylic acid (1-hydroxy-cycloheptylmethyl)-amide;
4-Chloro-1H-indole-5-carboxylic acid (4,4-difluoro-1-hydroxy-cyclohexylmethyl)-amide;
4-Chloro-1H-indole-5-carboxylic acid [(S)-1-(4,4-difluoro-cyclohexyl)-2-hydroxy-ethyl]-amide;
4-Chloro-1-methyl-1H-indole-5-carboxylic acid (1-hydroxy-cyclohexylmethyl)-amide;
4-Chloro-1-methyl-1H-indole-5-carboxylic acid ((S)-1-cyclohexyl-2-hydroxy-ethyl)-amide;
4-Chloro-3-formyl-1H-indole-5-carboxylic acid ((S)-1-cyclohexyl-2-hydroxy-ethyl)-amide;
4-Chloro-3-formyl-1H-indole-5-carboxylic acid (1-hydroxy-cyclohexylmethyl)-amide;
4-Chloro-1H-indole-5-carboxylic acid (1-cycloheptyl-2-hydroxy-ethyl)-amide;
4-Chloro-1H-indole-5-carboxylic acid [1-(2-trifluoromethyl-pyrimidin-5-yl)-cyclohexylmethyl]-amide;
4-Chloro-1H-indole-5-carboxylic acid [1-(6-chloro-pyridin-3-yl)-cyclohexylmethyl]-amide;
4-Chloro-1H-indole-5-carboxylic acid [1-(6-trifluoromethyl-pyridin-3-yl)-cyclohexylmethyl]-amide;
4-Chloro-1H-indole-5-carboxylic acid [1-(6-chloro-pyridin-3-yl)-4,4-difluoro-cyclohexylmethyl]-amide;
4-Chloro-1H-indole-5-carboxylic acid [1-(4-chloro-phenyl)-cyclohexylmethyl]-amide;
4-Chloro-1H-indole-5-carboxylic acid [1-(4-trifluoromethyl-phenyl)-cyclohexylmethyl]-amide;
4-Chloro-1H-indole-5-carboxylic acid (1-pyridin-3-yl-cyclohexylmethyl)-amide;
4-Chloro-1H-indole-5-carboxylic acid (1-pyridin-3-yl-cyclopentylmethyl)-amide;
4-Chloro-1H-indole-5-carboxylic acid (1-pyridin-3-yl-cycloheptylmethyl)-amide;
4-Chloro-7-methyl-1H-indole-5-carboxylic acid (1-hydroxy-cyclohexylmethyl)-amide;
4-Chloro-2-oxo-2,3-dihydro-1H-indole-5-carboxylic acid (1-hydroxy-cycloheptylmethyl)-amide;
4-Chloro-2-methyl-1H-indole-5-carboxylic acid (1-hydroxy-cyclohexylmethyl)-amide;
4-Chloro-7-iodo-3-methylsulfanyl-1H-indole-5-carboxylic acid (1-hydroxy-cyclohexylmethyl)-amide;
4-Chloro-7-methyl-1H-indole-5-carboxylic acid (4,4-difluoro-1-hydroxy-cyclohexylmethyl)-amide;
4-Chloro-7-methyl-1H-indole-5-carboxylic acid (1-hydroxy-cycloheptylmethyl)-amide;
4-Chloro-3-fluoro-1H-indole-5-carboxylic acid (1-hydroxy-cycloheptylmethyl)-amide;
4-Methoxy-1H-indole-5-carboxylic acid (1-hydroxy-cycloheptylmethyl)-amide;
3,4-Dichloro-1H-indole-5-carboxylic acid (1-hydroxy-cyclohexylmethyl)-amide;
4-Chloro-7-nitro-1H-indole-5-carboxylic acid (1-hydroxy-cyclohexylmethyl)-amide;
1-{[(4-Chloro-1H-indole-5-carbonyl)-amino]-methyl}-cyclohexanecarboxylic acid methyl ester;
4-Chloro-1H-indole-5-carboxylic acid (1-hydroxymethyl-cyclohexylmethyl)-amide;
7-Amino-4-chloro-1H-indole-5-carboxylic acid (1-hydroxy-cyclohexylmethyl)-amide;
4-Chloro-3-methyl-1H-indole-5-carboxylic acid (1-hydroxy-cycloheptylmethyl)-amide;
4-Chloro-1H-indole-5-carboxylic acid (1-carbamoyl-cyclohexylmethyl)-amide;
4-Chloro-1H-indole-5-carboxylic acid (1-methylcarbamoyl-cyclohexylmethyl)-amide;
4-Chloro-1H-indole-5-carboxylic acid (1-cyano-cyclohexylmethyl)-amide;
(1-{[(4-Chloro-1H-indole-5-carbonyl)-amino]-methyl}-cyclohexyl)-carbamic acid tert-butyl ester;
4,6-Dichloro-1H-indole-5-carboxylic acid (4,4-difluoro-1-hydroxy-cyclohexylmethyl)-amide;
4-Chloro-1H-indole-5-carboxylic acid (1-amino-cyclohexylmethyl)-amide;
4-Chloro-6-methyl-1H-indole-5-carboxylic acid (1-hydroxy-cyclohexylmethyl)-amide;
4-Chloro-1H-indole-5-carboxylic acid (1-hydroxy-cyclopentylmethyl)-amide;
4-Chloro-1H-indole-5-carboxylic acid (1-hydroxy-cyclooctylmethyl)-amide;
4-Chloro-1H-indole-5-carboxylic acid (1-methoxy-cyclohexylmethyl)-amide;
4-Chloro-1H-indole-5-carboxylic acid ((S)-1-cyclohexyl-ethyl)-amide;
4-Chloro-1H-indole-5-carboxylic acid ((R)-1-cyclohexyl-ethyl)-amide;
4-Chloro-1H-indole-5-carboxylic acid (1-acetylamino-cyclohexylmethyl)-amide;
4-Chloro-1H-indole-5-carboxylic acid (1-methanesulfonylamino-cyclohexylmethyl)-amide;

4-Chloro-1H-indole-5-carboxylic acid (1-dimethylamino-cyclohexylmethyl)-amide;

4-Chloro-1H-indole-5-carboxylic acid (1-benzylamino-cyclohexylmethyl)-amide;

3-Bromo-4-chloro-7-methyl-1H-indole-5-carboxylic acid (1-hydroxy-cyclohexylmethyl)-amide;

(1-{[(4-Chloro-1H-indole-5-carbonyl)-amino]-methyl}-cyclohexylsulfamoyl)-acetic acid methyl ester;

4-Chloro-7-isobutyl-1H-indole-5-carboxylic acid (1-hydroxy-cycloheptylmethyl)-amide;

4-Chloro-7-(3-methoxy-propyl)-1H-indole-5-carboxylic acid (1-hydroxy-cycloheptylmethyl)-amide;

4-Chloro-7-isobutyl-1H-indole-5-carboxylic acid (4,4-difluoro-1-hydroxy-cyclohexylmethyl)-amide;

4-Chloro-7-(3-methoxy-propyl)-1H-indole-5-carboxylic acid (4,4-difluoro-1-hydroxy-cyclohexylmethyl)-amide;

4-Chloro-1H-indole-5-carboxylic acid [1-(2-hydroxy-ethanesulfonylamino)-cyclohexylmethyl]-amide;

4-Methyl-1H-indole-5-carboxylic acid (1-hydroxy-cyclohexylmethyl)-amide;

4-Chloro-1H-indole-5-carboxylic acid [1-(2-methyl-pyrimidin-5-yl)-cyclohexylmethyl]-amide;

4-Chloro-7-methoxy-1H-indole-5-carboxylic acid (4,4-difluoro-1-hydroxy-cyclohexylmethyl)-amide;

4-Chloro-1H-indole-5-carboxylic acid [4,4-difluoro-1-(2-methyl-pyrimidin-5-yl)-cyclohexylmethyl]-amide;

4-Chloro-7-methyl-1H-indole-5-carboxylic acid [4,4-difluoro-1-(2-methyl-pyrimidin-5-yl)-cyclohexylmethyl]-amide;

4-Chloro-7-methyl-1H-indole-5-carboxylic acid [1-(2-methyl-pyrimidin-5-yl)-cyclohexylmethyl]-amide;

4,7-Dimethyl-1H-indole-5-carboxylic acid (4,4-difluoro-1-hydroxy-cyclohexylmethyl)-amide; and 4-Methyl-1H-indole-5-carboxylic acid (4,4-difluoro-1-hydroxy-cyclohexylmethyl)-amide;

or salts (in particular pharmaceutically acceptable salts) of such compounds;

it is to be understood for any of the above listed compounds, that a stereogenic center, which is not specifically assigned, may be in absolute (R)- or absolute (S)-configuration; for example a compound listed as 4-Chloro-1H-indole-5-carboxylic acid (1-cycloheptyl-2-hydroxy-ethyl)-amide may be 4-Chloro-1H-indole-5-carboxylic acid ((S)-1-cycloheptyl-2-hydroxy-ethyl)-amide, 4-Chloro-1H-indole-5-carboxylic acid ((R)-1-cycloheptyl-2-hydroxy-ethyl)-amide or any mixture thereof.

It is understood that in this specification the phrase "according to any one of embodiments 1) to X)", wherein "X" represents an integer between 2 and 29, refers to all embodiments between 1) and X) in the alternative, including embodiment 1P) as one of the alternatives; for instance the phrase "according to any one of embodiments 1) to 2)" means "according to any one of embodiments 1) or 1P) or 2)".

30) A further embodiment of the invention relates to compounds according to embodiment 1), which are also compounds of formula ($I_{HET}$)

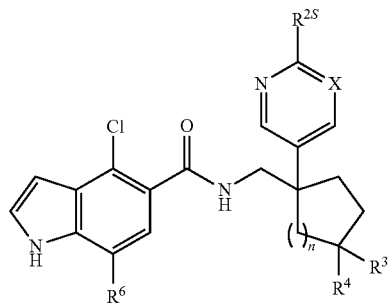

wherein n represents 2 or 3;

X represents CH or N;

$R^{2S}$ represents hydrogen, $(C_1-C_4)$alkyl, $(C_1-C_3)$fluoroalkyl or halogen;

$R^3$ represents hydrogen or fluoro;

$R^4$ represents hydrogen or fluoro; and $R^6$ represents hydrogen or $(C_1-C_4)$alkyl;

and to the salts (in particular pharmaceutically acceptable salts) of such compounds.

31) A further embodiment of the invention relates to compounds according to embodiment 30), wherein n represents 2 or 3;

X represents CH or N;

$R^{2S}$ represents hydrogen, methyl, trifluoromethyl or chloro;

$R^3$ represents hydrogen or fluoro;

$R^4$ represents hydrogen or fluoro; and $R^6$ represents hydrogen or methyl;

and to the salts (in particular pharmaceutically acceptable salts) of such compounds.

32) A further embodiment of the invention relates to compounds according to any one of embodiments 30) or 31), wherein X represents N;

and to the salts (in particular pharmaceutically acceptable salts) of such compounds.

33) A further embodiment of the invention relates to compounds according to any one of embodiments 30) to 32), wherein $R^{2S}$ represents methyl or trifluoromethyl;

and to the salts (in particular pharmaceutically acceptable salts) of such compounds.

34) A further embodiment of the invention relates to compounds according to any one of embodiments 30) to 33), wherein $R^6$ represents methyl;

and to the salts (in particular pharmaceutically acceptable salts) of such compounds.

35) A further embodiment of the invention relates to compounds according to embodiment 1), which are also compounds of formula ($I_{OH}$)

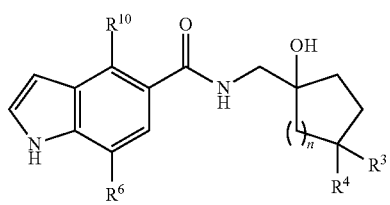

wherein n represents 2 or 3;

R³ represents hydrogen or fluoro;

R⁴ represents hydrogen or fluoro;

R⁶ represents $(C_1-C_4)$alkyl, $(C_1-C_4)$alkoxy, hydroxy-$(C_1-C_4)$alkyl, hydroxy-$(C_2-C_4)$alkoxy, $(C_1-C_2)$alkoxy-$(C_1-C_4)$alkyl or halogen; and R¹⁰ represents chloro, methyl or trifluoromethyl;

and to the salts (in particular pharmaceutically acceptable salts) of such compounds.

36) A further embodiment of the invention relates to compounds according to embodiment 35), wherein R³ and R⁴ represent fluoro;

and to the salts (in particular pharmaceutically acceptable salts) of such compounds.

37) A further embodiment of the invention relates to compounds according to any one of embodiments 35) or 36), wherein R⁶ represents methyl, ethyl, n-propyl, iso-butyl, methoxy, ethoxy, 1-hydroxy-ethyl, 2-hydroxy-prop-2-yl, 2-hydroxy-ethoxy, 2-ethoxy-ethyl, 2-methoxy-prop-2-yl, 3-methoxy-prop-1-yl or chloro;

and to the salts (in particular pharmaceutically acceptable salts) of such compounds.

38) A further embodiment of the invention relates to compounds according to any one of embodiments 35) to 37), wherein R¹⁰ represents chloro;

and to the salts (in particular pharmaceutically acceptable salts) of such compounds.

39) A further embodiment of the invention relates to compounds according to any one of embodiments 1), 10) to 18) or 21) to 28), wherein R⁶ represents hydrogen, $(C_1-C_4)$alkyl, $(C_1-C_4)$alkoxy, hydroxy-$(C_1-C_4)$alkyl, hydroxy-$(C_2-C_4)$alkoxy, $(C_1-C_2)$alkoxy-$(C_1-C_4)$alkyl or halogen;

and to the salts (in particular pharmaceutically acceptable salts) of such compounds.

40) A further embodiment of the invention relates to compounds according to any one of embodiments 1), 10) to 18) or 21) to 28), wherein R⁶ represents hydrogen, methyl, ethyl, n-propyl, iso-butyl, methoxy, ethoxy, 1-hydroxy-ethyl, 2-hydroxy-prop-2-yl, 2-hydroxy-ethoxy, 2-ethoxy-ethyl, 2-methoxy-prop-2-yl, 3-methoxy-prop-1-yl or chloro;

and to the salts (in particular pharmaceutically acceptable salts) of such compounds.

41) A further embodiment of the invention relates to compounds according to any one of embodiments 1), 10) to 25), 27), 28), 39) or 40), wherein R¹⁰ represents chloro, methyl or trifluoromethyl;

and to the salts (in particular pharmaceutically acceptable salts) of such compounds.

42) Further preferred compounds of formula (I) as defined in embodiment 1) are selected from the group consisting of:

4-Ethyl-1H-indole-5-carboxylic acid (4,4-difluoro-1-hydroxy-cyclohexylmethyl)-amide;

7-Acetyl-4-chloro-1H-indole-5-carboxylic acid (4,4-difluoro-1-hydroxy-cyclohexylmethyl)-amide;

4-Chloro-7-(1-hydroxy-ethyl)-1H-indole-5-carboxylic acid (4,4-difluoro-1-hydroxy-cyclohexylmethyl)-amide;

4-Chloro-7-(1-hydroxy-1-methyl-ethyl)-1H-indole-5-carboxylic acid (4,4-difluoro-1-hydroxy-cyclohexylmethyl)-amide;

7-Methyl-4-trifluoromethyl-1H-indole-5-carboxylic acid (1-hydroxy-cyclohexylmethyl)-amide;

7-Methyl-4-trifluoromethyl-1H-indole-5-carboxylic acid (4,4-difluoro-1-hydroxy-cyclohexylmethyl)-amide;

4,7-Dimethyl-1H-indole-5-carboxylic acid (1-hydroxy-cyclohexylmethyl)-amide;

4-Chloro-7-ethyl-1H-indole-5-carboxylic acid (1-hydroxy-cyclohexylmethyl)-amide;

4-Chloro-7-ethyl-1H-indole-5-carboxylic acid (4,4-difluoro-1-hydroxy-cyclohexylmethyl)-amide;

7-Chloro-4-methyl-1H-indole-5-carboxylic acid (1-hydroxy-cyclohexylmethyl)-amide;

7-Chloro-4-methyl-1H-indole-5-carboxylic acid (4,4-difluoro-1-hydroxy-cyclohexylmethyl)-amide;

4-Chloro-7-methoxy-1H-indole-5-carboxylic acid (1-hydroxy-cyclohexylmethyl)-amide;

7-Methoxy-4-methyl-1H-indole-5-carboxylic acid (4,4-difluoro-1-hydroxy-cyclohexylmethyl)-amide;

7-Methoxy-4-methyl-1H-indole-5-carboxylic acid (1-hydroxy-cyclohexylmethyl)-amide;

4-Chloro-7-ethoxy-1H-indole-5-carboxylic acid (1-hydroxy-cyclohexylmethyl)-amide;

4-Chloro-7-hydroxy-1H-indole-5-carboxylic acid (4,4-difluoro-1-hydroxy-cyclohexylmethyl)-amide;

4-Chloro-7-ethoxy-1H-indole-5-carboxylic acid (4,4-difluoro-1-hydroxy-cyclohexyl methyl)-amide;

4-Chloro-7-propyl-1H-indole-5-carboxylic acid (1-hydroxy-cyclohexylmethyl)-amide;

4-Chloro-7-propyl-1H-indole-5-carboxylic acid (4,4-difluoro-1-hydroxy-cyclohexylmethyl)-amide;

7-(2-tert-Butoxy-ethoxy)-4-chloro-1H-indole-5-carboxylic acid (1-hydroxy-cyclohexylmethyl)-amide;

7-(2-tert-Butoxy-ethoxy)-4-chloro-1H-indole-5-carboxylic acid (4,4-difluoro-1-hydroxy-cyclohexylmethyl)-amide;

4-Chloro-7-(2-hydroxy-ethoxy)-1H-indole-5-carboxylic acid (1-hydroxy-cyclohexylmethyl)-amide;

4-Chloro-7-(2-hydroxy-ethoxy)-1H-indole-5-carboxylic acid (4,4-difluoro-1-hydroxy-cyclohexylmethyl)-amide;

7-Acetyl-4-chloro-1H-indole-5-carboxylic acid (1-hydroxy-cyclohexylmethyl)-amide;

4-Chloro-7-(1-hydroxy-1-methyl-ethyl)-1H-indole-5-carboxylic acid (1-hydroxy-cyclohexylmethyl)-amide;

4,7-Difluoro-1H-indole-5-carboxylic acid (1-hydroxy-cyclohexylmethyl)-amide;

4,7-Difluoro-1H-indole-5-carboxylic acid (4,4-difluoro-1-hydroxy-cyclohexylmethyl)-amide;

4-Fluoro-7-methoxy-1H-indole-5-carboxylic acid (1-hydroxy-cyclohexylmethyl)-amide;

4-Fluoro-7-methoxy-1H-indole-5-carboxylic acid (4,4-difluoro-1-hydroxy-cyclohexylmethyl)-amide;

4-Chloro-7-(2-ethoxy-ethyl)-1H-indole-5-carboxylic acid (4,4-difluoro-1-hydroxy-cyclohexylmethyl)-amide;

and

4-Chloro-7-(1-methoxy-1-methyl-ethyl)-1H-indole-5-carboxylic acid (4,4-difluoro-1-hydroxy-cyclohexylmethyl)-amide;

it is to be understood for any of the above listed compounds, that a stereogenic center, which is not specifically assigned, may be in absolute (R)- or absolute (S)-configuration; for example a compound listed as 4-Chloro-7-(1-hydroxy-ethyl)-1H-indole-5-carboxylic acid (4,4-difluoro-1-hydroxy-cyclohexylmethyl)-amide may be 4-Chloro-7-((R)-1-hydroxy-ethyl)-1H-indole-5-carboxylic acid (4,4-difluoro-1-hydroxy-cyclohexylmethyl)-amide, 4-Chloro-7-((S)-1-hydroxy-ethyl)-1H-indole-5-carboxylic acid (4,4-difluoro-1-hydroxy-cyclohexylmethyl)-amide or any mixture thereof.

It is well understood that the invention relates to compounds according to embodiment 1); or according to embodiment 1) limited by the features of an embodiment dependent on embodiment 1; or according to embodiment 1) limited by the features of a cascade of dependent embodiments e.g. in the form of "embodiment 3) depending on embodiment 2) depending on embodiment 1)". In case of an embodiment depending on more than one other embodiment, it is understood that each combination is specifically disclosed. Also, in case an embodiment is dependent on more than one other embodiment and one or more of said other embodiments are themselves dependent on one or more further embodiments, it is understood that each combination is specifically disclosed if obtainable with regard to the given dependencies and multiple dependencies. Notably, embodiments resulting from cascades of more than three embodiments depending on each other may be construed under observance of the given dependencies and multiple dependencies and are thus intended to be specifically disclosed. Representative examples of embodiments which are possible based on the dependencies of the embodiments 1) to 42) as disclosed hereinabove and which are therefore intended and herewith specifically disclosed in individualized form are:

1, 1P+1, 2+1P+1, 3+1P+1, 4+1P+1, 5+1P+1, 6+1P+1, 7+1P+1, 8+1P+1, 9+1P+1, 10+1P+1, 10+2+1P+1, 10+3+1P+1, 10+4+1P+1, 10+5+1P+1, 10+6+1P+1, 11+1P+1, 11+8+1P+1, 11+9+1P+1, 12+1P+1, 12+5+1P+1, 13+1P+1, 13+5+1P+1, 13+6+1P+1, 13+10+1P+1, 13+10+2+1P+1, 13+10+3+1P+1, 13+10+4+1P+1, 13+10+5+1P+1, 13+10+6+1P+1, 14+1P+1, 14+5+1P+1, 14+10+1P+1, 14+10+2+1P+1, 14+10+3+1P+1, 14+10+4+1P+1, 14+10+5+1P+1, 14+10+6+1P+1, 15+1P+1, 15+5+1P+1, 15+6+1P+1, 15+10+1P+1, 15+10+2+1P+1, 15+10+3+1P+1, 15+10+4+1P+1, 15+10+5+1P+1, 15+10+6+1P+1, 16+1P+1, 16+5+1P+1, 16+6+1P+1, 16+8+1P+1, 16+10+1P+1, 16+10+2+1P+1, 16+10+3+1P+1, 16+10+4+1P+1, 16+10+5+1P+1, 16+10+6+1P+1, 16+13+1P+1, 16+13+5+1P+1, 16+13+6+1P+1, 16+13+10+1P+1, 16+13+10+2+1P+1, 16+13+10+3+1P+1, 16+13+10+4+1P+1, 16+13+10+5+1P+1, 16+13+10+6+1P+1, 16+15+1P+1, 16+15+5+1P+1, 16+15+6+1P+1, 16+15+10+1P+1, 16+15+10+2+1P+1, 16+15+10+3+1P+1, 16+15+10+4+1P+1, 16+15+10+5+1P+1, 16+15+10+6+1P+1, 17+1P+1, 17+5+1P+1, 17+6+1P+1, 17+8+1P+1, 17+10+1P+1, 17+10+2+1P+1, 17+10+3+1P+1, 17+10+4+1P+1, 17+10+5+1P+1, 17+10+6+1P+1, 17+13+1P+1, 17+13+5+1P+1, 17+13+6+1P+1, 17+13+10+1P+1, 17+13+10+2+1P+1, 17+13+10+3+1P+1, 17+13+10+4+1P+1, 17+13+10+5+1P+1, 17+13+10+6+1P+1, 17+15+1P+1, 17+15+5+1P+1, 17+15+6+1P+1, 17+15+10+1P+1, 17+15+10+2+1P+1, 17+15+10+3+1P+1, 17+15+10+4+1P+1, 17+15+10+5+1P+1, 17+15+10+6+1P+1, 19+1P+1, 19+5+1P+1, 19+6+1P+1, 19+10+1P+1, 19+10+2+1P+1, 19+10+3+1P+1, 19+10+4+1P+1, 19+10+5+1P+1, 19+10+6+1P+1, 19+13+1P+1, 19+13+5+1P+1, 19+13+6+1P+1, 19+13+10+1P+1, 19+13+10+2+1P+1, 19+13+10+3+1P+1, 19+13+10+4+1P+1, 19+13+10+5+1P+1, 19+13+10+6+1P+1, 19+15+1P+1, 19+15+5+1P+1, 19+15+6+1P+1, 19+15+10+1P+1, 19+15+10+2+1P+1, 19+15+10+3+1P+1, 19+15+10+4+1P+1, 19+15+10+5+1P+1, 19+15+10+6+1P+1, 19+16+1P+1, 19+16+5+1P+1, 19+16+6+1P+1, 19+16+8+1P+1, 19+16+10+1P+1, 19+16+10+2+1P+1, 19+16+10+3+1P+1, 19+16+10+4+1P+1, 19+16+10+5+1P+1, 19+16+10+6+1P+1, 19+16+13+1P+1, 19+16+13+5+1P+1, 19+16+13+6+1P+1, 19+16+13+10+1P+1, 19+16+13+10+2+1P+1, 19+16+13+10+3+1P+1, 19+16+13+10+4+1P+1, 19+16+13+10+5+1P+1, 19+16+13+10+6+1P+1, 19+16+15+1P+1, 19+16+15+5+1P+1, 19+16+15+6+1P+1, 19+16+15+10+1P+1, 19+16+15+10+2+1P+1, 19+16+15+10+3+1P+1, 19+16+15+10+4+1P+1, 19+16+15+10+5+1P+1, 19+16+15+10+6+1P+1, 19+17+1P+1, 19+17+5+1P+1, 19+17+6+1P+1, 19+17+8+1P+1, 19+17+10+1P+1, 19+17+10+2+1P+1, 19+17+10+3+1P+1, 19+17+10+4+1P+1, 19+17+10+5+1P+1, 19+17+10+6+1P+1, 19+17+13+1P+1, 19+17+13+5+1P+1, 19+17+13+6+1P+1, 19+17+13+10+1P+1, 19+17+13+10+2+1P+1, 19+17+13+10+3+1P+1, 19+17+13+10+4+1P+1, 19+17+13+10+5+1P+1, 19+17+13+10+6+1P+1, 19+17+15+1P+1, 19+17+15+5+1P+1, 19+17+15+6+1P+1, 19+17+15+10+1P+1, 19+17+15+10+2+1P+1, 19+17+15+10+3+1P+1, 19+17+15+10+4+1P+1, 19+17+15+10+5+1P+1, 19+17+15+10+6+1P+1, 20+1P+1, 20+5+1P+1, 20+10+1P+1, 20+10+2+1P+1, 20+10+3+1P+1, 20+10+4+1P+1, 20+10+5+1P+1, 20+10+6+1P+1, 20+13+1P+1, 20+13+5+1P+1, 20+13+6+1P+1, 20+13+10+1P+1, 20+13+10+2+1P+1, 20+13+10+3+1P+1, 20+13+10+4+1P+1, 20+13+10+5+1P+1, 20+13+10+6+1P+1, 20+15+1P+1, 20+15+5+1P+1, 20+15+6+1P+1, 20+15+10+1P+1, 20+15+10+2+1P+1, 20+15+10+3+1P+1, 20+15+10+4+1P+1, 20+15+10+5+1P+1, 20+15+10+6+1P+1, 20+16+1P+1, 20+16+5+1P+1, 20+16+6+1P+1, 20+16+8+1P+1, 20+16+10+1P+1, 20+16+10+2+1P+1, 20+16+10+3+1P+1, 20+16+10+4+1P+1, 20+16+10+5+1P+1, 20+16+10+6+1P+1, 20+16+13+1P+1, 20+16+13+5+1P+1, 20+16+13+6+1P+1, 20+16+13+10+1P+1, 20+16+13+10+2+1P+1, 20+16+13+10+3+1P+1, 20+16+13+10+4+1P+1, 20+16+13+10+5+1P+1, 20+16+13+10+6+1P+1, 20+16+15+1P+1, 20+16+15+5+1P+1, 20+16+15+6+1P+1, 20+16+15+10+1P+1, 20+16+15+10+2+1P+1, 20+16+15+10+3+1P+1, 20+16+15+10+4+1P+1, 20+16+15+10+5+1P+1, 20+16+15+10+6+1P+1, 20+17+1P+1, 20+17+5+1P+1, 20+17+6+1P+1, 20+17+8+1P+1, 20+17+10+1P+1, 20+17+10+2+1P+1, 20+17+10+3+1P+1, 20+17+10+4+1P+1, 20+17+10+5+1P+1, 20+17+10+6+1P+1, 20+17+13+1P+1, 20+17+13+5+1P+1, 20+17+13+6+1P+1, 20+17+13+10+1P+1, 20+17+13+10+2+1P+1, 20+17+13+10+3+1P+1, 20+17+13+10+4+1P+1, 20+17+13+10+5+1P+1, 20+17+13+10+6+1P+1, 20+17+15+1P+1, 20+17+15+5+1P+1, 20+17+15+6+1P+1, 20+17+15+10+1P+1, 20+17+15+10+2+1P+1, 20+17+15+10+3+1P+1, 20+17+15+10+4+1P+1, 20+17+15+10+5+1P+1, 20+17+15+10+6+1P+1, 24+1P+1, 24+13+1P+1, 24+13+5+1P+1, 24+13+6+1P+1, 24+13+10+1P+1, 24+13+10+2+1P+1, 24+13+10+3+1P+1, 24+13+10+4+1P+1, 24+13+10+5+1P+1, 24+13+10+6+1P+1, 25+1P+1, 25+5+1P+1, 25+6+1P+1, 25+8+1P+1, 25+10+1P+1, 25+10+2+1P+1, 25+10+3+1P+1, 25+10+4+1P+1, 25+10+5+1P+1, 25+10+6+1P+1, 25+13+1P+1, 25+13+5+1P+1, 25+13+6+1P+1, 25+13+10+1P+1, 25+13+10+2+1P+1, 25+13+10+3+1P+1, 25+13+10+4+1P+1, 25+13+10+5+1P+1, 25+13+10+6+1P+1, 25+15+1P+1, 25+15+5+1P+1, 25+15+6+1P+1, 25+15+10+1P+1, 25+15+10+2+1P+1, 25+15+10+3+1P+1, 25+15+10+4+1P+1, 25+15+10+5+1P+1, 25+15+10+6+1P+1, 25+16+1P+1, 25+16+5+1P+1, 25+16+6+1P+1, 25+16+8+1P+1, 25+16+10+1P+1, 25+16+10+2+1P+1, 25+16+10+3+1P+1, 25+16+10+4+1P+1, 25+16+10+5+1P+1, 25+16+10+6+1P+1, 25+16+13+1P+1, 25+16+13+5+1P+1, 25+16+13+6+1P+1, 25+16+13+10+1P+1, 25+16+13+10+2+1P+1, 25+16+13+10+3+1P+1, 25+16+13+10+4+1P+1, 25+16+13+10+5+1P+1, 25+16+13+10+6+1P+1, 25+16+15+1P+1, 25+16+15+5+1P+1, 25+16+15+6+1P+1, 25+16+15+10+1P+1, 25+16+15+10+2+1P+1, 25+16+15+10+3+1P+1, 25+16+15+10+4+1P+1, 25+16+15+10+5+1P+1, 25+16+15+10+6+1P+1, 25+17+1P+1, 25+17+5+1P+1, 25+17+6+1P+1, 25+17+8+1P+1, 25+17+10+1P+1, 25+17+10+2+1P+1, 25+17+10+3+1P+1, 25+17+10+4+1P+1, 25+17+10+5+1P+1, 25+17+10+6+1P+1, 25+17+13+1P+1, 25+17+13+5+1P+1, 25+17+13+6+1P+1, 25+17+13+10+1P+1, 25+17+13+10+2+1P+1,

25+17+13+10+3+1P+1, 25+17+13+10+4+1P+1, 25+17+13+10+5+1P+1, 25+17+13+10+6+1P+1, 25+17+15+1P+1, 25+17+15+5+1P+1, 25+17+15+6+1P+1, 25+17+15+10+1P+1, 25+17+15+10+2+1P+1, 25+17+15+10+3+1P+1, 25+17+15+10+4+1P+1, 25+17+15+10+5+1P+1, 25+17+15+10+6+1P+1, 25+19+1P+1, 25+19+5+1P+1, 25+19+6+1P+1, 25+19+10+1P+1, 25+19+10+2+1P+1, 25+19+10+3+1P+1, 25+19+10+4+1P+1, 25+19+10+5+1P+1, 25+19+10+6+1P+1, 25+19+13+1P+1, 25+19+13+5+1P+1, 25+19+13+6+1P+1, 25+19+13+10+1P+1, 25+19+13+10+2+1P+1, 25+19+13+10+3+1P+1, 25+19+13+10+4+1P+1, 25+19+13+10+5+1P+1, 25+19+13+10+6+1P+1, 25+19+15+1P+1, 25+19+15+5+1P+1, 25+19+15+6+1P+1, 25+19+15+10+1P+1, 25+19+15+10+2+1P+1, 25+19+15+10+3+1P+1, 25+19+15+10+4+1P+1, 25+19+15+10+5+1P+1, 25+19+15+10+6+1P+1, 25+19+16+1P+1, 25+19+16+5+1P+1, 25+19+16+6+1P+1, 25+19+16+8+1P+1, 25+19+16+10+1P+1, 25+19+16+10+2+1P+1, 25+19+16+10+3+1P+1, 25+19+16+10+4+1P+1, 25+19+16+10+5+1P+1, 25+19+16+10+6+1P+1, 25+19+16+13+1P+1, 25+19+16+13+5+1P+1, 25+19+16+13+6+1P+1, 25+19+16+13+10+1P+1, 25+19+16+13+10+2+1P+1, 25+19+16+13+10+3+1P+1, 25+19+16+13+10+4+1P+1, 25+19+16+13+10+5+1P+1, 25+19+16+13+10+6+1P+1, 25+19+16+15+1P+1, 25+19+16+15+5+1P+1, 25+19+16+15+6+1P+1, 25+19+16+15+10+1P+1, 25+19+16+15+10+2+1P+1, 25+19+16+15+10+3+1P+1, 25+19+16+15+10+4+1P+1, 25+19+16+15+10+5+1P+1, 25+19+16+15+10+6+1P+1, 25+19+17+1P+1, 25+19+17+5+1P+1, 25+19+17+6+1P+1, 25+19+17+8+1P+1, 25+19+17+10+1P+1, 25+19+17+10+2+1P+1, 25+19+17+10+3+1P+1, 25+19+17+10+4+1P+1, 25+19+17+10+5+1P+1, 25+19+17+10+6+1P+1, 25+19+17+13+1P+1, 25+19+17+13+5+1P+1, 25+19+17+13+6+1P+1, 25+19+17+13+10+1P+1, 25+19+17+13+10+2+1P+1, 25+19+17+13+10+3+1P+1, 25+19+17+13+10+4+1P+1, 25+19+17+13+10+5+1P+1, 25+19+17+13+10+6+1P+1, 25+19+17+15+1P+1, 25+19+17+15+5+1P+1, 25+19+17+15+6+1P+1, 25+19+17+15+10+1P+1, 25+19+17+15+10+2+1P+1, 25+19+17+15+10+3+1P+1, 25+19+17+15+10+4+1P+1, 25+19+17+15+10+5+1P+1, 25+19+17+15+10+6+1P+1, 25+20+1P+1, 25+20+5+1P+1, 25+20+10+1P+1, 25+20+10+2+1P+1, 25+20+10+3+1P+1, 25+20+10+4+1P+1, 25+20+10+5+1P+1, 25+20+10+6+1P+1, 25+20+13+1P+1, 25+20+13+5+1P+1, 25+20+13+6+1P+1, 25+20+13+10+1P+1, 25+20+13+10+2+1P+1, 25+20+13+10+3+1P+1, 25+20+13+10+4+1P+1, 25+20+13+10+5+1P+1, 25+20+13+10+6+1P+1, 25+20+15+1P+1, 25+20+15+5+1P+1, 25+20+15+6+1P+1, 25+20+15+10+1P+1, 25+20+15+10+2+1P+1, 25+20+15+10+3+1P+1, 25+20+15+10+4+1P+1, 25+20+15+10+5+1P+1, 25+20+15+10+6+1P+1, 25+20+16+1P+1, 25+20+16+5+1P+1, 25+20+16+6+1P+1, 25+20+16+8+1P+1, 25+20+16+10+1P+1, 25+20+16+10+2+1P+1, 25+20+16+10+3+1P+1, 25+20+16+10+4+1P+1, 25+20+16+10+5+1P+1, 25+20+16+10+6+1P+1, 25+20+16+13+1P+1, 25+20+16+13+5+1P+1, 25+20+16+13+6+1P+1, 25+20+16+13+10+1P+1, 25+20+16+13+10+2+1P+1, 25+20+16+13+10+3+1P+1, 25+20+16+13+10+4+1P+1, 25+20+16+13+10+5+1P+1, 25+20+16+13+10+6+1P+1, 25+20+16+15+1P+1, 25+20+16+15+5+1P+1, 25+20+16+15+6+1P+1, 25+20+16+15+10+1P+1, 25+20+16+15+10+2+1P+1, 25+20+16+15+10+3+1P+1, 25+20+16+15+10+4+1P+1, 25+20+16+15+10+5+1P+1, 25+20+16+15+10+6+1P+1, 25+20+17+1P+1, 25+20+17+5+1P+1, 25+20+17+6+1P+1, 25+20+17+8+1P+1, 25+20+17+10+1P+1, 25+20+17+10+2+1P+1, 25+20+17+10+3+1P+1, 25+20+17+10+4+1P+1, 25+20+17+10+5+1P+1, 25+20+17+10+6+1P+1, 25+20+17+13+1P+1, 25+20+17+13+5+1P+1, 25+20+17+13+6+1P+1, 25+20+17+13+10+1P+1, 25+20+17+13+10+2+1P+1, 25+20+17+13+10+3+1P+1, 25+20+17+13+10+4+1P+1, 25+20+17+13+10+5+1P+1, 25+20+17+13+10+6+1P+1, 25+20+17+15+1P+1, 25+20+17+15+5+1P+1, 25+20+17+15+6+1P+1, 25+20+17+15+10+1P+1, 25+20+17+15+10+2+1P+1, 25+20+17+15+10+3+1P+1, 25+20+17+15+10+4+1P+1, 25+20+17+15+10+5+1P+1, 25+20+17+15+10+6+1P+1, 26+1P+1, 26+5+1P+1, 26+6+1P+1, 26+19+1P+1, 26+19+5+1P+1, 26+19+6+1P+1, 26+19+10+1P+1, 26+19+10+2+1P+1, 26+19+10+3+1P+1, 26+19+10+4+1P+1, 26+19+10+5+1P+1, 26+19+10+6+1P+1, 26+19+13+1P+1, 26+19+13+5+1P+1, 26+19+13+6+1P+1, 26+19+13+10+1P+1, 26+19+13+10+2+1P+1, 26+19+13+10+3+1P+1, 26+19+13+10+4+1P+1, 26+19+13+10+5+1P+1, 26+19+13+10+6+1P+1, 26+19+15+1P+1, 26+19+15+5+1P+1, 26+19+15+6+1P+1, 26+19+15+10+1P+1, 26+19+15+10+2+1P+1, 26+19+15+10+3+1P+1, 26+19+15+10+4+1P+1, 26+19+15+10+5+1P+1, 26+19+15+10+6+1P+1, 26+19+16+1P+1, 26+19+16+5+1P+1, 26+19+16+6+1P+1, 26+19+16+8+1P+1, 26+19+16+10+1P+1, 26+19+16+10+2+1P+1, 26+19+16+10+3+1P+1, 26+19+16+10+4+1P+1, 26+19+16+10+5+1P+1, 26+19+16+10+6+1P+1, 26+19+16+13+1P+1, 26+19+16+13+5+1P+1, 26+19+16+13+6+1P+1, 26+19+16+13+10+1P+1, 26+19+16+13+10+2+1P+1, 26+19+16+13+10+3+1P+1, 26+19+16+13+10+4+1P+1, 26+19+16+13+10+5+1P+1, 26+19+16+13+10+6+1P+1, 26+19+16+15+1P+1, 26+19+16+15+5+1P+1, 26+19+16+15+6+1P+1, 26+19+16+15+10+1P+1, 26+19+16+15+10+2+1P+1, 26+19+16+15+10+3+1P+1, 26+19+16+15+10+4+1P+1, 26+19+16+15+10+5+1P+1, 26+19+16+15+10+6+1P+1, 26+19+17+1P+1, 26+19+17+5+1P+1, 26+19+17+6+1P+1, 26+19+17+8+1P+1, 26+19+17+10+1P+1, 26+19+17+10+2+1P+1, 26+19+17+10+3+1P+1, 26+19+17+10+4+1P+1, 26+19+17+10+5+1P+1, 26+19+17+10+6+1P+1, 26+19+17+13+1P+1, 26+19+17+13+5+1P+1, 26+19+17+13+6+1P+1, 26+19+17+13+10+1P+1, 26+19+17+13+10+2+1P+1, 26+19+17+13+10+3+1P+1, 26+19+17+13+10+4+1P+1, 26+19+17+13+10+5+1P+1, 26+19+17+13+10+6+1P+1, 26+19+17+15+1P+1, 26+19+17+15+5+1P+1, 26+19+17+15+6+1P+1, 26+19+17+15+10+1P+1, 26+19+17+15+10+2+1P+1, 26+19+17+15+10+3+1P+1, 26+19+17+15+10+4+1P+1, 26+19+17+15+10+5+1P+1, 26+19+17+15+10+6+1P+1, 26+20+1P+1, 26+20+5+1P+1, 26+20+10+1P+1, 26+20+10+2+1P+1, 26+20+10+3+1P+1, 26+20+10+4+1P+1, 26+20+10+5+1P+1, 26+20+10+6+1P+1, 26+20+13+1P+1, 26+20+13+5+1P+1, 26+20+13+6+1P+1, 26+20+13+10+1P+1, 26+20+13+10+2+1P+1, 26+20+13+10+3+1P+1, 26+20+13+10+4+1P+1, 26+20+13+10+5+1P+1, 26+20+13+10+6+1P+1, 26+20+15+1P+1, 26+20+15+5+1P+1, 26+20+15+6+1P+1, 26+20+15+10+1P+1, 26+20+15+10+2+1P+1, 26+20+15+10+3+1P+1, 26+20+15+10+4+1P+1, 26+20+15+10+5+1P+1, 26+20+15+10+6+1P+1, 26+20+16+1P+1, 26+20+16+5+1P+1, 26+20+16+6+1P+1, 26+20+16+8+1P+1, 26+20+16+10+1P+1, 26+20+16+10+2+1P+1, 26+20+16+10+3+1P+1, 26+20+16+10+4+1P+1, 26+20+16+10+5+1P+1, 26+20+16+10+6+1P+1, 26+20+16+13+1P+1, 26+20+16+13+5+1P+1, 26+20+16+13+6+1P+1, 26+20+16+13+10+1P+1, 26+20+16+13+10+2+1P+1, 26+20+16+13+10+3+1P+1, 26+20+16+13+10+4+1P+1, 26+20+16+13+10+5+1P+1, 26+20+16+13+10+6+1P+1, 26+20+16+15+1P+1, 26+20+16+15+5+1P+1, 26+20+16+15+6+1P+1, 26+20+16+15+10+1P+1, 26+20+16+15+10+2+1P+1, 26+20+16+15+10+3+1P+1, 26+20+16+15+10+4+1P+1, 26+20+16+15+10+5+1P+1, 26+20+16+15+10+6+1P+1, 26+20+17+1P+1, 26+20+17+5+1P+1, 26+20+17+6+1P+1, 26+20+17+8+1P+1, 26+20+17+10+1P+1, 26+20+17+10+2+1P+1, 26+20+17+10+3+1P+1, 26+20+17+10+4+

1P+1, 26+20+17+10+5+1P+1, 26+20+17+10+6+1P+1, 26+20+17+13+1P+1, 26+20+17+13+5+1P+1, 26+20+17+13+6+1P+1, 26+20+17+13+10+1P+1, 26+20+17+13+10+2+1P+1, 26+20+17+13+10+3+1P+1, 26+20+17+13+10+4+1P+1, 26+20+17+13+10+5+1P+1, 26+20+17+13+10+6+1P+1, 26+20+17+15+1P+1, 26+20+17+15+5+1P+1, 26+20+17+15+6+1P+1, 26+20+17+15+10+1P+1, 26+20+17+15+10+2+1P+1, 26+20+17+15+10+3+1P+1, 26+20+17+15+10+4+1P+1, 26+20+17+15+10+5+1P+1, 26+20+17+15+10+6+1P+1, 26+25+1P+1, 26+25+5+1P+1, 26+25+6+1P+1, 26+25+8+1P+1, 26+25+10+1P+1, 26+25+10+2+1P+1, 26+25+10+3+1P+1, 26+25+10+4+1P+1, 26+25+10+5+1P+1, 26+25+10+6+1P+1, 26+25+13+1P+1, 26+25+13+5+1P+1, 26+25+13+6+1P+1, 26+25+13+10+1P+1, 26+25+13+10+2+1P+1, 26+25+13+10+3+1P+1, 26+25+13+10+4+1P+1, 26+25+13+10+5+1P+1, 26+25+13+10+6+1P+1, 26+25+15+1P+1, 26+25+15+5+1P+1, 26+25+15+6+1P+1, 26+25+15+10+1P+1, 26+25+15+10+2+1P+1, 26+25+15+10+3+1P+1, 26+25+15+10+4+1P+1, 26+25+15+10+5+1P+1, 26+25+15+10+6+1P+1, 26+25+16+1P+1, 26+25+16+5+1P+1, 26+25+16+6+1P+1, 26+25+16+8+1P+1, 26+25+16+10+1P+1, 26+25+16+10+2+1P+1, 26+25+16+10+3+1P+1, 26+25+16+10+4+1P+1, 26+25+16+10+5+1P+1, 26+25+16+10+6+1P+1, 26+25+16+13+1P+1, 26+25+16+13+5+1P+1, 26+25+16+13+6+1P+1, 26+25+16+13+10+1P+1, 26+25+16+13+10+2+1P+1, 26+25+16+13+10+3+1P+1, 26+25+16+13+10+4+1P+1, 26+25+16+13+10+5+1P+1, 26+25+16+13+10+6+1P+1, 26+25+16+15+1P+1, 26+25+16+15+5+1P+1, 26+25+16+15+6+1P+1, 26+25+16+15+10+1P+1, 26+25+16+15+10+2+1P+1, 26+25+16+15+10+3+1P+1, 26+25+16+15+10+4+1P+1, 26+25+16+15+10+5+1P+1, 26+25+16+15+10+6+1P+1, 26+25+17+1P+1, 26+25+17+5+1P+1, 26+25+17+6+1P+1, 26+25+17+8+1P+1, 26+25+17+10+1P+1, 26+25+17+10+2+1P+1, 26+25+17+10+3+1P+1, 26+25+17+10+4+1P+1, 26+25+17+10+5+1P+1, 26+25+17+10+6+1P+1, 26+25+17+13+1P+1, 26+25+17+13+5+1P+1, 26+25+17+13+6+1P+1, 26+25+17+13+10+1P+1, 26+25+17+13+10+2+1P+1, 26+25+17+13+10+3+1P+1, 26+25+17+13+10+4+1P+1, 26+25+17+13+10+5+1P+1, 26+25+17+13+10+6+1P+1, 26+25+17+15+1P+1, 26+25+17+15+5+1P+1, 26+25+17+15+6+1P+1, 26+25+17+15+10+1P+1, 26+25+17+15+10+2+1P+1, 26+25+17+15+10+3+1P+1, 26+25+17+15+10+4+1P+1, 26+25+17+15+10+5+1P+1, 26+25+17+15+10+6+1P+1, 26+25+19+1P+1, 26+25+19+5+1P+1, 26+25+19+6+1P+1, 26+25+19+10+1P+1, 26+25+19+10+2+1P+1, 26+25+19+10+3+1P+1, 26+25+19+10+4+1P+1, 26+25+19+10+5+1P+1, 26+25+19+10+6+1P+1, 26+25+19+13+1P+1, 26+25+19+13+5+1P+1, 26+25+19+13+6+1P+1, 26+25+19+13+10+1P+1, 26+25+19+13+10+2+1P+1, 26+25+19+13+10+3+1P+1, 26+25+19+13+10+4+1P+1, 26+25+19+13+10+5+1P+1, 26+25+19+13+10+6+1P+1, 26+25+19+15+1P+1, 26+25+19+15+5+1P+1, 26+25+19+15+6+1P+1, 26+25+19+15+10+1P+1, 26+25+19+15+10+2+1P+1, 26+25+19+15+10+3+1P+1, 26+25+19+15+10+4+1P+1, 26+25+19+15+10+5+1P+1, 26+25+19+15+10+6+1P+1, 26+25+19+16+1P+1, 26+25+19+16+5+1P+1, 26+25+19+16+6+1P+1, 26+25+19+16+8+1P+1, 26+25+19+16+10+1P+1, 26+25+19+16+10+2+1P+1, 26+25+19+16+10+3+1P+1, 26+25+19+16+10+4+1P+1, 26+25+19+16+10+5+1P+1, 26+25+19+16+10+6+1P+1, 26+25+19+16+13+1P+1, 26+25+19+16+13+5+1P+1, 26+25+19+16+13+6+1P+1, 26+25+19+16+13+10+1P+1, 26+25+19+16+13+10+2+1P+1, 26+25+19+16+13+10+3+1P+1, 26+25+19+16+13+10+4+1P+1, 26+25+19+16+13+10+5+1P+1, 26+25+19+16+13+10+6+1P+1, 26+25+19+16+15+1P+1, 26+25+19+16+15+5+1P+1, 26+25+19+16+15+6+1P+1, 26+25+19+16+15+10+1P+1, 26+25+19+16+15+10+2+1P+1, 26+25+19+16+15+10+3+1P+1, 26+25+19+16+15+10+4+1P+1, 26+25+19+16+15+10+5+1P+1, 26+25+19+16+15+10+6+1P+1, 26+25+19+17+1P+1, 26+25+19+17+5+1P+1, 26+25+19+17+6+1P+1, 26+25+19+17+8+1P+1, 26+25+19+17+10+1P+1, 26+25+19+17+10+2+1P+1, 26+25+19+17+10+3+1P+1, 26+25+19+17+10+4+1P+1, 26+25+19+17+10+5+1P+1, 26+25+19+17+10+6+1P+1, 26+25+19+17+13+1P+1, 26+25+19+17+13+5+1P+1, 26+25+19+17+13+6+1P+1, 26+25+19+17+13+10+1P+1, 26+25+19+17+13+10+2+1P+1, 26+25+19+17+13+10+3+1P+1, 26+25+19+17+13+10+4+1P+1, 26+25+19+17+13+10+5+1P+1, 26+25+19+17+13+10+6+1P+1, 26+25+19+17+15+1P+1, 26+25+19+17+15+5+1P+1, 26+25+19+17+15+6+1P+1, 26+25+19+17+15+10+1P+1, 26+25+19+17+15+10+2+1P+1, 26+25+19+17+15+10+3+1P+1, 26+25+19+17+15+10+4+1P+1, 26+25+19+17+15+10+5+1P+1, 26+25+19+17+15+10+6+1P+1, 26+25+20+1P+1, 26+25+20+5+1P+1, 26+25+20+10+1P+1, 26+25+20+10+2+1P+1, 26+25+20+10+3+1P+1, 26+25+20+10+4+1P+1, 26+25+20+10+5+1P+1, 26+25+20+10+6+1P+1, 26+25+20+13+1P+1, 26+25+20+13+5+1P+1, 26+25+20+13+6+1P+1, 26+25+20+13+10+1P+1, 26+25+20+13+10+2+1P+1, 26+25+20+13+10+3+1P+1, 26+25+20+13+10+4+1P+1, 26+25+20+13+10+5+1P+1, 26+25+20+13+10+6+1P+1, 26+25+20+15+1P+1, 26+25+20+15+5+1P+1, 26+25+20+15+6+1P+1, 26+25+20+15+10+1P+1, 26+25+20+15+10+2+1P+1, 26+25+20+15+10+3+1P+1, 26+25+20+15+10+4+1P+1, 26+25+20+15+10+5+1P+1, 26+25+20+15+10+6+1P+1, 26+25+20+16+1P+1, 26+25+20+16+5+1P+1, 26+25+20+16+6+1P+1, 26+25+20+16+8+1P+1, 26+25+20+16+10+1P+1, 26+25+20+16+10+2+1P+1, 26+25+20+16+10+3+1P+1, 26+25+20+16+10+4+1P+1, 26+25+20+16+10+5+1P+1, 26+25+20+16+10+6+1P+1, 26+25+20+16+13+1P+1, 26+25+20+16+13+5+1P+1, 26+25+20+16+13+6+1P+1, 26+25+20+16+13+10+1P+1, 26+25+20+16+13+10+2+1P+1, 26+25+20+16+13+10+3+1P+1, 26+25+20+16+13+10+4+1P+1, 26+25+20+16+13+10+5+1P+1, 26+25+20+16+13+10+6+1P+1, 26+25+20+16+15+1P+1, 26+25+20+16+15+5+1P+1, 26+25+20+16+15+6+1P+1, 26+25+20+16+15+10+1P+1, 26+25+20+16+15+10+2+1P+1, 26+25+20+16+15+10+3+1P+1, 26+25+20+16+15+10+4+1P+1, 26+25+20+16+15+10+5+1P+1, 26+25+20+16+15+10+6+1P+1, 26+25+20+17+1P+1, 26+25+20+17+5+1P+1, 26+25+20+17+6+1P+1, 26+25+20+17+8+1P+1, 26+25+20+17+10+1P+1, 26+25+20+17+10+2+1P+1, 26+25+20+17+10+3+1P+1, 26+25+20+17+10+4+1P+1, 26+25+20+17+10+5+1P+1, 26+25+20+17+10+6+1P+1, 26+25+20+17+13+1P+1, 26+25+20+17+13+5+1P+1, 26+25+20+17+13+6+1P+1, 26+25+20+17+13+10+1P+1, 26+25+20+17+13+10+2+1P+1, 26+25+20+17+13+10+3+1P+1, 26+25+20+17+13+10+4+1P+1, 26+25+20+17+13+10+5+1P+1, 26+25+20+17+13+10+6+1P+1, 26+25+20+17+15+1P+1, 26+25+20+17+15+5+1P+1, 26+25+20+17+15+6+1P+1, 26+25+20+17+15+10+1P+1, 26+25+20+17+15+10+2+1P+1, 26+25+20+17+15+10+3+1P+1, 26+25+20+17+15+10+4+1P+1, 26+25+20+17+15+10+5+1P+1, 26+25+20+17+15+10+6+1P+1, 28+1P+1, 28+8+1P+1, 28+9+1P+1, 29+1P+1, 30+1, 31+30+1, 32+30+1, 32+31+30+1, 33+30+1, 33+31+30+1, 33+32+30+1, 33+32+31+30+1, 34+30+1, 34+31+30+1, 34+32+30+1, 34+32+31+30+1, 34+33+30+1, 34+33+31+30+1, 34+33+32+30+1, 34+33+32+31+30+1, 35+1, 36+35+1, 37+35+1, 37+36+35+1, 38+35+1, 38+36+35+1, 38+37+35+1, 38+37+36+35+1, 39+1, 39+10+1, 39+12+1, 39+12+10+1, 39+13+1, 39+13+10+1, 39+14+1, 39+14+10+1, 39+15+1, 39+15+10+1, 39+16+1, 39+16+10+1, 39+16+12+1, 39+16+12+10+1, 39+16+13+1, 39+16+13+10+1, 39+16+14+1, 39+16+14+

10+1, 39+16+15+1, 39+16+15+10+1, 39+17+1, 39+17+10+1, 39+17+12+1, 39+17+12+10+1, 39+17+13+1, 39+17+13+10+1, 39+17+14+1, 39+17+14+10+1, 39+17+15+1, 39+17+15+10+1, 39+25+1, 39+25+10+1, 39+25+12+1, 39+25+12+10+1, 39+25+13+1, 39+25+13+10+1, 39+25+14+1, 39+25+14+10+1, 39+25+15+1, 39+25+15+10+1, 39+25+16+1, 39+25+16+10+1, 39+25+16+12+1, 39+25+16+12+10+1, 39+25+16+13+1, 39+25+16+13+10+1, 39+25+16+14+1, 39+25+16+14+10+1, 39+25+16+15+1, 39+25+16+15+10+1, 39+25+17+1, 39+25+17+10+1, 39+25+17+12+1, 39+25+17+12+10+1, 39+25+17+13+1, 39+25+17+13+10+1, 39+25+17+14+1, 39+25+17+14+10+1, 39+25+17+15+1, 39+25+17+15+10+1, 39+26+1, 39+26+25+1, 39+26+25+10+1, 39+26+25+12+1, 39+26+25+12+10+1, 39+26+25+13+1, 39+26+25+13+10+1, 39+26+25+14+1, 39+26+25+14+10+1, 39+26+25+15+1, 39+26+25+15+10+1, 39+26+25+16+1, 39+26+25+16+10+1, 39+26+25+16+12+1, 39+26+25+16+12+10+1, 39+26+25+16+13+1, 39+26+25+16+13+10+1, 39+26+25+16+14+1, 39+26+25+16+14+10+1, 39+26+25+16+15+1, 39+26+25+16+15+10+1, 39+26+25+17+1, 39+26+25+17+10+1, 39+26+25+17+12+1, 39+26+25+17+12+10+1, 39+26+25+17+13+1, 39+26+25+17+13+10+1, 39+26+25+17+14+1, 39+26+25+17+14+10+1, 39+26+25+17+15+1, 39+26+25+17+15+10+1, 40+1, 40+10+1, 40+12+1, 40+12+10+1, 40+13+1, 40+13+10+1, 40+14+1, 40+14+10+1, 40+15+1, 40+15+10+1, 40+16+1, 40+16+10+1, 40+16+12+1, 40+16+12+10+1, 40+16+13+1, 40+16+13+10+1, 40+16+14+1, 40+16+14+10+1, 40+16+15+1, 40+16+15+10+1, 40+17+1, 40+17+10+1, 40+17+12+1, 40+17+12+10+1, 40+17+13+1, 40+17+13+10+1, 40+17+14+1, 40+17+14+10+1, 40+17+15+1, 40+17+15+10+1, 40+25+1, 40+25+10+1, 40+25+12+1, 40+25+12+10+1, 40+25+13+1, 40+25+13+10+1, 40+25+14+1, 40+25+14+10+1, 40+25+15+1, 40+25+15+10+1, 40+25+16+1, 40+25+16+10+1, 40+25+16+12+1, 40+25+16+12+10+1, 40+25+16+13+1, 40+25+16+13+10+1, 40+25+16+14+1, 40+25+16+14+10+1, 40+25+16+15+1, 40+25+16+15+10+1, 40+25+17+1, 40+25+17+10+1, 40+25+17+12+1, 40+25+17+12+10+1, 40+25+17+13+1, 40+25+17+13+10+1, 40+25+17+14+1, 40+25+17+14+10+1, 40+25+17+15+1, 40+25+17+15+10+1, 40+26+1, 40+26+25+1, 40+26+25+10+1, 40+26+25+12+1, 40+26+25+12+10+1, 40+26+25+13+1, 40+26+25+13+10+1, 40+26+25+14+1, 40+26+25+14+10+1, 40+26+25+15+1, 40+26+25+15+10+1, 40+26+25+16+1, 40+26+25+16+10+1, 40+26+25+16+12+1, 40+26+25+16+12+10+1, 40+26+25+16+13+1, 40+26+25+16+13+10+1, 40+26+25+16+14+1, 40+26+25+16+14+10+1, 40+26+25+16+15+1, 40+26+25+16+15+10+1, 40+26+25+17+1, 40+26+25+17+10+1, 40+26+25+17+12+1, 40+26+25+17+12+10+1, 40+26+25+17+13+1, 40+26+25+17+13+10+1, 40+26+25+17+14+1, 40+26+25+17+14+10+1, 40+26+25+17+15+1, 40+26+25+17+15+10+1, 41+1, 41+39+1, 41+39+10+1, 41+39+12+1, 41+39+12+10+1, 41+39+13+1, 41+39+13+10+1, 41+39+14+1, 41+39+14+10+1, 41+39+15+1, 41+39+15+10+1, 41+39+16+1, 41+39+16+10+1, 41+39+16+12+1, 41+39+16+12+10+1, 41+39+16+13+1, 41+39+16+13+10+1, 41+39+16+14+1, 41+39+16+14+10+1, 41+39+16+15+1, 41+39+16+15+10+1, 41+39+17+1, 41+39+17+10+1, 41+39+17+12+1, 41+39+17+12+10+1, 41+39+17+13+1, 41+39+17+13+10+1, 41+39+17+14+1, 41+39+17+14+10+1, 41+39+17+15+1, 41+39+17+15+10+1, 41+39+25+1, 41+39+25+10+1, 41+39+25+12+1, 41+39+25+12+10+1, 41+39+25+13+1, 41+39+25+13+10+1, 41+39+25+14+1, 41+39+25+14+10+1, 41+39+25+15+1, 41+39+25+15+10+1, 41+39+25+16+1, 41+39+25+16+10+1, 41+39+25+16+12+1, 41+39+25+16+12+10+1, 41+39+25+16+13+1, 41+39+25+16+13+10+1, 41+39+25+16+14+1, 41+39+25+16+14+10+1, 41+39+25+16+15+1, 41+39+25+16+15+10+1, 41+39+25+17+1, 41+39+25+17+10+1, 41+39+25+17+12+1, 41+39+25+17+12+10+1, 41+39+25+17+13+1, 41+39+25+17+13+10+1, 41+39+25+17+14+1, 41+39+25+17+14+10+1, 41+39+25+17+15+1, 41+39+25+17+15+10+1, 41+40+1, 41+40+10+1, 41+40+12+1, 41+40+12+10+1, 41+40+13+1, 41+40+13+10+1, 41+40+14+1, 41+40+14+10+1, 41+40+15+1, 41+40+15+10+1, 41+40+16+1, 41+40+16+10+1, 41+40+16+12+1, 41+40+16+12+10+1, 41+40+16+13+1, 41+40+16+13+10+1, 41+40+16+14+1, 41+40+16+14+10+1, 41+40+16+15+1, 41+40+16+15+10+1, 41+40+17+1, 41+40+17+10+1, 41+40+17+12+1, 41+40+17+12+10+1, 41+40+17+13+1, 41+40+17+13+10+1, 41+40+17+14+1, 41+40+17+14+10+1, 41+40+17+15+1, 41+40+17+15+10+1, 41+40+25+1, 41+40+25+10+1, 41+40+25+12+1, 41+40+25+12+10+1, 41+40+25+13+1, 41+40+25+13+10+1, 41+40+25+14+1, 41+40+25+14+10+1, 41+40+25+15+1, 41+40+25+15+10+1, 41+40+25+16+1, 41+40+25+16+10+1, 41+40+25+16+12+1, 41+40+25+16+12+10+1, 41+40+25+16+13+1, 41+40+25+16+13+10+1, 41+40+25+16+14+1, 41+40+25+16+14+10+1, 41+40+25+16+15+1, 41+40+25+16+15+10+1, 41+40+25+17+1, 41+40+25+17+10+1, 41+40+25+17+12+1, 41+40+25+17+12+10+1, 41+40+25+17+13+1, 41+40+25+17+13+10+1, 41+40+25+17+14+1, 41+40+25+17+14+10+1, 41+40+25+17+15+1, 41+40+25+17+15+10+1, and 42+1;

wherein the list above is not to be construed as limiting with respect to further embodiments which are also possible based on the dependencies of the embodiments 1) to 42) as disclosed hereinabove and which are also intended. In the list above the numbers refer to the embodiments according to their numbering provided hereinabove whereas "+" indicates the dependency from another embodiment. The different individualized embodiments are separated by commas. In other words, "10+2+1P+1" for example refers to embodiment 10) depending on embodiment 2) depending on embodiment 1P) depending on embodiment 1), i.e. embodiment "10+2+1P+1" corresponds to embodiment 1) further limited by the features of embodiments 1P), 2) and 10).

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 42), or pharmaceutically acceptable salts thereof, are suitable for use as medicaments. In particular, compounds of formula (I) modulate the $P2X_7$ receptor, i.e. they act as $P2X_7$ receptor antagonists, and are useful for the prevention or treatment of diseases which are associated with the activation of the $P2X_7$ receptor such as pain; neurodegenerative and neuroinflammatory diseases; bone and joint diseases; obstructive diseases of the airways; cardiovascular diseases; eye diseases; skin diseases; abdominal and gastrointestinal tract diseases; genitourinary diseases; cancer; other auto-immune and allergic disorders; and other disorders with an inflammatory or immunological component.

In particular, the compounds of formula (I) according to any one of embodiments 1) to 42), or pharmaceutically acceptable salts thereof, are suitable for the prevention or treatment of pain. Pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain.

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Chronic articular pain conditions include especially rheumatoid arthritis, osteoarthritis, rheumatoid spondylitis, gouty arthritis and juvenile arthritis.

Pain associated with functional bowel disorders includes especially non-ulcer dyspepsia, non-cardiac chest pain and irritable bowel syndrome.

Further, the compounds of formula (I) according to any one of embodiments 1) to 42), or pharmaceutically acceptable salts thereof, are suitable for the prevention or treatment of neurodegenerative and neuroinflammatory diseases. Neurodegenerative and neuro-inflammatory diseases include Alzheimer's disease and other dementing disorders including, but not limited to, Creutzfeldt-Jakob disease (CJD) and new variant Creutzfeldt-Jakob disease (nvCJD); Amyotrophic lateral sclerosis, amyloidosis; multiple sclerosis and other demyelinating syndromes; cerebral atherosclerosis and vasculitis; temporal arteritis; myasthenia gravis; Hunting-ton's disease; Lewy Body dementia; and Parkinson's disease.

Further, the compounds of formula (I) according to any one of embodiments 1) to 42), or pharmaceutically acceptable salts thereof, are suitable for the prevention or treatment of bone and joint diseases. Bone and joint diseases include arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; arthritides associated with or including osteoarthritis/osteoarthrosis, both primary and secondary to, for example, congenital hip dysplasia; cervical and lumbar spondylitis; Still's disease; seronegative spondyloarthropathies including ankylosing spondylitis, psoriatic arthritis, reactive arthritis and undifferentiated spondyloarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Familial Mediterranean fever, Muckle-Wells syndrome, and Familial Hibernian Fever, Kikuchi disease; and drug-induced arthalgias, tendonitis, and myopathies including dystrophies and other inflammatory myopathies.

Further, the compounds of formula (I) according to any one of embodiments 1) to 42), or pharmaceutically acceptable salts thereof, are suitable for the prevention or treatment of obstructive diseases of the airways. Obstructive diseases of the airways include asthma, including bronchial, allergic, intrinsic, and extrinsic asthma, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; and acute viral infection including the common cold, and infection due to respiratory syncytial virus, influenza, coronavirus (including SARS) and adenovirus.

Further, the compounds of formula (I) according to any one of embodiments 1) to 42), or pharmaceutically acceptable salts thereof, are suitable for the prevention or treatment of cardiovascular diseases. Cardiovascular diseases include atherosclerosis, affecting the coronary and peripheral circulation; pericarditis; myocarditis; inflammatory and autoimmune cardiomyopathies including myocardial sarcoid; ischaemic reperfusion injuries;

endocarditis, valvulitis, and aortitis including infective (for example syphilitic); vasculitides; and disorders of the proximal and peripheral veins including phlebitis and thrombosis, including deep vein thrombosis and complications of varicose veins.

Further, the compounds of formula (I) according to any one of embodiments 1) to 42), or pharmaceutically acceptable salts thereof, are suitable for the prevention or treatment of eye diseases. Eye diseases include blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; and infections of the eyes including viral, fungal, and bacterial infections.

Further, the compounds of formula (I) according to any one of embodiments 1) to 42), or pharmaceutically acceptable salts thereof, are suitable for the prevention or treatment of skin diseases. Skin diseases include psoriasis, skin burn, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; and drug-induced disorders including fixed drug eruptions.

Further, the compounds of formula (I) according to any one of embodiments 1) to 42), or pharmaceutically acceptable salts thereof, are suitable for the prevention or treatment of abdominal and gastrointestinal tract diseases. Abdominal and gastrointestinal tract diseases include hepatitis, including autoimmune, alcoholic and viral hepatitis; fibrosis and cirrhosis of the liver; cholecystitis; pancreatitis, both acute and chronic; non-inflammatory diarrhea; glossitis, gingivitis, periodontitis; oesophagitis, including reflux; eosinophilic gastro-enteritis, mastocytosis, Crohn's disease, colitis including ulcerative colitis, proctitis, pruritis ani; Coeliac disease, irritable bowel disease/syndrome, and food-related allergies which may have effects remote from the gut, for example migraine, rhinitis or eczema; allograft rejection including acute and chronic allograft rejection following, for example, transplantation of kidney, heart, liver, lung, bone marrow, skin or cornea or following blood transfusion; and chronic graft versus host disease;

Further, the compounds of formula (I) according to any one of embodiments 1) to 42), or pharmaceutically acceptable salts thereof, are suitable for the prevention or treatment of genitourinary diseases. Genitourinary diseases include nephritis including interstitial and glomerulonephritis; nephrotic syndrome; cystitis including acute and chronic (interstitial) cystitis and Hunner's ulcer; acute and chronic urethritis, hemorrhagic cystitis, prostatitis, epididymitis, oophoritis and salpingitis; vulvovaginitis; Peyronie's disease; and erectile dysfunction, both male and female.

Further, the compounds of formula (I) according to any one of embodiments 1) to 42), or pharmaceutically acceptable salts thereof, are suitable for the prevention or treatment of cancer. The treatment of cancer includes the treatment of brain tumors, prostate, lung, breast, ovarian, bowel and colon, stomach, pancreatic, skin and bone marrow (including leukaemias) and lymphoproliferative systems, such as non-Hodgkin's and Hodgkin's lymphoma; including the prevention and treatment of metastatic disease and tumor recurrences, and paraneoplastic syndromes.

Further, the compounds of formula (I) according to any one of embodiments 1) to 42), or pharmaceutically acceptable salts thereof, are suitable for the prevention or treatment of other auto-immune and allergic disorders. Other auto-immune and allergic disorders include Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Further, the compounds of formula (I) according to any one of embodiments 1) to 42), or pharmaceutically acceptable salts thereof, are suitable for the prevention or treatment of other disorders with an inflammatory or immunological component. Other disorders with an inflammatory or immunological component include acquired immune deficiency syndrome (AIDS), leprosy, Sezary syndrome, and paraneoplastic syndromes.

Further, the compounds of formula (I) according to any one of embodiments 1) to 42), or pharmaceutically acceptable salts thereof, are suitable for the prevention or treatment of mood, depression, sleep and anxiety disorders.

Further, the compounds of formula (I) according to any one of embodiments 1) to 42), or pharmaceutically acceptable salts thereof, are suitable for the prevention or treatment of injury induced trauma and spinal cord injury.

Especially, compounds of formula (I) according to any one of embodiments 1) to 42), or pharmaceutically acceptable salts thereof, are suitable for the prevention or treatment of diseases selected from one, several or all of the following groups of diseases and disorders:

1) Pain, wherein pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);

Chronic articular pain conditions include especially rheumatoid arthritis, osteoarthritis, rheumatoid spondylitis, gouty arthritis and juvenile arthritis; Pain associated with functional bowel disorders includes especially non-ulcer dyspepsia, non-cardiac chest pain and irritable bowel syndrome;

2) Neurodegenerative and neuro-inflammatory diseases such as Alzheimer's disease and other dementing disorders including, but not limited to, Creutzfeldt-Jakob disease (CJD) and new variant Creutzfeldt-Jakob disease (nvCJD); amyloidosis; Amyotrophic lateral sclerosis, multiple sclerosis and other demyelinating syndromes; cerebral atherosclerosis and vasculitis; temporal arteritis; myasthenia gravis; Huntington's disease; Lewy Body dementia; and Parkinson's disease;

3) Bone and joint diseases such as arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Muckle-Wells syndrome, and Familial Hibernian Fever, Kikuchi disease; and drug-induced arthalgias, tendonitis, and myopathies;

4) Obstructive diseases of the airways such as chronic obstructive pulmonary disease (COPD); cystic fibrosis; lung emphysema; sarcoidosis; farmer's lung and related diseases; lung fibrosis, including fibrosis complicating tuberculosis; and chronic cough associated with inflammatory and secretory conditions of the airways;

5) Cardiovascular diseases such as inflammatory and auto-immune cardio-myopathies;

6) Eye diseases such as degenerative or inflammatory disorders affecting the retina;

7) Skin diseases such as psoriasis, skin burn, atopic dermatitis, contact dermatitis or other eczematous dermatoses; and discoid lupus erythematosus;

8) Abdominal and gastrointestinal tract diseases such as fibrosis and cirrhosis of the liver; cholecystitis; pancreatitis, both acute and chronic; Crohn's disease; colitis including ulcerative colitis; and irritable bowel disease/syndrome;

9) Genitourinary diseases such as nephritis including interstitial and glomerulonephritis; nephrotic syndrome; and cystitis including acute and chronic (interstitial) cystitis; and 10) Other auto-immune and allergic disorders such as Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Most preferably, compounds of formula (I) according to any one of embodiments 1) to 42), or pharmaceutically acceptable salts thereof, are suitable for the prevention or treatment of diseases selected from one, several or all of the following groups of diseases and disorders:

1) Pain, wherein pain refers to acute pain; chronic pain; pain associated with sprains and strains; chronic articular pain; pain associated with rheumatic fever; musculoskeletal pain (preferred); lower back and neck pain; inflammatory pain; neuropathic pain (preferred); visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);

Chronic articular pain conditions include especially rheumatoid arthritis, osteoarthritis, rheumatoid spondylitis, gouty arthritis and juvenile arthritis; Pain associated with functional bowel disorders includes especially non-ulcer dyspepsia, non-cardiac chest pain and irritable bowel syndrome;

2) Rheumatoid arthritis and osteoarthritis;
3) Chronic obstructive pulmonary disease (COPD); and
4) Crohn's disease.

The invention also relates to the use of a compound of formula (I) according to any one of embodiments 1) to 42) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 42).

A pharmaceutical composition according to the present invention contains at least one compound of formula (I) according to any one of embodiments 1) to 42) (or a pharmaceutically acceptable salt thereof) as the active agent and optionally carriers and/or diluents and/or adjuvants.

The compounds of formula (I) according to any one of embodiments 1) to 42) and their pharmaceutically acceptable salts can be used as medicaments, e.g. in the form of pharmaceutical compositions for enteral (such as especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 42), or a pharmaceutically acceptable salt thereof.

Any reference to a compound of formula (I), $(I_{St1})$, $(I_{HET})$ or $(I_{OH})$, in this text is to be understood as referring also to the salts (and especially the pharmaceutically acceptable salts) of such compounds, as appropriate and expedient. The preferences indicated for the compounds of formula (I) of course apply mutatis mutandis to the compounds of formula $(I_{St1})$, of formula $(I_{HET})$ and of formula $(I_{OH})$ as well as to the salts and pharmaceutically acceptable salts of the compounds of formula (I), of formula $(I_{St1})$, of formula $(I_{HET})$ and of formula $(I_{OH})$. The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (RT) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups $R^1$, $R^2$, $R^3$, $R^4$, $R^5$, $R^6$, $R^7$, $R^8$, $R^9$, $R^{10}$, $R^{11}$ and n are as defined for formula (I). Other abbreviations used are defined in the experimental section.

In some instances the generic groups $R^1$, $R^2$, $R^3$, $R^4$, $R^5$, $R^6$, $R^7$, $R^8$, $R^9$, $R^{10}$, $R^{11}$ and n might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

Preparation of Compounds of Formula (I)

Compounds of formula (I) can be prepared (Scheme 1) by reaction of carboxylic acids of formula II with amines of formula III using standard amide coupling reagents such as TBTU, EDC.HCl/HOBt, HATU or PyBOP in the presence of a suitable base such as DIPEA or $Et_3N$ and in a suitable solvent such as DCM, THF or DMF preferably at temperatures between RT and 45° C.

Compounds of formula (I) wherein $R^6$ represents —CH(OH)Me can be prepared by reduction of compounds of formula (I) wherein $R^6$ represents acetyl using a suitable reducing reagent such as $NaBH_4$ in a suitable solvent such as MeOH at temperatures around RT. Other primary or secondary alcohols may be prepared in analogy.

Compounds of formula (I) wherein $R^6$ represents —C(OH)Me$_2$ can be prepared from compounds of formula (I) wherein $R^6$ represents acetyl by addition of a methylmagnesium halide solution in the presence of a suitable solvent such as THF at temperatures between −10° C. and RT. Other tertiary alcohols may be prepared in analogy.

Compounds of formula (I) wherein $R^6$ represents hydroxy-($C_2$-$C_4$)alkoxy can be prepared from compounds of formula (I) wherein $R^6$ represents tert-butyloxy-($C_2$-$C_4$) alkoxy by treatment with a suitable acid such as TFA in a suitable solvent such as DCM at temperatures around RT.

Scheme 1: General synthesis of compounds of formula (I)

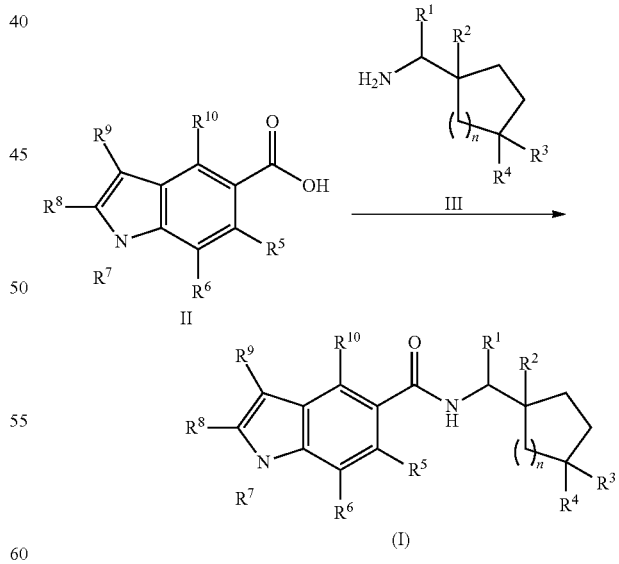

Compounds of formula Ia wherein m represents 0, 1 or 2 (Scheme 2) can be prepared as described in Scheme 1.

Alcohol derivatives of formula Ib wherein m represents 0, 1 or 2 and $R^9$ represents hydrogen, ($C_1$-$C_4$)alkyl, ($C_1$-$C_4$) alkylthio or halogen (Scheme 2) can be prepared by reduction of methyl esters of formula Ia wherein m represents 0, 1 or 2 and $R^9$ represents hydrogen, $(C_1-C_4)$alkyl, $(C_1-C_4)$alkylthio or halogen using a suitable reducing reagent such as lithium aluminum hydride, lithium borohydride or diisobutylaluminum hydride in a suitable solvent such as THF at temperatures between 0° C. and RT.

Amides of formula Ic wherein $R^{12}$ represents hydrogen or $(C_1-C_4)$alkyl (Scheme 2) can be prepared following a two step procedure: (i) hydrolysis of methyl esters of formula Ia, wherein m represents 0, by treatment with a suitable base such as LiOH, NaOH or KOH in the presence of water and a suitable organic solvent such as MeOH, EtOH or THF at temperatures around RT and (ii) coupling of the obtained acid with amines of formula $R^{12}NH_2$ using amide coupling conditions such as those previously described for the synthesis of compounds of formula (I).

Nitriles of formula Id (Scheme 2) can be prepared by dehydration of primary amides of formula Ic, wherein $R^{12}$ represents hydrogen, using a suitable dehydrating reagent such as Burgess reagent in a suitable solvent such as DCM at temperatures between RT and 50° C.

such as $NaBH(OAc)_3$, $NaBH_3CN$ or $NaBH_4$ and carrying out the reaction in a suitable solvent such as dichloroethane or a mixture of solvents such as DCM/MeOH/AcOH at temperatures around RT.

Compounds of formula Ij wherein $R^{13}$ represents $(C_1-C_4)$alkyl (Scheme 3) can be prepared by acylation of amines of formula If by treatment with a suitable acid chloride of formula $R^{13}COCl$ or an acid anhydride of formula $(R^{13}CO)_2O$ in the presence of a suitable base such as $Et_3N$ or DIPEA and in a suitable solvent such as DCM or THF at temperatures between 0° C. and 50° C.

Compounds of formula Ik wherein $R^{13}$ represents $(C_2-C_4)$alkyl (Scheme 3) can be prepared by alkoxycarbonylation of amines of formula If by treatment with a suitable alkyl chloroformate of formula $R^{13}OCOCl$ in the presence of a suitable base such as $Et_3N$ or DIPEA and in a suitable solvent such as DCM or THF at temperatures between 0° C. and 50° C.

Compounds of formula Ih wherein $R^{13}$ represents $(C_1-C_4)$alkyl or $(C_1-C_4)$alkoxy-carbonyl-$(C_1-C_4)$alkyl (Scheme Scheme 2: Synthesis of compounds of formula Ib, Ic and Id

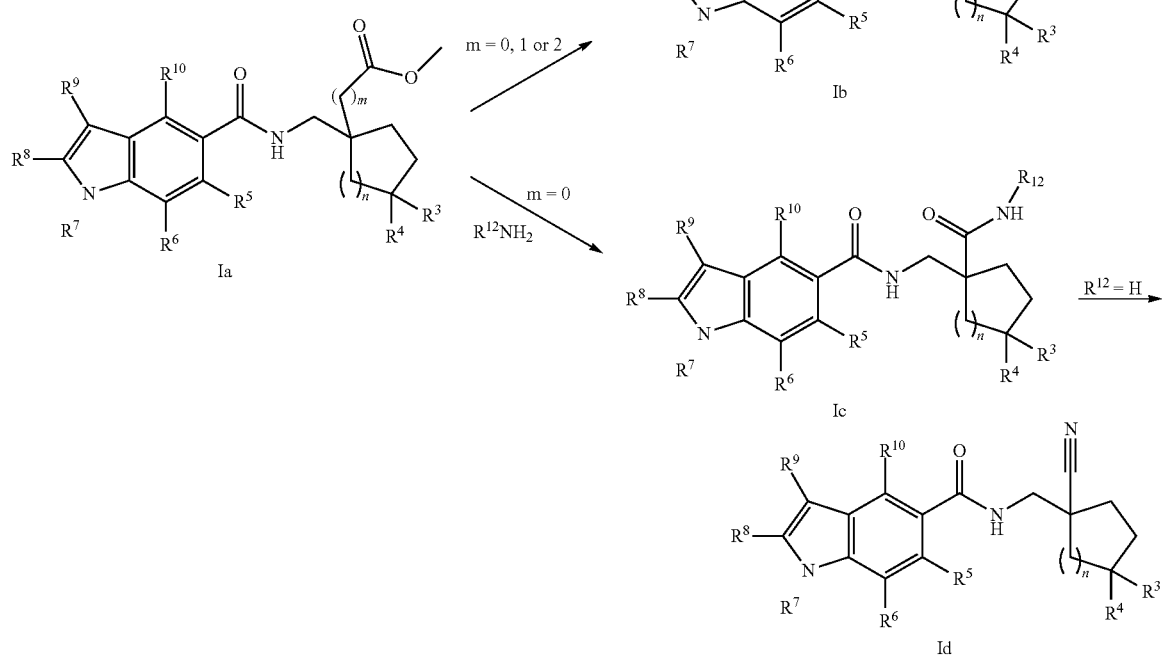

Compounds of formula Ie (Scheme 3) can be prepared as described in Scheme 1.

Compounds of formula If (Scheme 3) can be prepared by cleavage of the Boc protecting group in compounds of formula Ie by treatment with a suitable acid such as HCl or TFA in the presence of a suitable solvent such as dioxane, EtOAc or DCM at temperatures around RT.

Compounds of formula Ig (or Ii, respectively) (Scheme 3) can be prepared by reductive alkylation of amines of formula If with benzaldehyde (or an excess of formaldehyde, respectively) in the presence of a suitable reducing agent 3) can be prepared by sulfonation of amines of formula If by treatment with a suitable alkyl sulfonyl chloride of formula $R^{13}SO_2Cl$ in the presence of a suitable base such as $Et_3N$ or DIPEA and in a suitable solvent such as DCM or THF at temperatures between 0° C. and 50° C. Compounds of formula Ih wherein $R^{13}$ represents hydroxy-$(C_1-C_4)$alkyl can be prepared by reduction of compounds of formula Ih wherein $R^{13}$ represents $(C_1-C_4)$alkoxy-carbonyl-$(C_1-C_4)$alkyl using conditions such as those previously described for the synthesis of compounds of formula Ib from compounds of formula Ia.

Scheme 3: Synthesis of compounds of formula If to Ik

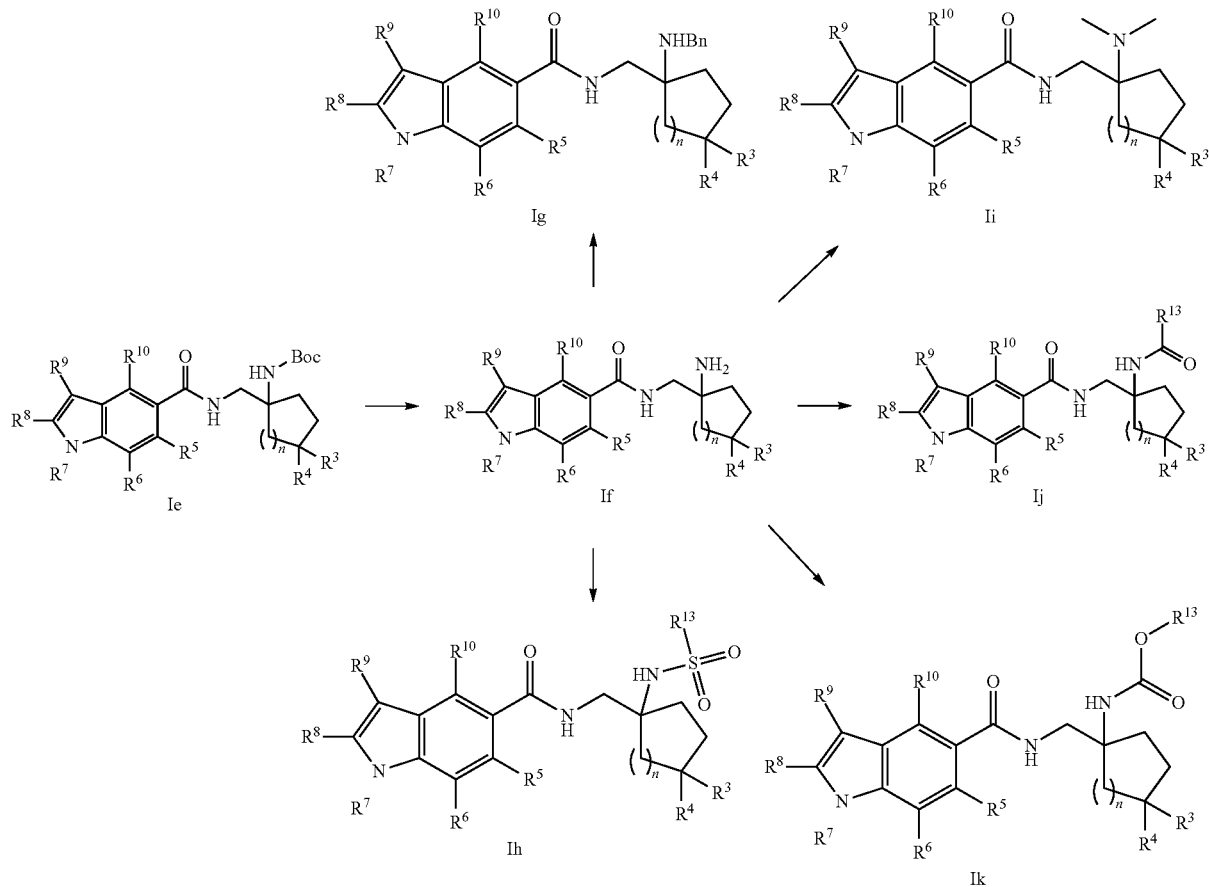

Compounds of formula Im and Io (Scheme 4) can be prepared as described in Scheme 1. Oxindoles of formula In (Scheme 4) can be prepared by oxidation of indole derivatives of formula Im with for instance pyridinium tribromide in a suitable solvent such as tert.-butanol at temperatures around RT and subsequent reduction of intermediate isatin derivatives with for instance zinc dust in a suitable solvent such as acetic acid at temperatures around RT.

Compounds of formula Ip (Scheme 4) can be prepared by reduction of nitro derivatives of formula Io with for instance tin(II) chloride dihydrate in a suitable solvent such as aq. HCl at temperatures between 0° C. and RT.

Scheme 3: Synthesis of compounds of formula In and Ip

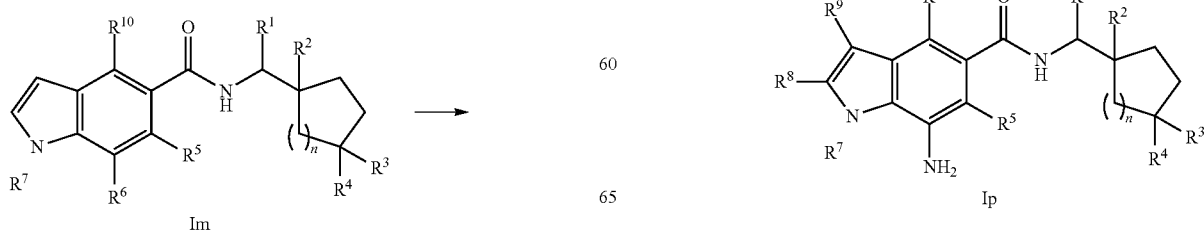

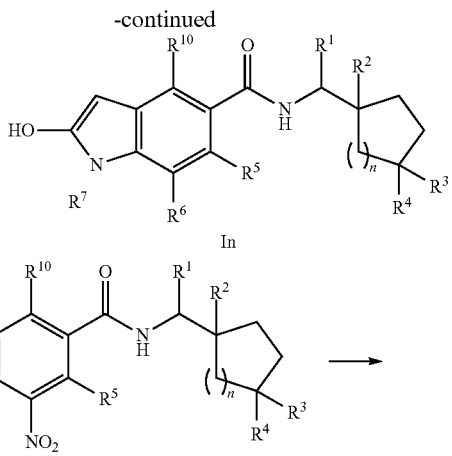

Indole carboxylic acids of formula IIa can be prepared according to the synthetic routes given in scheme 5.

Regioisomer of formula XII wherein Y represents methoxycarbonyl or cyano, together with various amounts of regioisomer XI, (Scheme 5) can be prepared by iodination of anilines of formula XIV wherein Y represents methoxycarbonyl or cyano, using 1.05 equivalents of a suitable iodinating reagent such as iodine in the presence of a catalyst such as silver sulfate and in a suitable solvent such as EtOH at temperatures around RT. The separation of both regioisomers can be achieved by column chromatography.

Compounds of formula IX wherein $R^6$ represents hydrogen and Y represents methoxycarbonyl or cyano (Scheme 5) can be prepared by Sonogashira type cross-coupling of iodides of formula XI wherein Y represents methoxycarbonyl or cyano with trimethylsilylacetylene in the presence of a suitable palladium catalyst such as bis(triphenylphosphine)palladium(II) dichloride, in the presence of a suitable copper catalyst such as copper iodide, in the presence of a ligand such as triphenylphosphine, in the presence of a suitable base such as $Et_3N$ and heating in a suitable solvent such as toluene at temperatures between 50° C. and 100° C.

Alternatively, compounds of formula IX wherein $R^6$ represents $(C_1-C_4)$alkyl, $(C_1-C_4)$alkoxy, $(C_1-C_2)$alkoxy-$(C_1-C_4)$alkyl, nitro, chloro or fluoro and Y represents methoxycarbonyl or cyano (Scheme 5) can be prepared from iodides of formula VII wherein $R^6$ represents $(C_1-C_4)$alkyl, $(C_1-C_4)$alkoxy, $(C_1-C_2)$alkoxy-$(C_1-C_4)$alkyl, nitro, chloro or fluoro and Y represents methoxycarbonyl or cyano using Sonogashira cross-coupling conditions such as those described above. Compounds of formula VII wherein $R^6$ represents $(C_1-C_4)$alkyl, $(C_1-C_4)$alkoxy, $(C_1-C_2)$alkoxy-$(C_1-C_4)$alkyl, nitro, chloro or fluoro and Y represents methoxycarbonyl or cyano (Scheme 5) can be prepared by iodination of anilines of formula VIII wherein $R^6$ represents $(C_1-C_4)$alkyl, $(C_1-C_4)$alkoxy, $(C_1-C_2)$alkoxy-$(C_1-C_4)$alkyl, nitro, chloro or fluoro and Y represents methoxycarbonyl or cyano following standard iodination conditions such as those previously described for the synthesis of compounds of formula XI and XII. Compounds of formula VIII wherein $R^6$ represents $(C_1-C_4)$alkyl or $(C_1-C_2)$alkoxy-$(C_1-C_4)$alkyl and Y represents methoxycarbonyl or cyano (Scheme 5) can be prepared by Negishi type cross-coupling of iodides of formula XII wherein Y represents methoxycarbonyl or cyano with organozinc reagents of type $R^6ZnX$ wherein $R^6$ represents $(C_1-C_4)$alkyl or $(C_1-C_2)$alkoxy-$(C_1-C_4)$alkyl and X represents chloro, bromo or $(C_1-C_4)$alkyl, in the presence of a suitable palladium catalyst such as $Pd(dppf)Cl_2.DCM$ and heating in a suitable solvent such as dioxane at temperatures between 50° C. and 100° C. Alternatively, compounds of formula VIII wherein $R^6$ represents $(C_1-C_4)$alkyl or $(C_1-C_2)$alkoxy-$(C_1-C_4)$alkyl and Y represents methoxycarbonyl or cyano (Scheme 5) can be prepared by Suzuki type cross-coupling of iodides of formula XII wherein Y represents methoxycarbonyl or cyano with boronic acid reagents of type $R^6B(OH)_2$ wherein $R^6$ represents $(C_1-C_4)$alkyl or $(C_1-C_2)$alkoxy-$(C_1-C_4)$alkyl in the presence of a suitable palladium catalyst such as bis(triphenylphosphine)palladium(II) dichloride and a base such as $K_3PO_4$ and heating in a suitable solvent such as a mixture of toluene/water 20/1 at temperatures around 110° C. Alternatively, compounds of formula VIII wherein $R^6$ represents $(C_1-C_2)$alkoxy-$(C_2-C_4)$alkyl and Y represents methoxycarbonyl (Scheme 5) can be prepared by a two step procedure: (i) Suzuki type cross-coupling of iodides of formula XII wherein Y represents methoxycarbonyl with $(C_1-C_2)$alkoxy-vinyl boronic acid pinacol ester or $(C_1-C_2)$alkoxy-$(C_1-C_2)$alkyl-vinyl boronic acid pinacol ester reagents in the presence of a suitable palladium catalyst such as $Pd(OAc)_2$, a suitable ligand such as 2-dicyclohexylphosphino-2',6'-dimethoxybiphenyl and a base such as KOH and heating in a suitable solvent such as $CH_3CN$ at temperatures around 70° C. and (ii) reduction of the double bond under hydrogenation conditions in the presence of a suitable catalyst such as $PtO_2$ and a suitable solvent such as EtOH at temperatures around RT.

Alternatively, compounds of formula VIII wherein $R^6$ represents $(C_3-C_4)$alkyl or $(C_1-C_2)$alkoxy-$(C_3-C_4)$alkyl and Y represents methoxycarbonyl or cyano (Scheme 5) can be prepared by Sonogashira type cross-coupling of iodides of formula XII wherein Y represents methoxycarbonyl or cyano with $(C_1-C_2)$alkylacetylene or $(C_1-C_2)$alkoxy-$(C_1-C_2)$alkylacetylene in the presence of a suitable palladium catalyst such as bis(triphenylphosphine)palladium(II) dichloride, in the presence of a suitable copper catalyst such as copper iodide, in the presence of a suitable base such as $Et_3N$ and heating in a suitable solvent such as THF at temperatures between RT and 80° C. The subsequent reduction of the triple bond can be carried out under hydrogenation conditions in the presence of a suitable catalyst such as $PtO_2$ and a suitable solvent such as EtOH at temperatures around RT. Alternatively, when using $(C_1-C_2)$alkylacetylene as reagent, the subsequent hydration of the triple bond can be carried out by treatment with an acid such as p-toluenesulfonic acid in the presence of a suitable solvent such as toluene at temperatures around 80° C. and leads to compounds of formula VIII wherein $R^6$ represents $(C_2-C_4)$alkylcarbonyl and Y represents methoxycarbonyl or cyano. Alternatively, compounds of formula VII wherein $R^6$ represents acetyl or ethyl, and Y represents methoxycarbonyl (Scheme 5) can be regioselectively prepared by Sonogashira type cross-coupling of iodides of formula XL wherein Y represents methoxycarbonyl with trimethylsilylacetylene following standard conditions such as those previously described for the synthesis of compounds of formula VIII. The subsequent reduction of the triple bond under hydrogenation conditions as those previously described for the synthesis of compounds of formula VIII delivers compounds of formula VII wherein $R^6$ represents ethyl and Y represents methoxycarbonyl. Alternatively, the subsequent hydration of the triple bond can be carried out by treatment with an acid such as p-toluenesulfonic acid in the presence of a suitable solvent such as toluene at temperatures around 80° C. and leads to compounds of formula VII wherein $R^6$ represents acetyl and Y represents methoxycarbonyl. Compounds of formula XL wherein Y represents methoxycarbonyl or cyano can be prepared by bis-iodination of anilines of formula XIV wherein Y represents methoxycarbonyl or cyano following standard iodination conditions such as those previously described for the synthesis of compounds of formula XI and XII but using 2.2 equivalents of iodinating reagent.

Compounds of formula V wherein Y represents methoxycarbonyl or cyano (Scheme 5) can be prepared by protodesilylation of compounds of formula IX wherein Y represents methoxycarbonyl or cyano with a base such as potassium carbonate in the presence of a suitable solvent such as MeOH at temperatures around RT.

Compounds of formula IV wherein Y represents methoxycarbonyl or cyano (Scheme 5) can be prepared by rhodium-catalyzed cycloisomerization of anilines of formula V wherein Y represents methoxycarbonyl or cyano in the presence of a rhodium catalyst such as chloro(1,5-cyclooctadiene)rhodium(I) dimer and a ligand such as tris(4-fluorophenylphosphine) and heating in a suitable solvent such as DMF at temperatures between 50° C. and 90° C.

Alternatively, compounds of formula IV wherein Y represents methoxycarbonyl or cyano can be prepared by copper-catalyzed cycloisomerization of anilines of formula IX wherein Y represents methoxycarbonyl or cyano using a suitable copper catalyst such as copper iodide and heating in a suitable solvent such as DMF at temperatures between 50° C. and 100° C.

Alternatively, compounds of formula IV wherein $R^6$ represents hydrogen and Y represents methoxycarbonyl can be prepared by simultaneous deiodination and desulfurization of methylsulfanyl indoles of formula XIII by treatment with a suitable catalyst such as Raney nickel in the presence of a suitable solvent such as EtOH at temperatures around RT. Alternatively, compounds of formula IV wherein $R^6$ represents $(C_1-C_4)$alkyl and Y represents methoxycarbonyl can be prepared by desulfurization of methylsulfanyl indoles of formula VI wherein $R^6$ represents $(C_1-C_4)$alkyl by treatment with a suitable catalyst such as Raney nickel in the presence of a suitable solvent such as EtOH at temperatures around RT. Compounds of formula VI (Scheme 5) wherein $R^6$ represents $(C_1-C_4)$alkyl can be prepared from compounds of formula XIII by Negishi type cross-coupling with $R^6ZnX$ following standard conditions such as those previously described for the synthesis of compounds of formula VIII. Compounds of formula XIII (Scheme 5) can be prepared by Gassman indole synthesis by consecutive treatment of anilines of formula XII with (i) a chlorinating reagent such as N-chlorosuccinimide or tert-butyl hypochlorite, with (ii) a protected aldehyde such as methylthioacetaldehyde dimethylacetal in the presence for both steps of a suitable solvent such as DCM at temperatures between −50° C. and −78° C., with (iii) a base such as $Et_3N$ in the presence of a suitable solvent such as chlorobenzene at temperatures between 80° C. and 120° C. and finally with (iv) an acid such as HCl in the presence of a solvent such as dioxane or $Et_2O$ at temperatures around RT.

Alternatively, compounds of formula IV (Scheme 5) wherein $R^5$ represents hydrogen or $(C_1-C_4)$alkyl, $R^6$ represents hydrogen, $(C_1-C_4)$alkyl, $(C_1-C_4)$alkoxy or $(C_1-C_2)$alkoxy-$(C_1-C_4)$alkyl, $R^{10}$ represents methyl (or ethyl respectively) and Y represents methoxycarbonyl or cyano can be prepared by Suzuki type cross-coupling of chlorides of formula IV wherein $R^5$ represents hydrogen or $(C_1-C_4)$alkyl, $R^6$ represents hydrogen, $(C_1-C_4)$alkyl, $(C_1-C_4)$alkoxy or $(C_1-C_2)$alkoxy-$(C_1-C_4)$alkyl, $R^{10}$ represents chloro and Y represents methoxycarbonyl or cyano with trimethylboroxine (or vinyl boronic acid pinacol ester respectively) in the presence of a suitable palladium catalyst such as [1,3-bis(2,6-diisopropylphenyl)imidazol-2-ylidene](3-chloropyridyl)palladium(II) dichloride, in the presence of a suitable base such as $K_2CO_3$ and heating in a suitable solvent such as dioxane at temperatures around 110° C. When using vinyl boronic acid pinacol ester as reagent, the subsequent reduction of the double bond was carried out under hydrogenation conditions such as those described above.

Alternatively, compounds of formula IV (Scheme 5) wherein $R^6$ represents —C(OMe)Me$_2$ and Y represents methoxycarbonyl or cyano can be prepared from ketone of formula IV wherein $R^6$ represents acetyl and Y represents methoxycarbonyl or cyano by a two step procedure: (i) addition of a methylmagnesium halide solution in the presence of a suitable solvent such as THF at temperatures around RT and (ii) alkylation with MeI in the presence of a suitable base such as a suspension of NaH in mineral oil and a suitable solvent such as THF at temperatures between 0° C. and RT. Other tertiary ethers may be prepared in analogy.

Alternatively, compounds of formula IV (Scheme 5) wherein $R^6$ represents hydroxy (or hydroxy-$(C_1-C_4)$alkyl respectively) and Y represents cyano can be prepared from methyl ether of formula IV wherein $R^6$ represents methoxy (or methoxy-$(C_1-C_4)$alkyl respectively) and Y represents cyano by treatment with $BBr_3$ in the presence of a suitable solvent such as DCM at temperatures between −78° C. and 55° C. The possible subsequent alkylation of the phenol of formula IV wherein $R^4$ represents hydroxy and Y represents cyano by treatment with $(C_1-C_4)$alkyl halide or $(C_1-C_4)$alkoxy-$(C_2-C_4)$alkyl halide in the presence of a suitable base such as $K_2CO_3$ and a suitable solvent such as DMF at temperatures between 0° C. and 80° C. provides compounds of formula IV wherein $R^6$ represents $(C_1-C_4)$alkoxy or $(C_1-C_4)$alkoxy-$(C_2-C_4)$alkoxy and Y represents cyano.

Carboxylic acid derivatives of formula IIa (Scheme 5) can be prepared by hydrolysis of methyl esters of formula IV wherein Y represents methoxycarbonyl by standard treatment with a suitable base such as LiOH, NaOH or KOH in the presence of water and a suitable organic solvent such as MeOH, EtOH or THF at temperatures between RT and 60° C. Alternatively, carboxylic acid derivatives of formula IIa (Scheme 5) can be prepared by hydrolysis of nitriles of formula IV wherein Y represents cyano with a suitable base such as KOH or NaOH in the presence of water and optionally a suitable organic solvent such as 2-propanol at temperatures around 150° C.

Scheme 5: Synthesis of carboxylic acid intermediates of formula II wherein $R^8$ represents hydrogen

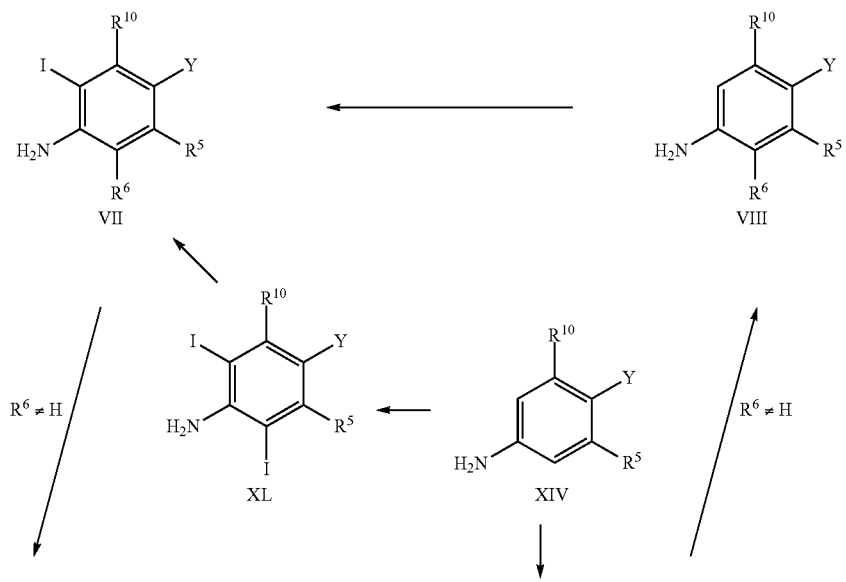

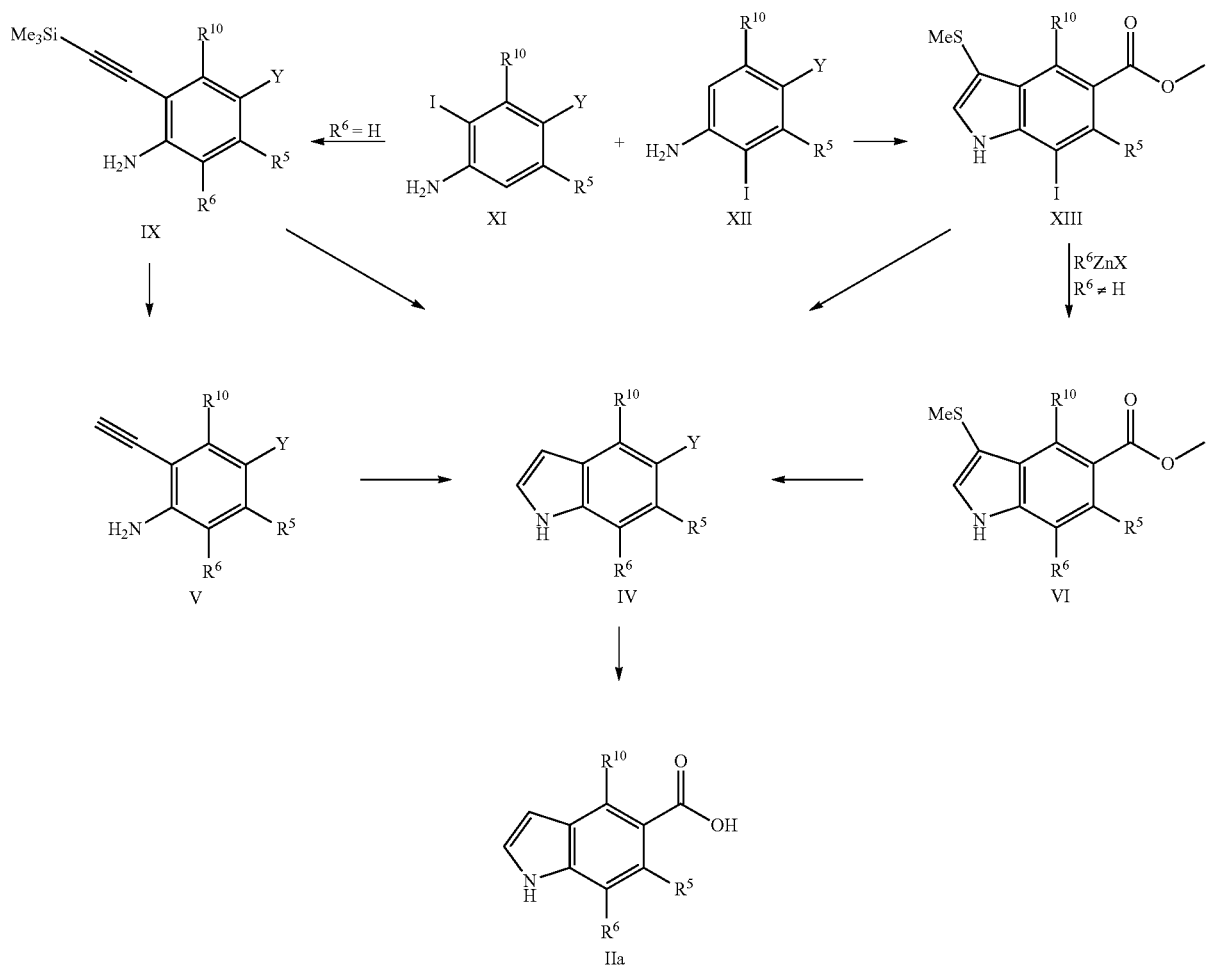

Indole carboxylic acids of formula IIb can be prepared according to the synthetic routes given in scheme 6.

Hydrazines of formula XVII (Scheme 6) can be prepared by diazotisation of anilines of formula XII wherein $R^{10}$ represents chloro with for instance sodium nitrite in a suitable solvent such as aq. HCl at temperatures around 0° C. and subsequent reduction of the diazonium salt with for instance tin(II) chloride dihydrate in a suitable solvent such as aq. HCl at temperatures between 0° C. and RT.

Indoles of formula XVIII (Scheme 6) can be prepared by Fisher indole reaction between hydrazine derivatives of formula XVII and ketones of formula $R^8COCH_2SMe$ wherein $R^8$ represents $(C_1-C_4)$alkyl in the presence of a suitable acid such as HCl and a suitable solvent such as EtOH at temperatures between 50° C. and 80° C.

Compounds of formula XVI wherein $R^5$ represents hydrogen, $(C_1-C_4)$alkyl or chloro and $R^6$ represents $(C_1-C_4)$alkyl, $(C_1-C_2)$alkoxy-$(C_1-C_4)$alkyl or $(C_1-C_4)$alkyl-carbonyl (Scheme 6) can be prepared from iodides of formula XVIII by Negishi, Sonogashira or Suzuki type cross-coupling reaction following standard conditions such as those previously described for the synthesis of compounds of formula VIII. The possible subsequent reduction or hydration step can be carried out as previously described for the synthesis of compounds of formula VIII.

Alternatively, compounds of formula XVI (Scheme 6) can be prepared from anilines of formula VIII wherein Y represents methoxycarbonyl by a similar two-step sequence (hydrazine formation and Fisher indole synthesis) using similar conditions such as those previously described for the synthesis of compounds of formula XVIII from compounds of formula XII.

Compounds of formula XV wherein $R^6$ represents fluoro, chloro, $(C_1-C_4)$alkyl, $(C_1-C_4)$alkoxy, $(C_1-C_4)$alkyl-carbonyl, $(C_1-C_2)$alkoxy-$(C_1-C_4)$alkyl or $(C_1-C_4)$alkoxy-$(C_2-C_4)$alkoxy (Scheme 6) can be prepared by desulfurization of compounds of formula XVI following conditions such as those previously described for the synthesis of compounds of formula IV from compounds of formula VI.

Alternatively, compounds of formula XV wherein $R^6$ represents hydrogen can be prepared from compounds of formula XVIII by simultaneous deiodination and desulfurization following conditions such as those previously described for the synthesis of compounds of formula IV from compounds of formula XIII.

Carboxylic acid derivatives of formula IIb wherein $R^8$ represents $(C_1-C_4)$alkyl (Scheme 6) can be prepared by hydrolysis of methyl esters of formula XV following conditions such as those previously described for the synthesis of compounds of formula IIa.

Scheme 6: Synthesis of carboxylic acid intermediates of formula II wherein $R^8$ represents $(C_1-C_4)$alkyl

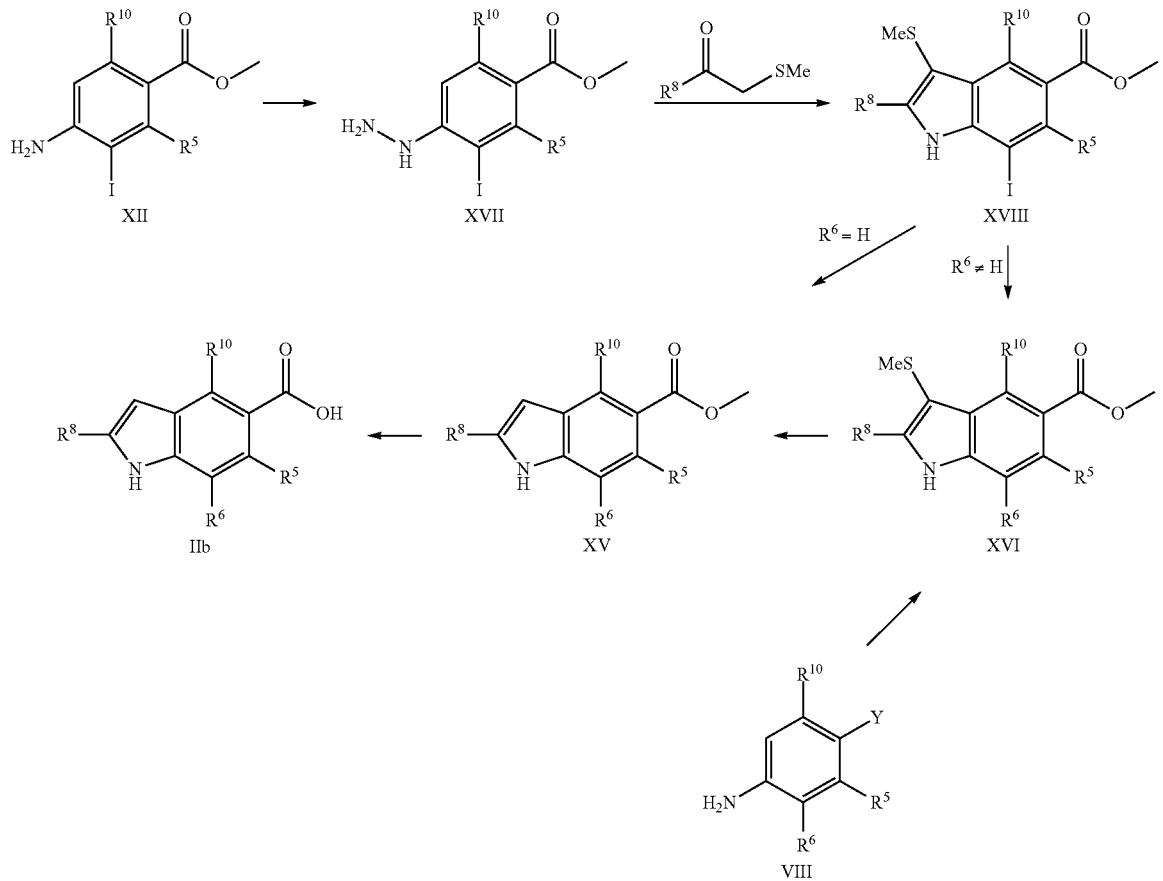

Indole carboxylic acids of formula IIc wherein $R^9$ represents $(C_1-C_4)$alkyl, formyl or halogen (Scheme 7) can be prepared according to procedures well known in the art for the introduction of substituents at the 3-position of indoles. Representative synthetic routes are depicted below and outlined in scheme 7.

Indole derivatives of formula A wherein $R^9$ represents formyl (Scheme 7) can be prepared from indole derivatives of formula IV wherein Y represents methoxycarbonyl by Vilsmeier-Haack reaction with phosphorus oxychloride and DMF at temperatures between 0° C. and 40° C. Resulting formylated indole derivatives can be transformed to indole derivatives of formula A wherein $R^9$ represents methyl (Scheme 7) following a two-step one-pot procedure: (i) formation of tosyl hydrazone by condensation with p-toluenesulfonyl hydrazide in the presence of p-toluene sulfonic acid, sulfolane and a suitable solvent such as DMF at temperatures around 100° C. and (ii) consecutive reduction of resulting tosyl hydrazone with for instance sodium borohydride at temperatures around 100° C.

Indole derivatives of formula A wherein $R^9$ represents chloro (or bromo, respectively) (Scheme 7) can be prepared by chlorination (or bromination, respectively) of indole derivatives of formula IV wherein Y represents methoxycarbonyl with a suitable halogenating reagent such as NCS (or NBS, respectively) in the presence of a suitable solvent such as DMF or $CH_2Cl_2$ at temperatures between 0° C. and RT.

Indole derivatives of formula A wherein $R^9$ represents fluoro (Scheme 7) can be prepared by fluorination of indole derivatives of formula IV wherein Y represents methoxycarbonyl with a suitable fluorinating reagent such as 1-fluoro-2,4,6-trimethylpyridinium triflate in the presence of a suitable solvent such as MeOH at temperatures around 65° C.

Carboxylic acid derivatives of formula IIc (Scheme 7) can be prepared by hydrolysis of methyl esters of formula A following conditions such as those previously described for the synthesis of compounds of formula IIa.

Indole derivatives of formula B wherein $R^7$ represents $(C_1-C_3)$alkyl (Scheme 7) can be prepared by alkylation of indole derivatives of formula IV, XV or A with a suitable alkylating reagent such as $R^7$Br or $R^7$I wherein $R^7$ represents $(C_1-C_3)$alkyl and a suitable base such as NaH in the presence of a suitable solvent such as DMF at temperatures between 0° C. and RT.

Carboxylic acid derivatives of formula IId (Scheme 7) can be prepared by hydrolysis of methyl esters of formula B following conditions such as those previously described for the synthesis of compounds of formula IIa.

Scheme 7: Synthesis of carboxylic acid intermediates of formula IIc wherein $R^9$ represents $(C_1$-$C_4)$alkyl, formyl and halogen and of intermediates of formula IId wherein $R^7$ represents $(C_1$-$C_4)$alkyl

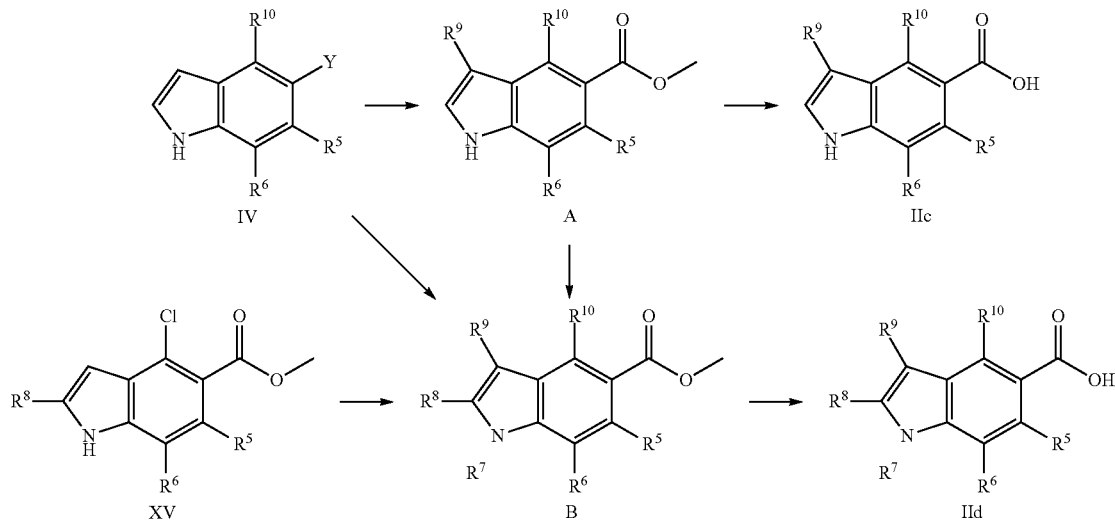

If not commercially available, aniline intermediates of formula XIV wherein Y represents methoxycarbonyl or cyano can be prepared according to procedures known in the art. Two possible synthetic routes are outlined in Scheme 8 below, which also illustrate alternative synthetic accesses to compounds of formula VIII wherein Y represents methoxycarbonyl or cyano.

Carboxylic acid derivatives of formula XX wherein $R^5$ represents hydrogen or halogen, $R^6$ represents hydrogen, $(C_1$-$C_4)$alkoxy or halogen and $R^{10}$ represents fluoro, chloro, $(C_1$-$C_2)$fluoroalkyl or methoxy (Scheme 8) can be prepared by oxidation of toluene derivatives of formula XIX wherein $R^5$ represents hydrogen or halogen, $R^6$ represents hydrogen, $(C_1$-$C_4)$alkoxy or halogen and $R^{10}$ represents fluoro, chloro, $(C_1$-$C_2)$fluoroalkyl or methoxy with a suitable oxidizing reagent such as $KMnO_4$ in the presence of water and a solvent such as pyridine at temperatures around 100° C.

Alternatively, carboxylic acid derivatives of formula XX wherein $R^6$ represents hydrogen, $(C_1$-$C_4)$alkyl, $(C_1$-$C_4)$alkoxy, $(C_1$-$C_2)$alkoxy-$(C_1$-$C_4)$alkyl, $(C_1$-$C_4)$alkoxy-$(C_2$-$C_4)$alkoxy or halogen (Scheme 8) can be prepared by hydrolysis of nitriles of formula XXIII wherein $R^6$ represents hydrogen, $(C_1$-$C_4)$alkyl, $(C_1$-$C_4)$alkoxy, $(C_1$-$C_2)$alkoxy-$(C_1$-$C_4)$alkyl, $(C_1$-$C_4)$alkoxy-$(C_2$-$C_4)$alkoxy or halogen by treatment with a suitable base such as KOH or NaOH in the presence of water and a suitable organic solvent such as 2-propanol at temperatures around 150° C. An additional treatment with sodium nitrite in the presence of water and an acid such as sulphuric acid at temperatures around 80° C. may be required for the hydrolysis of the primary amide intermediates. Nitriles of formula XXIII wherein $R^6$ represents hydrogen, $(C_1$-$C_4)$alkyl, $(C_1$-$C_4)$alkoxy, $(C_1$-$C_2)$alkoxy-$(C_1$-$C_4)$alkyl, $(C_1$-$C_4)$alkoxy-$(C_2$-$C_4)$alkoxy or halogen (Scheme 8) can be prepared by treatment of anilines of formula XXII with a suitable diazotisation reagent such as tert-butyl nitrite in the presence of a suitable cyanating reagent such as copper(I) cyanide in a suitable solvent such as $CH_3CN$ at temperatures between 0° C. and 80° C.

Alternatively, carboxylic acid derivatives of formula XX wherein $R^6$ represents $(C_1$-$C_4)$alkoxy (or $(C_1$-$C_4)$alkoxy-$(C_2$-$C_4)$alkoxy, respectively) (Scheme 8) can be prepared by nucleophilic aromatic substitution of fluorides of formula XX wherein $R^6$ represents fluoro with $(C_1$-$C_4)$-alcohol (or $(C_1$-$C_4)$alkoxy-$(C_2$-$C_4)$alcohol, respectively) in the presence of a base such as $Cs_2CO_3$ and a suitable solvent such as DMF at temperatures between RT and 110° C.

Methyl esters of formula XXI wherein $R^N$ represents nitro (Scheme 8) can be prepared by treatment of carboxylic acids of formula XX with a suitable base such as $Cs_2CO_3$ or $K_2CO_3$ and a suitable alkylating reagent such as MeI in the presence of a suitable solvent such as DMF at temperatures around RT.

Alternatively, compounds of formula XXI wherein $R^N$ represents acetylamino, $R^5$ represents hydrogen, $(C_1$-$C_4)$alkyl, fluoro or chloro, $R^6$ represents $(C_1$-$C_4)$alkyl, $(C_1$-$C_4)$alkoxy, $(C_1$-$C_2)$alkoxy-$(C_1$-$C_4)$alkyl, $(C_1$-$C_4)$alkoxy-$(C_2$-$C_4)$alkoxy, fluoro or chloro and $R^{10}$ represents methyl or ethyl (Scheme 8) can be prepared from phenols of formula XXI wherein $R^N$ represents acetylamino, $R^5$ represents hydrogen, $(C_1$-$C_4)$alkyl, fluoro or chloro, $R^6$ represents $(C_1$-$C_4)$alkyl, $(C_1$-$C_4)$alkoxy, $(C_1$-$C_2)$alkoxy-$(C_1$-$C_4)$alkyl, $(C_1$-$C_4)$alkoxy-$(C_2$-$C_4)$alkoxy, fluoro or chloro and $R^{10}$ represents hydroxy following a two-step procedure: (i) triflate formation by treatment with trifluoromethanesulfonic anhydride in the presence of a base such as $Et_3N$ and a suitable solvent such as DCM at temperatures around RT and (ii) consecutive Suzuki type cross coupling with methyl or ethyl boronic acid in the presence of a suitable palladium catalyst such as $Pd(dppf)Cl_2 \cdot DCM$ and a base such as $K_3PO_4$ and heating in a suitable solvent such as THF at temperatures around 65° C. Anilines of formula XIV wherein Y represents methoxycarbonyl (or VIII wherein $R^6$ represents $(C_1$-$C_4)$alkyl, $(C_1$-$C_4)$alkoxy, $(C_1$-$C_2)$alkoxy-$(C_1$-$C_4)$alkyl, $(C_1$-$C_4)$alkoxy-$(C_2$-$C_4)$alkoxy or halogen and Y represents methoxycarbonyl, respectively) (Scheme 8) can be prepared by reduction of nitrobenzene derivatives of formula XXI wherein $R^N$ represents nitro and $R^6$ represents hydrogen (or XXI wherein $R^N$ represents nitro and $R^6$ represents $(C_1$-$C_4)$alkyl, $(C_1$-$C_4)$alkoxy, $(C_1$-$C_2)$alkoxy-$(C_1$-$C_4)$alkyl, $(C_1$-$C_4)$alkoxy-$(C_2$-$C_4)$alkoxy or halogen, respectively) with a suitable reducing reagent such as tin(II) chloride dihydrate in the presence of a suitable solvent such as DMF at temperatures around 100° C. or with zinc dust and ammonium formate in the presence of a suitable solvent such as MeOH at temperatures around RT.

Alternatively, anilines of formula XIV wherein Y represents methoxycarbonyl (or VIII wherein $R^6$ represents $(C_1$-$C_4)$alkyl, $(C_1$-$C_4)$alkoxy, $(C_1$-$C_4)$alkyl-carbonyl, $(C_1$-$C_2)$alkoxy-$(C_1$-$C_4)$alkyl, $(C_1$-$C_4)$alkoxy-$(C_2$-$C_4)$alkoxy or halogen and Y represents methoxycarbonyl, respectively) (Scheme 8) can be prepared by methanolysis of acetylated anilines of formula XXI wherein $R^N$ represents acetylamino alkoxy-$(C_1$-$C_4)$alkyl, $(C_1$-$C_4)$alkoxy-$(C_2$-$C_4)$alkoxy or halogen and Y represents methoxycarbonyl, respectively) (Scheme 8) can be prepared by esterification of anilines of formula XIV wherein Y represents hydroxycarbonyl (or VIII wherein $R^6$ represents $(C_1$-$C_4)$alkyl, $(C_1$-$C_4)$alkoxy, $(C_1$-$C_4)$alkyl-carbonyl, $(C_1$-$C_2)$alkoxy-$(C_1$-$C_4)$alkyl, $(C_1$-$C_4)$alkoxy-$(C_2$-$C_4)$alkoxy or halogen and Y represents hydroxycarbonyl, respectively) by standard procedures as for example the treatment with acetylchloride in the presence of MeOH at temperatures around 65° C.

Scheme 8: Synthesis of aniline precursors XIV and VIII

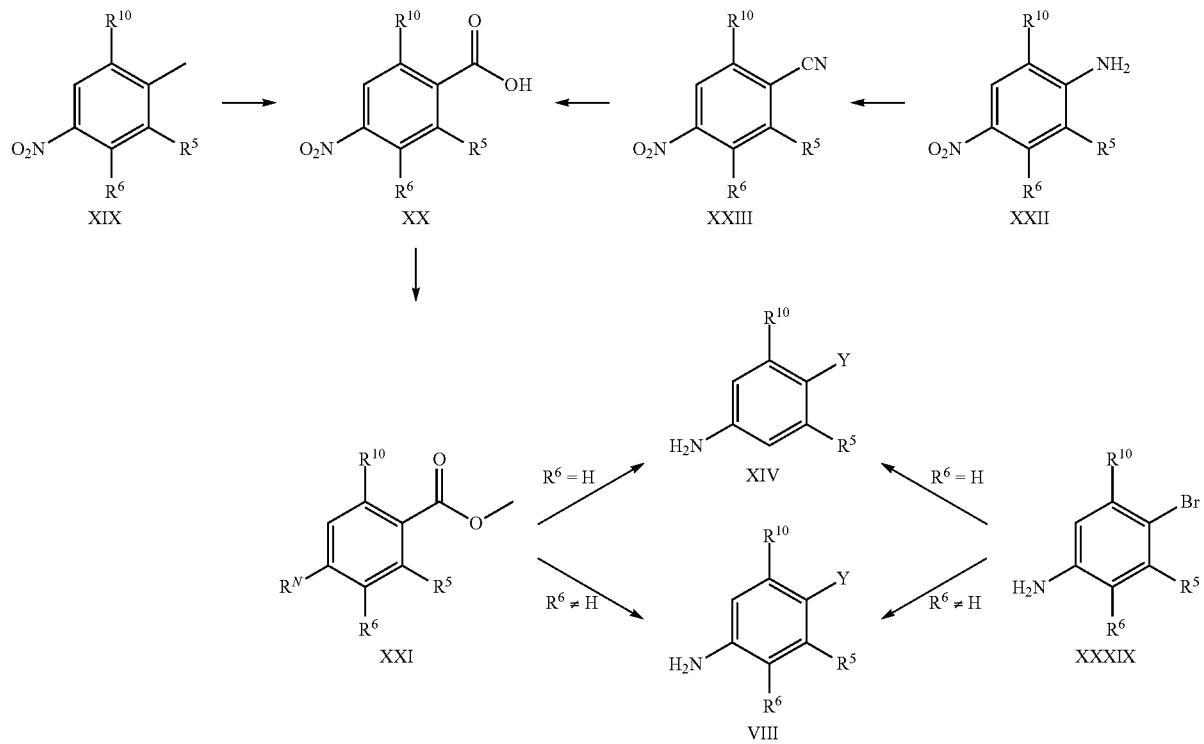

and $R^6$ represents hydrogen (or XXI wherein $R^N$ represents acetylamino and $R^6$ represents $(C_1$-$C_4)$alkyl, $(C_1$-$C_4)$alkoxy, $(C_1$-$C_4)$alkyl-carbonyl, $(C_1$-$C_2)$alkoxy-$(C_1$-$C_4)$alkyl, $(C_1$-$C_4)$alkoxy-$(C_2$-$C_4)$alkoxy or halogen, respectively) with $K_2CO_3$ in the presence of MeOH at temperatures around RT.

Alternatively, anilines of formula XIV wherein $R^5$ represents hydrogen, $(C_1$-$C_4)$alkyl, fluoro or chloro and Y represents cyano (or VIII wherein $R^6$ represents $(C_1$-$C_4)$alkyl, $(C_1$-$C_4)$alkoxy, $(C_1$-$C_4)$alkyl-carbonyl, $(C_1$-$C_2)$alkoxy-$(C_1$-$C_4)$alkyl, $(C_1$-$C_4)$alkoxy-$(C_2$-$C_4)$alkoxy, fluoro or chloro, $R^5$ represents hydrogen, $(C_1$-$C_4)$alkyl, fluoro or chloro and Y represents cyano, respectively) (Scheme 8) can be prepared by palladium catalysed cyanation of bromides of formula XXXIX wherein $R^5$ represents hydrogen, $(C_1$-$C_4)$alkyl, fluoro or chloro and $R^6$ represents hydrogen, $(C_1$-$C_4)$alkyl, $(C_1$-$C_4)$alkoxy, $(C_1$-$C_4)$alkyl-carbonyl, $(C_1$-$C_2)$alkoxy-$(C_1$-$C_4)$alkyl, $(C_1$-$C_4)$alkoxy-$(C_2$-$C_4)$alkoxy, fluoro or chloro with zinc cyanide in the presence of a suitable palladium catalyst such as $Pd(PPh_3)_4$ and heating in a suitable solvent such as DMF at temperatures around 110° C.

Alternatively, anilines of formula XIV wherein Y represents methoxycarbonyl (or VIII wherein $R^6$ represents $(C_1$-$C_4)$alkyl, $(C_1$-$C_4)$alkoxy, $(C_1$-$C_4)$alkyl-carbonyl, $(C_1$-$C_2)$ If not commercially available, amines of formula IIIa, wherein $R^{14}$ represents hydrogen or $(C_1$-$C_4)$alkyl, can be prepared following the procedures outlined in Scheme 9 below.

The compounds of formula XXVI wherein $R^{14}$ represents trimethylsilyl or hydrogen (Scheme 9) can be prepared by cyanosilylation of a ketone of formula XXIV using a suitable cyanation reagent such as trimethylsilylcyanide, in the presence of a lewis acid such as gold (III) chloride or zinc iodide in a suitable solvent such as DCM at temperatures around RT (Synthesis, 2008, 4, 507-510).

The compounds of formula XXVI wherein $R^{14}$ represents $(C_1$-$C_4)$alkyl (Scheme 9) can be prepared by cyanation of a ketal of formula XXV with a suitable cyanation reagent such as tert-butyl isocyanide in the presence of a suitable lewis acid such as titanium tetrachloride in a suitable solvent such as DCM at temperatures between −70° C. and RT (Chemistry Lett., 1984, 937-940).

The compounds of formula IIIa wherein $R^{14}$ represents hydrogen or $(C_1$-$C_4)$alkyl (Scheme 9) can be prepared by reduction of a compound of formula XXVI using a suitable reducing reagent such as lithium aluminum hydride, in the presence of a suitable solvent such as $Et_2O$ or THF at temperatures between 0° C. and RT. Under those conditions the consecutive hydrolysis of a trimethylsilyl group, if present as $R^{14}$, is observed.

Scheme 9: Synthesis of amines of formula IIIa

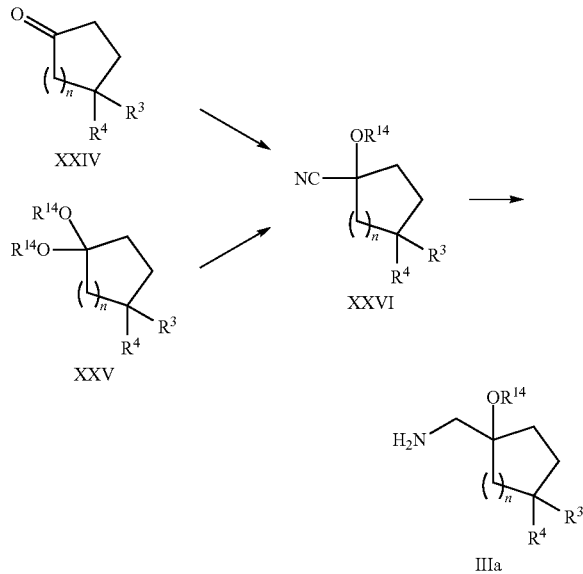

If not commercially available, amines of formula IIIb wherein $R^2$ represents aryl or heteroaryl can be prepared following the procedures outlined in Scheme 10 below.

If not commercially available, aryl- or heteroaryl-acetonitriles of formula XXVIII (Scheme 10) can be prepared by a two step procedure: (i) arylation or heteroarylation of methyl cyanoacetate by treatment with a bromoarene or bromohet-eroarene of formula Br—$R^2$ in the presence of a suitable base such as KOtBu, a suitable palladium catalyst such as Pd(OAc)$_2$, a suitable ligand such as dppf in a suitable solvent such as dioxane as described in J. Org. Chem., 2008, 73, 4, 1643-1645 and (ii) subsequent Krapcho decarboxy-lation of the isolated methyl aryl- or heteroarylcyanoacetate intermediates by treatment with a suitable source for halide anions such as LiCl in a suitable solvent such as wet DMSO at temperatures between 100° C. and 150° C.

Alternatively, if not commercially available, aryl- or heteroaryl-acetonitriles of formula XXVIII (Scheme 10) can be prepared according to J. Am. Chem. Soc., 2011, 133, 6948-6951.

Nitriles of formula XXIX (Scheme 10) can be prepared by dialkylation of aryl- or heteroaryl-acetonitriles of formula XXVIII with dihaloalkanes such as Br—(CH$_2$)$_n$—CR$^3$R$^4$—(CH$_2$)$_2$—Br wherein n represents 1, 2, 3 or 4 and R$^3$ and R$^4$ represents hydrogen or fluoro in the presence of a base such as NaH or tBuOK in a suitable organic solvent such as THF or DMSO preferably at temperatures between 0° C. and RT.

Amines of formula IIIb (Scheme 10) can be prepared by reduction of nitriles of formula XXIX for instance under hydrogenation conditions in the presence of a suitable catalyst such as Raney nickel and a suitable solvent such as methanolic ammonia at temperatures around RT or with a suitable reducing reagent such as borane tetrahydrofuran complex in a suitable solvent such as THF at temperatures around 70° C.

Amines of formula IIIb wherein n represents 2 and R$^3$ and R$^4$ represents fluoro (Scheme 10) can be prepared for instance following a 4-step sequence: (i) tandem double Michael addition-Dieckmann condensation reaction of acetonitrile derivatives of formula XXVIII with methylacrylate according to J. Org. Chem., 2007, 72, 7455-7458 (ii) Krapcho decarboxylation of intermediates of formula XXX following conditions as those already described above for the synthesis of compounds of formula XXVIII (iii) difluo-rination of ketone intermediates of formula XXXI using DAST in a suitable solvent such as DCM at temperatures between −78° C. and RT and (iv) reduction of nitriles of formula XXXII following conditions such as those already described for the synthesis of amines of formula IIIb from XXIX.

Scheme 10: Synthesis of amines of formula IIIb wherein $R^2$ represents aryl or heteroaryl

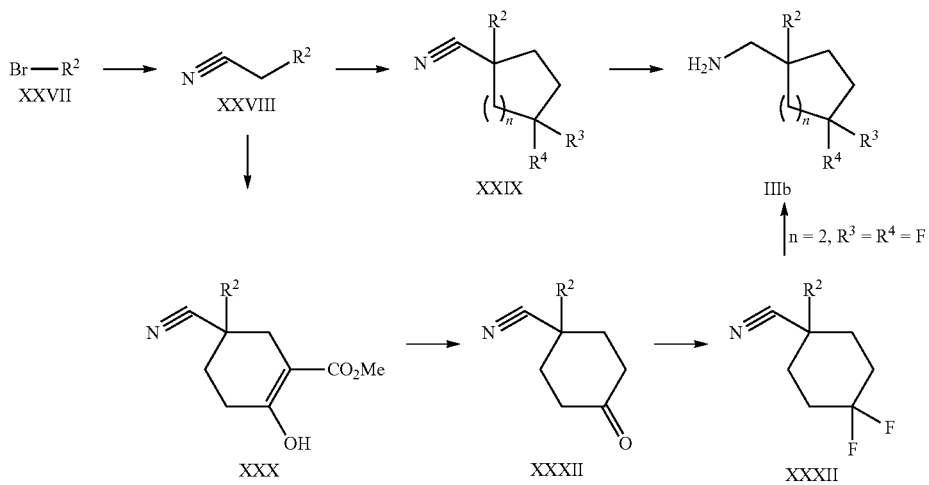

If not commercially available, amines of formula IIIc can be prepared following the procedures outlined in Scheme 11 below.

If not commercially available, amines of formula XXXIV wherein $R^{15}$ and $R^{16}$ represent hydrogen (Scheme 11) can be prepared for instance by alkylation of N-(diphenylmethylene)glycine tert-butyl ester with cycloalkyl bromide or iodide of formula XXXIII (X represents bromo or iodo) according to *Angew. Chem. Int. Ed.*, 2005, 44, 1549-1551. Subsequent reduction of resulting esters of formula XXXIV wherein $R^{15}$ and $R^{16}$ represent hydrogen using for instance lithium aluminum hydride in a suitable solvent such as THF at temperatures between 0° C. and RT gives aminoalcohols of formula IIIc wherein $R^3$ and $R^4$ represent hydrogen.

If not commercially available, amines of formula XXXIV wherein $R^{15}$ represents hydroxy and $R^{16}$ represents hydrogen or $R^{15}$ and $R^{16}$ form an ethylenedioxy group (Scheme 11) can be prepared as previously described for the synthesis of amines of formula XXXIV wherein $R^{15}$ and $R^{16}$ represent hydrogen.

If not commercially available as methyl ester ($R^{17}$ represents Me), compounds of formula XXXV wherein $R^{17}$ represents tBu and $R^{18}$ represents Boc (or Z respectively) (Scheme 11) can be prepared by treatment of amines of formula XXXIV wherein $R^{15}$ represents hydroxy and $R^{16}$ represents hydrogen with Boc-anhydride (or Z—Cl respectively) in the presence of a base such as $Et_3N$ or NaOH in a suitable solvent such as DCM or dioxane/water at temperatures between 0° C. and RT. Oxidation of resulting compounds using for instance DMP in a suitable solvent such as DCM at temperatures around RT gives ketones of formula XXXVI wherein $R^{17}$ represents tBu or Me and $R^{18}$ represents Boc or Z.

Alternatively, ketones of formula XXXVI wherein $R^{17}$ represents tBu or Me and $R^{18}$ represents Z (Scheme 11) can be prepared by a two step procedure: (i) Z-protection of amines of formula XXXIV wherein $R^{15}$ and $R^{16}$ form an ethylenedioxy group using conditions as previously described for the synthesis of compounds of formula XXXV and (ii) cleavage of the ketal protecting group using acidic conditions such as aq. HCl and a suitable organic solvent such as MeCN or THF at temperatures around RT.

If not commercially available, compounds of formula XXXVII wherein $R^{17}$ represents tBu or Me and $R^{18}$ represents Boc or Z (Scheme 11) can be prepared by fluorination of ketones of formula XXXVI wherein $R^{17}$ represents tBu or Me and $R^{18}$ represents Boc or Z using a fluorinating reagent such as DAST or bis(2-methoxyethyl)aminosulfur trifluoride in the presence of a suitable solvent such as THF or DCM at temperatures between 0° C. and RT.

Compounds of formula XXXVIII wherein $R^{18}$ represents Boc or Z (Scheme 11) can be prepared by reduction of esters of formula XXXVII wherein $R^{17}$ represents tBu or Me and $R^{18}$ represents Boc or Z following conditions such as those already described for the reduction of esters of formula XXXIV wherein $R^{15}$ and $R^{16}$ represent hydrogen. Amines of formula IIIc wherein $R^3$ and $R^4$ represent fluoro (Scheme 11) can be prepared by Boc cleavage (or Z cleavage respectively) from compounds of formula XXXVIII wherein $R^{18}$ represents Boc (or Z respectively) using a suitable acid such as HCl or TFA in the presence of a suitable solvent such as dioxane, EtOAc or DCM (or under hydrogenation conditions in the presence of a suitable catalyst such as palladium on charcoal and a suitable solvent such as MeOH or dioxane respectively) at temperatures around RT.

Scheme 11: Synthesis of amines of formula IIIc

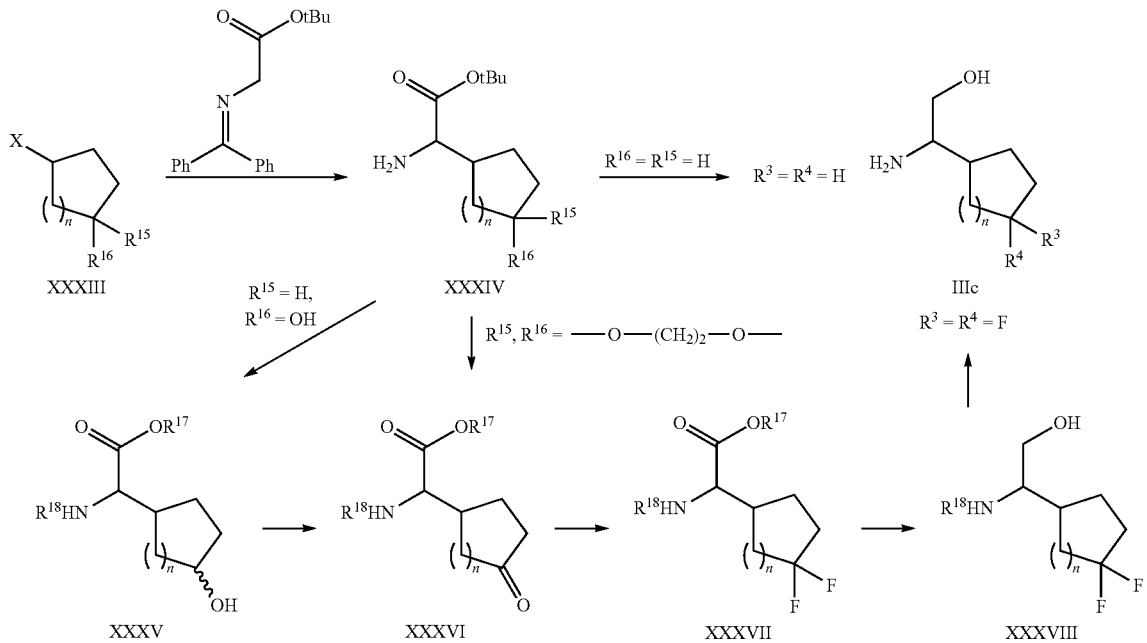

EXPERIMENTAL PART

Abbreviations

Ac acetyl
AIBN 2,2'-azobis(2-methylpropionitrile)
anh. anhydrous
aq. aqueous
ATP adenosine-5'-triphoshate
Bn benzyl
Boc tert.-butyloxycarbonyl
Burgess reagent (methoxycarbonylsulfamoyl)triethylammonium hydroxide, inner salt
tBu tert.-butyl
CC column chromatography cDNA complementary desoxyribonucleic acid
CNS central nervous system
DAST diethylaminosulfur trifluoride
DCM dichloromethane
DIPEA diisopropylethylamine
DMEM Dulbecco's modified eagle's medium
DMF dimethylformamide
DMP Dess Martin periodinane
DMSO dimethylsulfoxide
DNA desoxyribonucleic acid
dppf 1,1'-bis(diphenylphosphino)ferrocene
EDC.HCl N-(3-dimethylaminopropyl)-N'-ethylcarbodiimide hydrochloride
eq equivalent
Et ethyl
FCS fetal calf serum
FLIPR fluorescent imaging plate reader
h hour(s)
HATU 2-(7-aza-1H-benzotriazole-1-yl)-1,1,3,3-tetramethyluronium hexafluorophosphate
Hept heptanes
HOBt 1-hydroxybenzotriazole hydrate
HV high vacuum
LC-MS liquid chromatography-mass spectrometry
M molar(ity)
Me methyl
min minute(s)
MS mass spectrometry
NBS N-bromosuccinimide
NCS N-chlorosuccinimide
NMR nuclear magnetic resonance
ON overnight
PBS phosphate buffered saline
PEPPSI™-IPr [1,3-Bis(2,6-Diisopropylphenyl)imidazol-2-ylidene](3-chloropyridyl)palladium(II) dichloride
PG protecting group
Ph phenyl
PyBOP benzotriazole-1-yl-oxy-tris-pyrrolidino-phosphonium hexafluorophosphate
PyCloP chlorotripyrrolidinophosphonium hexafluorophosphate
RNA ribonucleic acid
RT room temperature
sat. saturated
TBTU O-(benzotriazol-1-yl)-N,N,N',N'-tetramethyluronium tetrafluoroborate
TFA trifluoroacetic acid
THF tetrahydrofuran
TMS trimethylsilyl
$t_R$ retention time
UV ultra-violet
Vis visible
Z benzyloxycarbonyl I. Synthesis of Examples A. Characterization Methods Used NMR: Brucker Avance 400, 400 MHz; chemical shifts are given in ppm relative to the solvent used; multiplicities: s=singlet, d=doublet, t=triplet, q=quadruplet, m=multiplet, br=broad, coupling constants are given in Hz.

LC-MS (I): Thermo Finnigan MSQ Surveyor MS with Agilent 1100 Binary Pump and DAD. Eluents (acidic conditions): A: $H_2O$+0.04% TFA; B: $CH_3CN$; gradient: 5% B→95% B; runtime: 1.5 min; flow: 4.5 mL/min; detection: UV/Vis+MS, $t_R$ is given in min.

LC-MS (A): column Zorbax SB-AQ, 3.5 µm, 4.6×50 mm
LC-MS (B): column Waters XBridge C18, 2.5 µm, 4.6×30 mm
LC-MS (C): column Waters Atlantis T3, 5 µm, 4.6×30 mm;
Eluents (basic conditions): A: $H_2O$+13 mmol/L $NH_4OH$; B: $CH_3CN$; gradient: 5% B→95% B; runtime: 1.5 min; flow: 4.5 mL/min:
LC-MS (D): column Waters XBridge C18, 5 µm, 4.6×50 mm.
LC-MS (D*): column Zorbax Extend C18, 5 µm, 4.6×50 mm.
LC-MS (II): Dionex Ultimate 3000 with Thermo MSQ MS, HPG-3000 pump and photodiode array detector
Eluents (acidic conditions): A: $H_2O$+0.05% HCOOH; B: $CH_3CN$+0.05% HCOOH; gradient: 5% B→95% B; runtime: 2.0 min; flow: 1.8 mL/min; detection: UV/Vis+MS, $t_R$ is given in min.
LC-MS (E): column Ascentis Express C18, 2.7 µm, 2.1×50 mm B. Purification Methods Used Preparative LC-MS (A): flow: 75 mL/min. Detection: UV/Vis and/or MS.
Additional informations for the purification are summarized in the tables below using following explanations:
XBridge: column Waters XBridge C18, 10 µm, 30×75 mm
Atlantis: column Waters Atlantis T3, 10 µm, 30×75 mm
Acidic: eluant: A=$H_2O$ with 0.5% HCOOH, B=$CH_3CN$
Basic: eluant: A=$H_2O$ with 0.125% $NH_4OH$, B=$CH_3CN$
Lipophilic gradient: 30% B→95% B over 4 min then 95% B over 2 min
Normal gradient: 20% B→95% B over 4 min then 95% B over 2 min
Polar gradient: 10% B→95% B over 4 min then 95% B over 2 min
Very polar gradient: 5% B→50% B over 3 min then 50% B→95% B over 1 min and finally 95% B over 2 min

|  | XBridge | | Atlantis |
| --- | --- | --- | --- |
|  | acidic | basic | acidic |
| Lipophilic gradient | Method III | | |
| Normal gradient | Method II | Method IV | Method VII |
| Polar gradient | Method VI | Method V | Method VIII |
| Very polar gradient | Method I | | |

Preparative LC-MS (B): flow: 40 mL/min. Detection: UV/Vis and MS.
XBridge: column Waters XBridge C18 OBD™, 5 µm, 19×50 mm
Acidic: eluant: A=$H_2O$ with 0.1% HCOOH, B=$CH_3CN$ with 0.1% HCOOH
Method 1 (lipophilic gradient): 40% B over 0.1 min, 40%→50% B over 0.1 min, 50% 80% B over 2.9 min, 80%→95% B over 0.1 min and finally 95% B over 1 min
Method 2 (long normal gradient): 25% B over 0.1 min, 25%→35% B over 0.1 min, 35% 65% B over 4.1 min, 65%→95% B over 0.1 min and finally 95% B over 1.1 min
Method 3 (normal gradient): 25% B over 0.2 min, 25%→35% B over 0.1 min, 35% 65% B over 2.9 min, 65%→95% B over 0.1 min and finally 95% B over 1 min Method 4 (long polar gradient): 10% B over 0.2 min, 10%→20% B over 0.1 min, 20% 50% B over 4.1 min, 50%→95% B over 0.1 min and finally 95% B over 1.1 min Method 5 (polar gradient): 10% B over 0.2 min, 10%→20% B over 0.1 min, 20%→50% B over 2.9 min, 50%→95% B over 0.1 min and finally 95% B over 1 min Column chromatography (CC) was performed using silica gel 60 Merck (0.063-0.200 mm) or using prepacked cartridges (SNAP KP-SIL™, SNAP KP-NH™, Isolute™ Silica II, Isolute™ NH$_2$ or Isolute™ C$^{18}$) from Biotage. Additional information for the purification are summarized in the table below:

|  | SNAP KP-SIL ™ | Isolute ™ Silica II | SNAP KP-NH ™ |
|---|---|---|---|
| Hept/EtOAc | Method b | Method c |  |
| EtOAc/MeOH | Method e |  | Method f |
| DCM/MeOH | Method g | Method d | Method a |

The following examples illustrate the invention but do not at all limit the scope thereof.

Preparation of Precursors and Intermediates

A. Synthesis of carboxylic acids

A.1. Synthesis of 4-chloro-1H-indole-5-carboxylic acid

A.1.a. Methyl 4-amino-2-chlorobenzoate

To a solution of 4-amino-2-chlorobenzoic acid (54.2 mmol) in MeOH (325 mL) was added dropwise acetylchloride (163 mmol) and the mixture was refluxed for 5 h. It was concentrated in vacuo and partitioned between EtOAc and a sat. solution of NaHCO$_3$. The organic phase was washed with a sat. solution of NaHCO$_3$, dried over MgSO$_4$ and concentrated in vacuo to give the title compound as beige solid.

LC-MS (B): $t_R$=0.57 min; [M+CH$_3$CN+H]+: 227.29

A.1.b. Mixture of methyl 4-amino-2-chloro-3-iodobenzoate and methyl 4-amino-2-chloro-5-iodobenzoate To a suspension of methyl 4-amino-2-chlorobenzoate (55.8 mmol) in EtOH (558 mL) was added silver sulfate (55.8 mmol) and iodine (58.6 mmol) under argon. The mixture was stirred for 15 min, filtered and the filtrate was concentrated in vacuo. The residue was partitioned between DCM and a 1M aq. solution of NaOH. The organic phase was washed with a 1M aq. solution of NaOH, dried over MgSO$_4$ and concentrated in vacuo. The crude was purified by CC (SNAP KP-SIL™ from Biotage) using Hept/EtOAc/MeOH from 89/11/1 to 81/19/1 to give the mixture of regioisomers as salmon solid. The mixture was enriched from 59 to 66% in methyl 4-amino-2-chloro-3-iodobenzoate by recrystallisation in Hept/EtOAc 75/25, separation of the solid methyl 4-amino-2-chloro-5-iodobenzoate by filtration and evaporation of the mother liquid.

LC-MS (B): $t_R$=0.72 min; [M+CH$_3$CN+H]+: 352.79

In addition, pure methyl 4-amino-2-chloro-5-iodobenzoate regioisomer was isolated as pink to orange solid.

LC-MS (B): $t_R$=0.75 min; [M+CH$_3$CN+H]+: 352.80

A.1.c. Methyl 4-amino-2-chloro-3-((trimethylsilyl)ethynyl)benzoate

A solution of mixture of methyl 4-amino-2-chloro-3-iodobenzoate and methyl 4-amino-2-chloro-5-iodobenzoate from previous step (13.3 mmol) in Et$_3$N (110 mL) and toluene (110 mL) was heated to 60° C. under argon and treated with PPh$_3$ (1.33 mmol), CuI (1.33 mmol), Pd(PPh$_3$)$_2$Cl$_2$ (0.66 mmol) and trimethylsilylacetylene (19.9 mmol). The mixture was stirred for 30 min at 60° C. and 1 h at 70° C., quenched with a 10% aq. solution of NH$_4$Cl and extracted with EtOAc. The organic phase was washed with brine, dried over MgSO4 and concentrated in vacuo. The crude was purified by CC (SNAP KP-SIL™ from Biotage) using Hept/EtOAc from 1/0 to 8/2 to give the title compound (second eluting product) as light yellow solid.

LC-MS (B): $t_R$=0.93 min; [M+CH$_3$CN+H]+: 322.70

In addition, methyl 4-amino-2-chloro-5-((tri methylsilyl)ethynyl)benzoate was isolated as orange solid (first eluting product).

LC-MS (B): $t_R$=0.97 min; [M+CH$_3$CN+H]+: 323.22

A.1.d. Methyl 4-amino-2-chloro-3-ethynylbenzoate

To a solution of methyl 4-amino-2-chloro-3-((trimethylsilyl)ethynyl)benzoate (8.81 mmol) in MeOH (8.81 mL) was added K$_2$CO$_3$ (9.69 mmol). The mixture was stirred for 15 min and the solvent was evaporated off. The residue was partitioned between DCM and water. The organic phase was dried over MgSO$_4$ and concentrated in vacuo. The crude was purified by CC (Isolute™ Silica II from Biotage) using DCM to give the title compound as yellowish solid.

LC-MS (B): $t_R$=0.66 min; [M+H]+: 210.04

A.1.e. Methyl 4-chloro-1H-indole-5-carboxylate

To a mixture of methyl 4-amino-2-chloro-3-ethynylbenzoate (5.57 mmol), chloro(1,5-cyclooctadiene)rhodium(1) dimer (0.28 mmol) and tris(4-fluorophenyl)phosphine (3.34 mmol) was added under argon degassed DMF (28 mL). The mixture was heated to 85° C. for 50 min, cooled to RT and partitioned between Et$_2$O and water. The organic phase was washed with brine, dried over MgSO$_4$ and concentrated in vacuo. The crude was purified by CC (SNAP KP-SIL™ from Biotage) using Hept/DCM 1/0 to 0/1 to give the title compound as brownish solid.

LC-MS (B): $t_R$=0.69 min; [M+H]+: 210.14

A.1.f. 4-Chloro-1H-indole-5-carboxylic acid (Saponification: general procedure I)

To a suspension of methyl 4-chloro-1H-indole-5-carboxylate (4 mmol) in MeOH (24 mL) was added a 2M aq. solution of LiOH (4 mL). The mixture was stirred for 5 h at 65° C. then ON at 45° C. It was evaporated off and partitioned between EtOAc and H$_2$O. The aq. phase was acidified with a 25% solution of HCl and extracted 3 times with DCM. The combined organic phases were dried over MgSO$_4$ and concentrated in vacuo to give the title compound as off-white solid.

LC-MS (A): $t_R$=0.65 min; [M+H]+: 196.06

A.2. Synthesis of 4-chloro-1-methyl-1H-indole-5-carboxylic acid

To a solution of methyl 4-chloro-1H-indole-5-carboxylate (0.48 mmol) in anh. DMF (1.2 mL) was added at 0° C. NaH as a 60% suspension in mineral oil (1.2 mmol). The mixture was stirred for 5 min and MeI (0.72 mmol) was added dropwise at 0° C. The mixture was stirred for 1 h at RT, quenched with water and partitioned between Et$_2$O and water. The aq. phase was acidified with a 1M aq. solution of HCl and extracted 3 times with DCM. The combined organic phases were dried over MgSO$_4$ and concentrated in vacuo to give the title compound as brown solid.

LC-MS (B): $t_R$=0.61 min; [M+H]+: 210.05

A.3. Synthesis of
4-chloro-3-formyl-1H-indole-5-carboxylic acid

A.3.a. Methyl
4-chloro-3-formyl-1H-indole-5-carboxylate

Phosphoryl chloride (1.43 mmol) was added at 0° C. to anh. DMF (4 mL). To this mixture was added dropwise at 0° C. a solution of methyl 4-chloro-1H-indole-5-carboxylate (0.95 mmol) in anh. DMF (2 mL). The mixture was stirred for 5 min at 0° C., heated to 40° C. and stirred for 4 h 30. It was poured onto ice, treated with a 1M aq. solution of NaOH to adjust pH to 10-11 and heated to 100° C. for 5 min. The mixture was acidified with a 1M solution of HCl and extracted 3 times with DCM. The combined organic phases were dried and concentrated in vacuo. The crude was purified by CC (SNAP KP-SIL™ from Biotage) using Hept/EtOAc from 1/0 to 35/65 to give the title compound as orange solid.

LC-MS (A): $t_R$=0.71 min; [M+H]+: 238.05

A.3.b. 4-Chloro-3-formyl-1H-indole-5-carboxylic acid

This compound was prepared using a method analogous to that of 4-chloro-1H-indole-5-carboxylic acid, methyl 4-chloro-3-formyl-1H-indole-5-carboxylate replacing methyl 4-chloro-1H-indole-5-carboxylate.

LC-MS (B): $t_R$=0.41 min; [M+H]+: 224.07

A.4. Synthesis of
4-chloro-7-methyl-M-indole-5-carboxylic acid

A.4.a. Methyl 4-chloro-7-iodo-3-(methylthio)-1H-indole-5-carboxylate (Gassman indole)

To a suspension of methyl 4-amino-2-chloro-5-iodobenzoate (6.21 mmol) in anh. DCM (29 mL) was added at −60° C. NCS (7.45 mmol) and the mixture was stirred for 10 min. A solution of (methylthio)acetaldehyde dimethyl acetal (7.45 mmol) in anh. DCM (5.8 mL) was added at −60° C. and the mixture was stirred allowing temperature to reach −30° C. A solution of Et$_3$N (7.45 mmol) in anh. DCM (5 mL) was added at −30° C. and the mixture was stirred allowing temperature to reach RT. It was concentrated in vacuo, PhCl (17.4 mL) and Et$_3$N (20.5 mmol) were added and the mixture was heated to 125° C. and stirred for 2 h. The volatiles were evaporated off and the residue was taken up in Et$_2$O (28.7 mL) and treated with a 4M solution of HCl in dioxane (11 mL) for 30 min. It was partitioned between EtOAc and a sat. solution of NaHCO$_3$, the organic phase was dried over MgSO$_4$ and concentrated in vacuo. The crude was purified by CC (SNAP KP-SIL™ from Biotage) using Hept/EtOAc from 9/1 to 65/35 to give the title compound as yellow solid.

LC-MS (A): $t_R$=0.93 min; [M+H]+: 381.71

A.4.b. Methyl 4-chloro-7-methyl-3-(methylthio)-1H-indole-5-carboxylate

To a solution of methyl 4-chloro-7-iodo-3-(methylthio)-1H-indole-5-carboxylate (0.42 mmol) in dioxane (1 mL) was added under argon a 2M solution of methylzinc chloride in THF (1.04 mmol) and a solution of Pd(dppf)Cl$_2$.DCM (0.03 mmol) in dioxane (0.5 mL). The mixture was stirred ON at 65° C. in a sealed vial, diluted with EtOAc and washed with a sat. solution of Rochelle salt and brine. The organic phase was dried over MgSO$_4$ and concentrated in vacuo. The crude was purified by CC (SNAP KP-SIL™ from Biotage) using DCM to give the title compound as yellow solid.

LC-MS (A): $t_R$=0.86 min; [M+H]+: 270.11

A.4.c. Methyl
4-chloro-7-methyl-1H-indole-5-carboxylate

To a solution of methyl 4-chloro-7-methyl-3-(methylthio)-1H-indole-5-carboxylate (0.24 mmol) in EtOH (4.11 mL) was added Actimet M Raney Nickel (14 mg). The mixture was stirred for 2 h at RT and filtered over a pad of celite. The filtrate was concentrated in vacuo to give the title compound as white solid.

LC-MS (A): $t_R$=0.82 min; [M+H]+: 224.16

A.4.d. 4-Chloro-7-methyl-1H-indole-5-carboxylic acid (Saponification II)

To a solution of methyl 4-chloro-7-methyl-1H-indole-5-carboxylate (0.11 mmol) in MeOH (0.4 mL), THF (0.4 mL) and H$_2$O (0.4 mL) was added LiOH.H$_2$O (0.44 mmol). The mixture was stirred for 2 h at 60° C. It was evaporated off and partitioned between EtOAc and H$_2$O. The aq. phase was acidified with a 25% solution of HCl and extracted 3 times with EtOAc. The combined organic phases were dried over MgSO$_4$ and concentrated in vacuo to give the title compound as pink solid.

LC-MS (A): $t_R$=0.69 min; [M+H]+: 209.98

A.5. Synthesis of
4-chloro-2-methyl-M-indole-5-carboxylic acid

A.5.a. Methyl 2-chloro-4-hydrazinyl-5-iodobenzoate

To a solution of methyl 4-amino-2-chloro-5-iodobenzoate (6.42 mmol) in 37% HCl (4.40 mL) was added dropwise at 0° C. a solution of sodium nitrite (7.49 mmol) in water (2.15 mL). The mixture was stirred for 15 min at 0° C. and a solution of tin(II) chloride dihydrate (16 mmol) in water (1 mL) and 37% HCl (4.28 mL) was added dropwise at 0° C. The mixture was stirred for 15 min and quenched with consecutive addition of water, a 10% solution of Na$_2$CO$_3$ and a 20% solution of NaOH. It was extracted 3 times with DCM, the combined organic phases were dried over MgSO$_4$ and concentrated in vacuo. The crude was purified by CC (SNAP KP-SIL™ from Biotage) using Hept/EtOAc from 95/5 to 62/38 to give the title compound as beige solid.

LC-MS (A): $t_R$=0.73 min; [M+CH$_3$CN+H]+: 367.75

A.5.b. Methyl 4-chloro-7-iodo-2-methyl-3-(methylthio)-1H-indole-5-carboxylate

To a solution of methyl 2-chloro-4-hydrazinyl-5-iodobenzoate (0.76 mmol) in a 1.25 M solution of HCl in EtOH (1.8 mL) was added 1-methylthio-2-propanone (1.38 mmol). The mixture was stirred for 2 h at 65° C. and filtered. The filtrate was concentrated in vacuo and the crude was purified by preparative LC-MS using method I.

LC-MS (A): $t_R$=0.96 min; [M+H]+: 395.73

A.5.c. Methyl 4-chloro-2-methyl-1H-indole-5-carboxylate

This compound was prepared using a method analogous to that of methyl 4-chloro-7-methyl-1H-indole-5-carboxylate, methyl 4-chloro-7-iodo-2-methyl-3-(methylthio)-1H-indole-5-carboxylate replacing 4-chloro-7-methyl-3-(methylthio)-1H-indole-5-carboxylate except that the reaction mixture was stirred for 48 h at RT and further additions of Actimet M Raney Nickel was required until completion of the reaction.

LC-MS (A): $t_R$=0.83 min; [M+H]+: 224.10

A.5.d. 4-Chloro-2-methyl-1H-indole-5-carboxylic acid

This compound was prepared using a method analogous to that of 4-chloro-1H-indole-5-carboxylic acid, methyl 4-chloro-2-methyl-1H-indole-5-carboxylate replacing methyl 4-chloro-1H-indole-5-carboxylate.

LC-MS (A): $t_R$=0.69 min; [M+H]+: 210.04

A.6. Synthesis of 4-chloro-7-iodo-3-(methylthio)-1H-indole-5-carboxylic acid To a solution of methyl 4-chloro-7-iodo-3-(methylthio)-1H-indole-5-carboxylate (0.52 mmol) in MeOH (0.45 mL) and H$_2$O (0.45 mL) was added KOH (1.57 mmol). The mixture was stirred ON at 70° C. It was evaporated off and partitioned between Et$_2$O and water. The aq. phase was acidified with a 1M solution of HCl and extracted 3 times with EtOAc. The combined organic phases were dried over MgSO$_4$ and concentrated in vacuo to give the title compound as brownish solid.

LC-MS (A): $t_R$=0.78 min; [M+H]+: 368.91

A.7. Synthesis of 4-chloro-3-fluoro-1H-indole-5-carboxylic acid

A.7.a. Methyl 4-chloro-3-fluoro-1H-indole-5-carboxylate

To a solution of methyl 4-chloro-1H-indole-5-carboxylate (0.24 mmol) in MeOH (2.09 mL) was added 1-fluoro-2,4,6-trimethylpyridinium triflate (0.31 mmol). The mixture was heated to 65° C. and stirred for 24 h. It was concentrated in vacuo and the residue was purified by CC (SNAP KP-SIL™ from Biotage) using Hept/EtOAc from 1/0 to 1/1 to give the title compound as beige solid.

LC-MS (A): $t_R$=0.80 min
$^1$H NMR ((CD$_3$)$_2$SO) δ: 11.54 (s, 1 H), 7.60 (d, J=8.6 Hz, 1 H), 7.57 (t, J=2.5 Hz, 1 H), 7.41 (dd, J$_1$=8.6 Hz, J$_2$=2.4 Hz, 1 H), 3.86 (s, 3 H)

A.7.b. 4-Chloro-3-fluoro-1H-indole-5-carboxylic acid

This compound was prepared using a method analogous to that of 4-chloro-7-methyl-1H-indole-5-carboxylic acid, methyl 4-chloro-3-fluoro-1H-indole-5-carboxylate replacing methyl 4-chloro-7-methyl-1H-indole-5-carboxylate.

LC-MS (A): $t_R$=0.67 min; [M+CH$_3$CN+H]+: 255.04

A.8. Synthesis of 4-methoxy-1H-indole-5-carboxylic acid

A.8.a. Methyl 7-iodo-4-methoxy-3-(methylthio)-1H-indole-5-carboxylate

This compound was prepared using a method analogous to that of methyl 4-chloro-7-iodo-3-(methylthio)-1H-indole-5-carboxylate, commercially available methyl 4-amino-5-iodo-2-methoxybenzoate replacing methyl 4-amino-2-chloro-5-iodobenzoate.

LC-MS (A): $t_R$=0.90 min; [M+H]+: 377.76

A.8.b. Methyl 4-methoxy-1H-indole-5-carboxylate

This compound was prepared using a method analogous to that of methyl 4-chloro-7-methyl-1H-indole-5-carboxylate, methyl 7-iodo-4-methoxy-3-(methylthio)-1H-indole-5-carboxylate replacing 4-chloro-7-methyl-3-(methylthio)-1H-indole-5-carboxylate except that the reaction mixture was stirred for 2 h at RT and one further addition of Actimet M Raney Nickel was required until completion of the reaction.

LC-MS (A): $t_R$=0.69 min; [M+H]+: 206.28

A.8.c. 4-Methoxy-1H-indole-5-carboxylic acid

This compound was prepared using a method analogous to that of 4-chloro-7-methyl-1H-indole-5-carboxylic acid, methyl 4-methoxy-1H-indole-5-carboxylate replacing methyl 4-chloro-7-methyl-1H-indole-5-carboxylate.

LC-MS (A): $t_R$=0.60 min; [M+H]+: 192.28

A.9. Synthesis of 3,4-dichloro-1H-indole-5-carboxylic acid

A.9.a. Methyl 3,4-dichloro-1H-indole-5-carboxylate

To a solution of methyl 4-chloro-1H-indole-5-carboxylate (0.72 mmol) in DMF (1 mL) was added portionwise at 0° C. NCS (0.79 mmol). The mixture was stirred ON at RT, quenched with a 10% solution of Na$_2$S$_2$O$_3$ and extracted with EtOAc. The organic phase was washed with a 10% solution of Na$_2$S$_2$O$_3$ and brine, dried over MgSO$_4$ and concentrated in vacuo to give the title compound as light orange solid.

LC-MS (A): $t_R$=0.83 min
$^1$H NMR ((CD$_3$)$_2$SO) δ: 12.02 (s, 1 H), 7.74 (d, J=2.7 Hz, 1 H), 7.57 (d, J=8.53 Hz, 1 H), 7.47 (d, J=8.53 Hz, 1 H), 3.86 (s, 3 H)

A.9.b. 3,4-Dichloro-1H-indole-5-carboxylic acid

This compound was prepared using a method analogous to that of 4-chloro-7-methyl-1H-indole-5-carboxylic acid, Methyl 3,4-dichloro-1H-indole-5-carboxylate replacing methyl 4-chloro-7-methyl-1H-indole-5-carboxylate except that the reaction mixture was stirred ON at 60° C.
LC-MS (D*): $t_R$=0.18 min; [M–H]–: 228.04

A.10. Synthesis of 4-chloro-7-nitro-1H-indole-5-carboxylic acid

A.10.a. 4-Amino-2-chloro-5-nitrobenzoic acid

This compound was synthesized according to *Helv. Chim. Acta*, 1937, 20, 1407-1412.

A.10.b. Methyl 4-amino-2-chloro-5-nitrobenzoate

This compound was prepared using a method analogous to that of methyl 4-amino-2-chlorobenzoate, 4-amino-2-chloro-5-nitrobenzoic acid replacing 4-amino-2-chlorobenzoic acid except that the crude was additionally purified by CC (SNAP KP-SIL™ from Biotage) using Hept/EtOAc from 3/1 to 0/1.
LC-MS (A): $t_R$=0.79 min
$^1$H NMR ((CD$_3$)$_2$SO) δ: 8.57 (s, 1 H), 7.96 (s, 2 H), 7.14 (s, 1 H), 3.79 (s, 3 H)

A.10.c. Methyl 4-amino-2-chloro-3-iodo-5-nitrobenzoate

To a solution of methyl 4-amino-2-chloro-5-nitrobenzoate (13.5 mmol) in DCM (33.7 mL) was added bis(pyridine)iodinium tetrafluoroborate (27 mmol) and trifluoromethanesulfonic acid (53.9 mmol). The mixture was stirred for 1 h at RT and partitioned between water and DCM. The organic phase was washed with a 10% solution of Na$_2$S$_2$O$_3$, dried over MgSO$_4$ and concentrated in vacuo. The crude was purified by CC (SNAP KP-SIL™ from Biotage) using DCM/MeOH from 1/0 to 95/5 to give the title compound as brown solid.
LC-MS (A): $t_R$=0.88 min
$^1$H NMR ((CD$_3$)$_2$SO) δ: 8.62 (s, 1 H), 7.77 (s broad, 2 H), 3.84 (s, 3 H)

A.10.d. Methyl 4-amino-2-chloro-5-nitro-3-(trimethylsilyl)ethynyl)benzoate

This compound was prepared using a method analogous to that of methyl 4-amino-2-chloro-3-((trimethylsilyl)ethynyl)benzoate, methyl 4-amino-2-chloro-3-iodo-5-nitrobenzoate replacing the mixture of methyl 4-amino-2-chloro-3-iodobenzoate and methyl 4-amino-2-chloro-5-iodobenzoate.
LC-MS (A): $t_R$=1.03 min
$^1$H NMR ((CD$_3$)$_2$SO) δ: 8.59 (s, 1 H), 7.55 (s very broad, 2 H), 3.84 (s, 3 H), 0.31 (s, 9 H)

A.10.e. Methyl 4-amino-2-chloro-3-ethynyl-5-nitrobenzoate

This compound was prepared using a method analogous to that of methyl 4-amino-2-chloro-3-ethynylbenzoate, methyl 4-amino-2-chloro-5-nitro-3-((trimethylsilyl)ethynyl)benzoate replacing methyl 4-amino-2-chloro-3-((trimethylsilyl)ethynyl)benzoate.
LC-MS (A): $t_R$=0.85 min
$^1$H NMR ((CD$_3$)$_2$SO) δ: 8.57 (s, 1 H), 7.73 (s very broad, 2 H), 5.17 (s, 1 H), 3.81 (s, 3 H)

A.10.f. Methyl 4-chloro-7-nitro-1H-indole-5-carboxylate

This compound was prepared using a method analogous to that of methyl 4-chloro-1H-indole-5-carboxylate, methyl 4-amino-2-chloro-3-ethynyl-5-nitrobenzoate replacing methyl 4-amino-2-chloro-3-ethynylbenzoate except that the reaction was additionally stirred ON at 45° C. until completion.
LC-MS (A): $t_R$=0.86 min
$^1$H NMR ((CD$_3$)$_2$SO) δ: 12.52 (s, 1 H), 8.56 (s, 1 H), 7.74 (m, 1 H), 6.91 (dd, J$_1$=3.2 Hz, J$_2$=1.9 Hz, 1 H), 3.93 (s, 3 H)

A.10.g. 4-Chloro-7-nitro-1H-indole-5-carboxylic acid

This compound was prepared using a method analogous to that of 4-chloro-7-methyl-1H-indole-5-carboxylic acid, methyl 4-chloro-7-nitro-1H-indole-5-carboxylate replacing methyl 4-chloro-7-methyl-1H-indole-5-carboxylate except that the reaction was stirred for 2 h at RT.
LC-MS (A): $t_R$=0.71 min
$^1$H NMR ((CD$_3$)$_2$SO) δ: 13.56 (s br, 1 H), 12.47 (s, 1 H), 8.58 (s, 1 H), 7.72 (dd, J$_1$=J$_2$=2.6 Hz, 1 H), 6.91 (m, 1 H)

A.11. Synthesis of 4-chloro-3-methyl-1H-indole-5-carboxylic acid

A.11.a. Methyl 4-chloro-3-methyl-1H-indole-5-carboxylate

To a solution of methyl 4-chloro-3-formyl-1H-indole-5-carboxylate (0.21 mmol) in DMF (0.5 mL) was added p-toluenesulfonic acid monohydrate (0.03 mmol), p-toluenesulfonyl hydrazide (0.27 mmol) and sulfolane (0.25 mmol). The mixture was heated for 1 h at 100° C. It was cooled to RT, sodium cyanoborohydride (0.84 mmol) was added and it was heated for 1 h at 100° C. The mixture was quenched with water and extracted 3 times with EtOAc. The combined organic phases were dried over MgSO$_4$ and concentrated in vacuo. The crude was purified by CC (SNAP KP-SIL™ from Biotage) using Hept/EtOAc from 1/0 to 6/4 to give the title compound as white solid.
LC-MS (A): $t_R$=0.83 min; [M+H]+: 224.03

A.11.b. 4-Chloro-3-methyl-1H-indole-5-carboxylic acid

This compound was prepared using a method analogous to that of 4-chloro-7-methyl-1H-indole-5-carboxylic acid, methyl 4-chloro-3-methyl-1H-indole-5-carboxylate replacing methyl 4-chloro-7-methyl-1H-indole-5-carboxylate.
LC-MS (A): $t_R$=0.69 min; [M+H]+: 210.18

A.12. Synthesis of 4,6-dichloro-1H-indole-5-carboxylic acid

A.12.a. 2,6-Dichloro-4-nitrobenzoic acid

A solution of 1,3-dichloro-2-methyl-5-nitrobenzene (4.85 mmol) in pyridine (5 mL) and water (10 mL) was heated to 90° C. and KMnO$_4$ (29.1 mmol) was added portionwise. The mixture was refluxed for 2 h and stirred ON at RT. It was heated to 90° C., additional amount of KMnO$_4$ (12.7 mmol) was added and it was refluxed for 7 h. The mixture was filtered, the filtrate was basified with a 1M solution of NaOH until pH 12-13 and washed with EtOAc. The aq. phase was acidified with a 1M solution of HCl until pH 1-2 and extracted 3 times with EtOAc. The combined organic phases were dried over MgSO$_4$ and concentrated in vacuo to give the crude acid as orange solid.
LC-MS (A): $t_R$=0.45 min
LC-MS (D*): $t_R$=0.17 min; [M–H]–: 234.01

A.12.b. Methyl 2,6-dichloro-4-nitrobenzoate

To a solution of 2,6-dichloro-4-nitrobenzoic acid (1.63 mmol) in DMF (5 mL) was added cesium carbonate (2.44 mmol). The suspension was stirred for 30 min at RT and MeI (1.63 mmol) was added. The mixture was stirred for 2 h, quenched with water and extracted 3 times with EtOAc. The combined organic phases were dried and concentrated in vacuo to give the title compound as yellow solid.

LC-MS (A): $t_R$=0.88 min
$^1$H NMR ((CD$_3$)$_2$SO) δ: 8.48 (s, 2 H), 3.99 (s, 3 H)

A.12.c. Methyl 4-amino-2,6-dichlorobenzoate

To a solution of methyl 2,6-dichloro-4-nitrobenzoate (1.44 mmol) in DMF (2 mL) was added tin(II) chloride dihydrate (5.04 mmol). The mixture was stirred at 100° C. for 40 min under microwave condition and quenched with water. It was basified with a 1M solution of NaOH until pH 11-12 and extracted 3 times with EtOAc. The combined organic phases were washed with brine, dried over MgSO$_4$ and concentrated in vacuo. The crude was purified by CC (SNAP KP-NH™ from Biotage) using Hept/EtOAc from 1/0 to 1/1 to give the title compound as yellow solid.

LC-MS (A): $t_R$=0.78 min; [M+H]+: 220.07

A.12.d. Methyl 4-amino-2,6-dichloro-3-iodobenzoate

This compound was prepared using a method analogous to that of the mixture of methyl 4-amino-2-chloro-3-iodobenzoate and methyl 4-amino-2-chloro-5-iodobenzoate, methyl 4-amino-2,6-dichlorobenzoate replacing methyl 4-amino-2-chlorobenzoate except that no purification was done.

LC-MS (A): $t_R$=0.86 min; [M+CH$_3$CN+H]+: 386.57

A.12.e. Methyl 4-amino-2,6-dichloro-3-(trimethylsilyl)ethynyl)benzoate

This compound was prepared using a method analogous to that of methyl 4-amino-2-chloro-3-((trimethylsilyl)ethynyl)benzoate, methyl 4-amino-2,6-dichloro-3-iodobenzoate replacing the mixture of methyl 4-amino-2-chloro-3-iodobenzoate and methyl 4-amino-2-chloro-5-iodobenzoate.

LC-MS (A): $t_R$=1.00 min; [M+H]+: 316.07

A.12.f. Methyl 4-amino-2,6-dichloro-3-ethynylbenzoate

This compound was prepared using a method analogous to that of methyl 4-amino-2-chloro-3-ethynylbenzoate, methyl 4-amino-2,6-dichloro-3-((trimethylsilyl)ethynyl)benzoate replacing methyl 4-amino-2-chloro-3-((trimethylsilyl)ethynyl)benzoate.

LC-MS (A): $t_R$=0.83 min; [M+H]+: 243.91

A.12.g. Methyl 4,6-dichloro-1H-indole-5-carboxylate

This compound was prepared using a method analogous to that of methyl 4-chloro-1H-indole-5-carboxylate, methyl 4-amino-2,6-dichloro-3-ethynylbenzoate replacing methyl 4-amino-2-chloro-3-ethynylbenzoate.

LC-MS (A): $t_R$=0.84 min
$^1$H NMR ((CD$_3$)$_2$SO) δ: 11.79 (s, 1 H), 7.62 (dd, J$_1$=2.9 Hz, J$_2$=2.5 Hz, 1 H), 7.59 (d, J=0.9 Hz, 1 H), 6.58 (m, 1 H), 3.91 (s, 3 H)

A.12.h. 4,6-Dichloro-1H-indole-5-carboxylic acid

This compound was prepared using a method analogous to that of 4-chloro-7-methyl-1H-indole-5-carboxylic acid, methyl 4,6-dichloro-1H-indole-5-carboxylate replacing methyl 4-chloro-7-methyl-1H-indole-5-carboxylate.

LC-MS (A): $t_R$=0.68 min
LC-MS (D*): $t_R$=0.15 min; [M−H]−: 228.06

A.13. Synthesis of 4-chloro-6-methyl-1H-indole-5-carboxylic acid

A.13.a. 2-Chloro-6-methyl-4-nitrobenzonitrile

To a solution of copper(I) cyanide (46.4 mmol) in CH$_3$CN (60 mL) was added tert-butylnitrite (36.3 mmol). The mixture was cooled to 0° C. and a solution of 2-chloro-6-methyl-4-nitroaniline (20.2 mmol) was added dropwise for 10 min. The mixture was heated for 2 h at 70° C., quenched with a 10% solution of Na$_2$CO$_3$ and the pH was adjusted to 11 with a 1M solution of NaOH. It was extracted 3 times with EtOAc and the combined organic phases were washed with brine, dried over MgSO$_4$ and concentrated in vacuo. The crude was purified by CC (SNAP KP-Sil™ from Biotage) using Hept/EtOAc from 1/0 to 94/6 to give the title compound as yellow solid.

LC-MS (A): $t_R$=0.85 min
$^1$H NMR ((CD$_3$)$_2$SO) δ: 8.41 (s, 1 H), 8.36 (s, 1 H), 2.66 (s, 3 H)

A.13.b. 2-Chloro-6-methyl-4-nitrobenzoic acid

To a suspension of 2-chloro-6-methyl-4-nitrobenzonitrile (5.09 mmol) in 2-propanol (11 mL) and water (11 mL) was added KOH (25.4 mmol). The mixture was heated for 1 h at 60° C., diluted with water and extracted 3 times with EtOAc. The combined organic phases were washed with brine, dried over MgSO$_4$ and concentrated in vacuo to give the primary amide intermediate as brown oil (LC-MS (A): $t_R$=0.58 min).

The crude primary amide was suspended in water (2.54 mL) and H$_2$SO$_4$ (7.63 mL) and heated to 80° C. Sodium nitrite (9.16 mmol) was added portionwise and the mixture was stirred for 1 h at 80° C. It was quenched with water, basified with a 32% solution of NaOH until pH 13-14 and washed 3 times with EtOAc. The aqueous phase was acidified with a 24% solution of HCl until pH 1-2 and extracted 3 times with EtOAc. The combined organic phases were dried over MgSO$_4$ and concentrated in vacuo to give the title compound as brown oil.

LC-MS (A): $t_R$=0.62 min
$^1$H NMR ((CD$_3$)$_2$SO) δ: 12.07 (s br, 1 H), 8.22 (dd, J$_1$=2.2 Hz, J$_2$=0.4 Hz, 1 H), 8.20 (dd, j$_1$=2.1 Hz, J$_2$=0.6 Hz, 1 H), 2.43 (s, 3 H)

A.13.c. Methyl 2-chloro-6-methyl-4-nitrobenzoate

This compound was prepared using a method analogous to that of methyl 2,6-dichloro-4-nitrobenzoate, 2-chloro-6-methyl-4-nitrobenzoic acid replacing 2,6-dichloro-4-nitrobenzoic acid.

LC-MS (A): $t_R$=0.87 min
$^1$H NMR ((CD$_3$)$_2$SO) δ: 8.26 (dd, J$_1$=2.0 Hz, J$_2$=0.4 Hz, 1 H), 8.23 (dd, J$_1$=2.0 Hz, J$_2$=0.6 Hz, 1 H), 3.96 (s, 3 H), 2.41 (s, 3 H)

A.13.d. Methyl 4-amino-2-chloro-6-methylbenzoate

This compound was prepared using a method analogous to that of methyl 4-amino-2,6-dichlorobenzoate, methyl 2-chloro-6-methyl-4-nitrobenzoate replacing methyl 2,6-dichloro-4-nitrobenzoate except that the mixture was heated for 15 min at 100° C. under microwave conditions.
LC-MS (A): $t_R$=0.72 min; [M+CH$_3$CN+H]+: 241.05

A.13.e. Methyl 4-amino-2-chloro-3-iodo-6-methylbenzoate

This compound was prepared using a method analogous to that of the mixture of methyl 4-amino-2-chloro-3-iodobenzoate and methyl 4-amino-2-chloro-5-iodobenzoate, methyl 4-amino-2-chloro-6-methylbenzoate replacing methyl 4-amino-2-chlorobenzoate.
LC-MS (A): $t_R$=0.84 min; [M+CH$_3$CN+H]+: 366.86
The other regioisomer, methyl 4-amino-2-chloro-5-iodo-6-methylbenzoate, was additionally isolated.
LC-MS (A): $t_R$=0.85 min; [M+CH$_3$CN+H]+: 366.87

A.13.f. Methyl 4-amino-2-chloro-6-methyl-3-(trimethylsilyl)ethynyl)benzoate

This compound was prepared using a method analogous to that of methyl 4-amino-2-chloro-3-((trimethylsilyl)ethynyl)benzoate, methyl 4-amino-2-chloro-3-iodo-6-methyl benzoate replacing the mixture of methyl 4-amino-2-chloro-3-iodobenzoate and methyl 4-amino-2-chloro-5-iodobenzoate.
LC-MS (A): $t_R$=0.98 min; [M+H]+: 296.12

A.13.g. Methyl 4-amino-2-chloro-3-ethynyl-6-methylbenzoate

This compound was prepared using a method analogous to that of methyl 4-amino-2-chloro-3-ethynylbenzoate, methyl 4-amino-2-chloro-6-methyl-3-((trimethylsilyl)ethynyl) benzoate replacing methyl 4-amino-2-chloro-3-((trimethylsilyl)ethynyl)benzoate.
LC-MS (A): $t_R$=0.80 min; [M+H]+: 224.09

A.13.h. Methyl 4-chloro-6-methyl-1H-indole-5-carboxylate

This compound was prepared using a method analogous to that of methyl 4-chloro-1H-indole-5-carboxylate, methyl 4-amino-2-chloro-3-ethynyl-6-methylbenzoate replacing methyl 4-amino-2-chloro-3-ethynylbenzoate.
LC-MS (A): $t_R$=0.82 min; [M+H]+: 224.09

A.13.i. 4-Chloro-6-methyl-1H-indole-5-carboxylic acid

This compound was prepared using a method analogous to that of 4-chloro-7-methyl-1H-indole-5-carboxylic acid, methyl 4,6-dichloro-1H-indole-5-carboxylate replacing methyl 4-chloro-7-methyl-1H-indole-5-carboxylate.
LC-MS (A): $t_R$=0.66 min
LC-MS (D*): $t_R$=0.16 min; [M−H]−: 208.13

A.14. Synthesis of 3-bromo-4-chloro-7-methyl-1H-indole-5-carboxylic acid

A.14.a. Methyl 3-bromo-4-chloro-7-methyl-1H-indole-5-carboxylate

To a solution of methyl 4-chloro-7-methyl-1H-indole-5-carboxylate (0.47 mmol) in chlorobenzene (0.47 mL) was added at 55° C. NBS (0.52 mmol) and AIBN (0.05 mmol). The mixture was stirred for 30 min at 55° C., diluted with DCM and filtered. The filtrate was washed with a 1M solution of HCl, dried over MgSO$_4$ and concentrated in vacuo. The crude was purified by preparative LC-MS using method II to give the title compound as orange solid.
LC-MS (A): $t_R$=0.90 min
$^1$H NMR ((CD$_3$)$_2$SO) δ: 12.45 (s br, 1 H), 7.44 (s, 1 H), 6.73 (s, 1 H), 3.85 (s, 3 H), 2.47 (s, 3 H)

A.14.b. 3-Bromo-4-chloro-7-methyl-1H-indole-5-carboxylic acid

This compound was prepared using a method analogous to that of 4-chloro-7-methyl-1H-indole-5-carboxylic acid, methyl 3-bromo-4-chloro-7-methyl-1H-indole-5-carboxylate replacing methyl 4-chloro-7-methyl-1H-indole-5-carboxylate.
LC-MS (A): $t_R$=0.77 min
LC-MS (D*): $t_R$=0.43 min; [M−H]−: 287.94

A.15. Synthesis of 4-chloro-7-isobutyl-1H-indole-5-carboxylic acid

A.15.a. Methyl 4-amino-2-chloro-5-isobutylbenzoate

To a solution of methyl 4-amino-2-chloro-5-iodobenzoate (3.36 mmol) in toluene/water 20/1 (40 mL) was added under argon K$_3$PO$_4$ (11.8 mmol), PdCl$_2$(PPh$_3$)$_2$ (0.34 mmol) and (2-methylpropyl)boronic acid (6.72 mmol). The mixture was heated ON at 110° C. in a sealed vial, quenched with water and extracted with EtOAc. The organic phase was washed with brine, dried over MgSO$_4$ and concentrated in vacuo. The crude was purified by CC (SNAP KP-Sil™ from Biotage) using Hept/EtOAc from 1/0 to 0/1 to give the title compound as yellow oil.
LC-MS (A): $t_R$=0.90 min; [M+CH$_3$CN+H]+: 283.06

A.15.b. Methyl 4-amino-2-chloro-3-iodo-5-isobutylbenzoate

This compound was prepared using a method analogous to that of the mixture of methyl 4-amino-2-chloro-3-iodobenzoate and methyl 4-amino-2-chloro-5-iodobenzoate, methyl 4-amino-2-chloro-5-isobutylbenzoate replacing methyl 4-amino-2-chlorobenzoate.
LC-MS (A): $t_R$=0.97 min; [M+CH$_3$CN+H]+: 408.77

A.15.c. Methyl 4-amino-2-chloro-5-isobutyl-3-((trimethylsilyl)ethynyl)benzoate

This compound was prepared using a method analogous to that of methyl 4-amino-2-chloro-3-((trimethylsilyl)ethynyl)benzoate, methyl 4-amino-2-chloro-3-iodo-5-isobutylbenzoate replacing the mixture of methyl 4-amino-2-chloro-3-iodobenzoate and methyl 4-amino-2-chloro-5-iodobenzoate.
LC-MS (A): $t_R$=1.07 min; [M+H]+: 337.90

A.15.d. Methyl 4-amino-2-chloro-3-ethynyl-5-isobutylbenzoate

This compound was prepared using a method analogous to that of methyl 4-amino-2-chloro-3-ethynylbenzoate, methyl 4-amino-2-chloro-5-isobutyl-3-((trimethylsilyl)ethynyl) benzoate replacing methyl 4-amino-2-chloro-3-((trimethylsilyl)ethynyl)benzoate.
LC-MS (A): $t_R$=0.94 min; [M+H]+: 266.07

A.15.e. Methyl 4-chloro-7-isobutyl-1H-indole-5-carboxylate

This compound was prepared using a method analogous to that of methyl 4-chloro-1H-indole-5-carboxylate, methyl 4-amino-2-chloro-3-ethynyl-5-isobutylbenzoate replacing methyl 4-amino-2-chloro-3-ethynylbenzoate.
LC-MS (A): $t_R$=0.94 min; [M+H]+: 266.16

A.15.f. 4-Chloro-7-isobutyl-1H-indole-5-carboxylic acid

This compound was prepared using a method analogous to that of 4-chloro-7-methyl-1H-indole-5-carboxylic acid, methyl 4-chloro-7-isobutyl-1H-indole-5-carboxylate replacing methyl 4-chloro-7-methyl-1H-indole-5-carboxylate.
LC-MS (A): $t_R$=0.82 min, [M+H]+: 252.06

A.16. Synthesis of 4-chloro-7-(3-methoxypropyl)-1H-indole-5-carboxylic acid

A.16.a. Methyl 4-amino-2-chloro-5-(3-methoxyprop-1-yn-1-yl)benzoate

To a mixture of methyl 4-amino-2-chloro-5-iodobenzoate (3.51 mmol), Pd(PPh$_3$)$_2$Cl$_2$ (0.18 mmol) and CuI (0.18 mmol) was sequentially added under argon THF (12 mL), Et$_3$N (14 mmol) and methyl propargyl ether (14 mmol). The mixture was stirred for 1 h at RT, diluted with EtOAc and filtered. The filtrate was concentrated in vacuo and the crude was purified by CC (SNAP KP-Sil™ from Biotage) using Hept/EtOAc from 85/15 to 40/60 to give the title compound as orange solid.
LC-MS (A): $t_R$=0.82 min, [M+H]+: 253.99

A.16.b. Methyl 4-amino-2-chloro-5-(3-methoxypropyl)benzoate

To a solution of methyl 4-amino-2-chloro-5-(3-methoxyprop-1-yn-1-yl)benzoate (3.48 mmol) in EtOH (14 mL) was added PtO$_2$ (0.35 mmol). The mixture was stirred under a hydrogen atmosphere for 2 h. It was filtered over Celite, washed with EtOH and concentrated in vacuo. The crude was purified by CC (SNAP KP-Sil™ from Biotage) using Hept/EtOAc from 1/0 to 8/2 to give the title compound as yellow oil.
LC-MS (A): $t_R$=0.80 min, [M+H]+: 257.90

A.16.c. Methyl 4-amino-2-chloro-3-iodo-5-(3-methoxypropyl)benzoate

This compound was prepared using a method analogous to that of the mixture of methyl 4-amino-2-chloro-3-iodobenzoate and methyl 4-amino-2-chloro-5-iodobenzoate, methyl 4-amino-2-chloro-5-(3-methoxypropyl)benzoate replacing methyl 4-amino-2-chlorobenzoate.
LC-MS (A): $t_R$=0.90 min; [M+H]+: 383.91

A.16.d. Methyl 4-amino-2-chloro-5-(3-methoxypropyl)-3-(trimethylsilyl)ethynyl)benzoate This compound was prepared using a method analogous to that of methyl 4-amino-2-chloro-3-((trimethylsilyl)ethynyl)benzoate, methyl 4-amino-2-chloro-3-iodo-5-(3-methoxypropyl)benzoate replacing the mixture of methyl 4-amino-2-chloro-3-iodobenzoate and methyl 4-amino-2-chloro-5-iodobenzoate.
LC-MS (A): $t_R$=1.00 min; [M+H]+: 353.85

A.16.e. Methyl 4-amino-2-chloro-3-ethynyl-5-(3-methoxypropyl)benzoate

This compound was prepared using a method analogous to that of methyl 4-amino-2-chloro-3-ethynylbenzoate, methyl 4-amino-2-chloro-5-(3-methoxypropyl)-3-((trimethylsilyl) ethynyl)benzoate replacing methyl 4-amino-2-chloro-3-((trimethylsilyl)ethynyl)benzoate.
LC-MS (A): $t_R$=0.85 min; [M+H]+: 281.83

A.16.f. Methyl 4-chloro-7-(3-methoxypropyl)-1H-indole-5-carboxylate

This compound was prepared using a method analogous to that of methyl 4-chloro-1H-indole-5-carboxylate, methyl 4-amino-2-chloro-3-ethynyl-5-(3-methoxypropyl)benzoate replacing methyl 4-amino-2-chloro-3-ethynylbenzoate.
LC-MS (A): $t_R$=0.86 min; [M+H]+: 282.07

A.16.g. 4-Chloro-7-(3-methoxypropyl)-1H-indole-5-carboxylic acid

This compound was prepared using a method analogous to that of 4-chloro-7-methyl-1H-indole-5-carboxylic acid, methyl 4-chloro-7-(3-methoxypropyl)-1H-indole-5-carboxylate replacing methyl 4-chloro-7-methyl-1H-indole-5-carboxylate.
LC-MS (A): $t_R$=0.72 min, [M+H]+: 268.07

A.17. Synthesis of 4-methyl-1H-indole-5-carboxylic acid

A.17.a. Methyl 4-methyl-1H-indole-5-carboxylate

Methyl 4-chloro-1H-indole-5-carboxylate (0.48 mmol), K$_2$CO$_3$ (1.91 mmol) and PEPPSI™-IPr (0.05 mmol) were placed in a pressure vessel and anh. dioxane (2 mL) and trimethylboroxine (0.23 mL) were added sequentially. The tube was sealed under argon and heated at 115° C. After 17 h, the reaction mixture was cooled to RT, filtered over a pad of Celite and the cake was washed with EtOAc. The filtrate was concentrated in vacuo and the crude was purified by CC (SNAP KP-Sil™ from Biotage) using Hept/EtOAc from 96/4 to 50/50 to give the title compound as white solid.
LC-MS (A): $t_R$=0.78 min, [M+H]+: 190.10

A.17.b. 4-Methyl-1H-indole-5-carboxylic acid

This compound was prepared using a method analogous to that of 4-chloro-7-methyl-1H-indole-5-carboxylic acid, methyl 4-methyl-1H-indole-5-carboxylate replacing methyl 4-chloro-7-methyl-1H-indole-5-carboxylate except that the reaction mixture was stirred for 16 h at 60° C.
LC-MS (A): $t_R$=0.64 min
LC-MS (D*): $t_R$=0.15 min, [M–H]–: 173.91

A.18. Synthesis of 4-chloro-7-methoxy-1H-indole-5-carboxylic acid

A.18.a.1-Chloro-4-methoxy-2-methyl-5-nitrobenzene

To a suspension of 4-chloro-5-methyl-2-nitrophenol (5.33 mmol) and $K_2CO_3$ (10.70 mmol) in DMF (11 mL) was added methyl iodide (5.86 mmol) and the mixture was stirred for 6 h at RT. It was quenched with half saturated $NaHCO_3$ solution and extracted three times with EtOAc. The organic phases were dried over $MgSO_4$ and concentrated in vacuo. The crude was purified by CC (Isolute Flash Si II from Biotage) using Hept/EtOAc from 85/15 to 80/20 to give the title compound as yellow solid.
LC-MS (A): $t_R$=0.88 min
$^1$H NMR (($CD_3$)$_2$SO) δ: 8.01 (s, 1 H), 7.44 (s, 1 H), 3.93 (s, 3 H), 2.42 (s, 3 H)

A.18.b. 2-Chloro-5-methoxy-4-nitrobenzoic acid

To a suspension of 1-chloro-4-methoxy-2-methyl-5-nitrobenzene (4.32 mmol) in $H_2O$ (207 mL) was added $KMnO_4$ (17.30 mmol) and the mixture was refluxed for 3 h and filtered to remove solids. The filtrate was quenched with a 40% $NaHSO_3$ solution, acidified with a 1M HCl solution until pH 1-2 and extracted three times with EtOAc. The organic phases were dried over $MgSO_4$ and concentrated in vacuo to give the title compound as light yellow solid.
LC-MS (A): $t_R$=0.69 min
LC-MS (D*): $t_R$=0.26 min, [M–H]–: 230.04

A.18.c. 4-Amino-2-chloro-5-methoxybenzoic acid

This compound was prepared using a method analogous to that of methyl 4-amino-2,6-dichlorobenzoate, 2-chloro-5-methoxy-4-nitrobenzoic acid replacing methyl 2,6-dichloro-4-nitrobenzoate except that the mixture was heated for 15 min at 100° C. under microwave conditions.
LC-MS (A): $t_R$=0.59 min; [M+$CH_3$CN+H]+: 242.70

A.18.d. Methyl 4-amino-2-chloro-5-methoxybenzoate

This compound was prepared using a method analogous to that of methyl 4-amino-2-chlorobenzoate, 4-amino-2-chloro-5-methoxybenzoic acid replacing 4-amino-2-chlorobenzoic acid.
LC-MS (A): $t_R$=0.75 min; [M+H]+: 216.14

A.18.e. Methyl 4-amino-2-chloro-3-iodo-5-methoxybenzoate

This compound was prepared using a method analogous to that of the mixture of methyl 4-amino-2-chloro-3-iodobenzoate and methyl 4-amino-2-chloro-5-iodobenzoate, methyl 4-amino-2-chloro-5-methoxybenzoate replacing methyl 4-amino-2-chlorobenzoate.
LC-MS (A): $t_R$=0.85 min; [M+H]+: 341.67

A.18.f. Methyl 4-amino-2-chloro-5-methoxy-3-(trimethylsilyl)ethynyl)benzoate

This compound was prepared using a method analogous to that of methyl 4-amino-2-chloro-3-((trimethylsilyl)ethynyl)benzoate, methyl 4-amino-2-chloro-3-iodo-5-methoxybenzoate replacing the mixture of methyl 4-amino-2-chloro-3-iodobenzoate and methyl 4-amino-2-chloro-5-iodobenzoate.
LC-MS (A): $t_R$=0.99 min; [M+H]+: 311.94

A.18.g. Methyl 4-amino-2-chloro-3-ethynyl-5-methoxybenzoate

This compound was prepared using a method analogous to that of methyl 4-amino-2-chloro-3-ethynylbenzoate, methyl 4-amino-2-chloro-5-methoxy-3-((trimethylsilyl)ethynyl)-benzoate replacing methyl 4-amino-2-chloro-3-((trimethylsilyl)ethynyl)benzoate.
LC-MS (A): $t_R$=0.81 min; [M+H]+: 240.02

A.18.h. Methyl 4-chloro-7-methoxy-1H-indole-5-carboxylate

This compound was prepared using a method analogous to that of methyl 4-chloro-1H-indole-5-carboxylate, methyl 4-amino-2-chloro-3-ethynyl-5-methoxybenzoate replacing methyl 4-amino-2-chloro-3-ethynylbenzoate.
LC-MS (A): $t_R$=0.82 min; [M+H]+: 239.95

A.18.i. 4-Chloro-7-methoxy-1H-indole-5-carboxylic acid

This compound was prepared using a method analogous to that of 4-chloro-7-methyl-1H-indole-5-carboxylic acid, methyl 4-chloro-7-methoxy-1H-indole-5-carboxylate replacing methyl 4-chloro-7-methyl-1H-indole-5-carboxylate.
LC-MS (A): $t_R$=0.68 min, [M+H]+: 226.08

A.19. Synthesis of 4,7-dimethyl-1H-indole-5-carboxylic acid

A.19.a.4-Amino-2,5-dimethylbenzonitrile

4-Bromo-2,5-dimethylaniline (5 mmol), zinc cyanide (6 mmol) and Pd(PPh$_3$)$_4$ (0.1 mmol) were placed in a pressure vessel and anh. DMF (3 mL) was added. The tube was sealed under argon and heated at 110° C. After 35 h, it was quenched with a 10% $Na_2CO_3$ solution and extracted three times with EtOAc. The organic phase was washed with a sat. $NaHCO_3$ solution, dried over $MgSO_4$ and concentrated in vacuo. The crude was purified by CC (SNAP KP-Sil™ from Biotage) using Hept/EtOAc from 92/8 to 40/60 to give the title compound as white solid.
LC-MS (A): $t_R$=0.72 min, [M+H]+: 147.16

A.19.b. 4-Amino-3-iodo-2,5-dimethylbenzonitrile

This compound was prepared using a method analogous to that of the mixture of methyl 4-amino-2-chloro-3-iodobenzoate and methyl 4-amino-2-chloro-5-iodobenzoate, 4-amino-2,5-dimethylbenzonitrile replacing methyl 4-amino-2-chlorobenzoate.
LC-MS (A): $t_R$=0.85 min; [M+$CH_3$CN+H]+: 313.83

A.19.c. 4-Amino-2,5-dimethyl-3-(trimethylsilyl)ethynyl)benzonitrile

This compound was prepared using a method analogous to that of methyl 4-amino-2-chloro-3-((trimethylsilyl)ethynyl)benzoate, 4-amino-3-iodo-2,5-dimethylbenzonitrile replacing the mixture of methyl 4-amino-2-chloro-3-iodobenzoate and methyl 4-amino-2-chloro-5-iodobenzoate.

LC-MS (A): $t_R$=1.00 min; [M+H]+: 243.13

A.19.d. 4-Amino-3-ethynyl-2,5-dimethylbenzonitrile

This compound was prepared using a method analogous to that of methyl 4-amino-2-chloro-3-ethynylbenzoate, 4-amino-2,5-dimethyl-3-((trimethylsilyl)ethynyl)benzonitrile replacing methyl 4-amino-2-chloro-3-((trimethylsilyl)ethynyl)benzoate.

LC-MS (A): $t_R$=0.81 min; [M+CH$_3$CN+H]+: 212.12

A.19.e. 4,7-Dimethyl-1H-indole-5-carbonitrile

This compound was prepared using a method analogous to that of methyl 4-chloro-1H-indole-5-carboxylate, 4-amino-3-ethynyl-2,5-dimethylbenzonitrile replacing methyl 4-amino-2-chloro-3-ethynylbenzoate.

LC-MS (A): $t_R$=0.81 min; [M+CH$_3$CN+H]+: 212.13

$^1$H NMR ((CD$_3$)$_2$SO) δ: 11.64 (s br, 1 H), 7.52 (dd, J$_1$=J$_2$=2.8 Hz, 1 H), 7.17 (s, 1 H), 6.67 (dd, J$_1$=2.9 Hz, J$_2$=1.9 Hz, 1 H), 2.63 (s, 3 H), 2.47 (s, 3 H)

A.19.f. 4,7-Dimethyl-1H-indole-5-carboxylic acid

To a solution of 4,7-dimethyl-1H-indole-5-carbonitrile (0.19 mmol) in EtOH (1 mL) was added a 4M KOH solution (3.9 mL) and the mixture was heated for 18 h at 120° C. It was partitioned between water and EtOAc, the aqueous phase was acidified with a 25% HCl solution until pH 1-2 and extracted three times with EtOAc. The organic phases were dried over MgSO$_4$ and concentrated in vacuo to give the title compound as white solid.

LC-MS (A): $t_R$=0.68 min; [M+H]+: 190.18

A.20. Synthesis of 4-ethyl-1H-indole-5-carboxylic acid

A.20.a. Methyl 4-ethyl-1H-indole-5-carboxylate

This compound was prepared using a method analogous to that of methyl 4-methyl-1H-indole-5-carboxylate, vinylboronic acid pinacol ester replacing trimethylboroxine.

LC-MS (A): $t_R$=0.80 min, [M+H]+: 202.20

A.20.b. Methyl 4-ethyl-1H-indole-5-carboxylate

To a solution of methyl 4-vinyl-1H-indole-5-carboxylate (0.21 mmol) in EtOH (2 mL) was added platinum dioxide (0.021 mmol). The mixture was stirred under a hydrogen atmosphere for 2 h, filtered over Celite and concentrated in vacuo to give the title compound as pinkish solid.

LC-MS (A): $t_R$=0.83 min, [M+H]+: 204.18

A.20.c. 4-Ethyl-1H-indole-5-carboxylic acid

This compound was prepared using a method analogous to that of 4-chloro-7-methyl-1H-indole-5-carboxylic acid, methyl 4-ethyl-1H-indole-5-carboxylate replacing methyl 4-chloro-7-methyl-1H-indole-5-carboxylate.

LC-MS (A): $t_R$=0.70 min, [M+CH$_3$CN+H]+: 231.08

A.21. Synthesis of 4-chloro-7-acetyl-1H-indole-5-carboxylic acid

A.21.a. Methyl 4-amino-2-chloro-3,5-diiodobenzoate

To a suspension of methyl 4-amino-2-chlorobenzoate (10.8 mmol) in EtOH (100 mL) was added iodine (23.7 mmol) and silver sulfate (10.8 mmol) under argon. The mixture was stirred for 2 h, filtered and the filtrate was treated with a 10% aq. solution of sodium thiosulfate. After evaporation of EtOH, the residue was partitioned between EtOAc and a 1M aq. solution of NaOH. The organic phase was washed with a 1M aq. solution of NaOH and brine, dried over MgSO$_4$ and concentrated in vacuo. The crude was purified by CC using DCM and the solid was triturated in CH$_3$CN and filtered to give the title compound as beige solid.

LC-MS (A): $t_R$=0.92 min $^1$H NMR ((CD$_3$)$_2$SO) δ: 8.13 (s, 1 H), 6.02 (s, 2 H), 3.79 (s, 3 H)

A.21.b. Methyl 4-amino-2-chloro-3-iodo-5-(trimethylsilyl)ethynyl)benzoate

A solution of methyl 4-amino-2-chloro-3,5-diiodobenzoate (9.6 mmol) in Et$_3$N (80 mL) and toluene (80 mL) was treated under argon with PPh$_3$ (0.96 mmol), CuI (4.80 mmol), Pd(PPh$_3$)$_2$Cl$_2$ (0.48 mmol) and trimethylsilylacetylene (10.1 mmol). The mixture was stirred for 2 h at RT, quenched with a 10% aq. solution of NH$_4$Cl and extracted with EtOAc. The organic phase was washed with brine, dried over MgSO$_4$ and concentrated in vacuo. The crude was purified by CC (SNAP KP-SIL™ from Biotage) using Hept/EtOAc from 100/0 to 85/15 to give the title compound as light orange solid.

LC-MS (A): $t_R$=1.05 min; [M+H]+: 408.02

A.21.c. Methyl 5-acetyl-4-amino-2-chloro-3-iodobenzoate

A solution of methyl 4-amino-2-chloro-3-iodo-5-((trimethylsilyl)ethynyl)benzoate (4.39 mmol) in toluene (20 mL) was treated with 4-toluene sulfonic acid monohydrate (11 mmol). The mixture was stirred for 3 h at 80° C. and poured into water. The aq. phase was basified with a 32% aq. solution of NaOH until pH=12-13 and extracted with EtOAc. The organic phase was washed with brine, dried over MgSO$_4$ and concentrated in vacuo. The crude was purified by CC (SNAP KP-SIL™ from Biotage) using Hept/EtOAc from 100/0 to 75/25 to give the title compound as light yellow solid.

LC-MS (A): $t_R$=0.88 min $^1$H NMR ((CD$_3$)$_2$SO) δ: 8.37 (s, 1 H), 8.00 (s br, 2 H), 3.83 (s, 3 H), 2.63 (s, 3 H)

A.21.d. Methyl 5-acetyl-4-amino-2-chloro-3-((trimethylsilyl)ethynyl)benzoate This compound was prepared using a method analogous to that of methyl 4-amino-2-chloro-3-((trimethylsilyl)ethynyl)benzoate, methyl 5-acetyl-4-amino-2-chloro-3-iodobenzoate replacing the mixture of methyl 4-amino-2-chloro-3-iodobenzoate and methyl 4-amino-2-chloro-5-iodobenzoate.
LC-MS (A): $t_R$=1.03 min; [M+H]+: 324.25

A.21.e. Methyl 5-acetyl-4-amino-2-chloro-3-ethynylbenzoate

This compound was prepared using a method analogous to that of methyl 4-amino-2-chloro-3-ethynylbenzoate, methyl 5-acetyl-4-amino-2-chloro-3-((trimethylsilyl)ethynyl) benzoate replacing methyl 4-amino-2-chloro-3-((trimethylsilyl)ethynyl)benzoate.
LC-MS (A): $t_R$=0.84 min; [M+H]+: 251.99

A.21.f. Methyl 7-acetyl-4-chloro-1H-indole-5-carboxylate

This compound was prepared using a method analogous to that of methyl 4-chloro-1H-indole-5-carboxylate, methyl 5-acetyl-4-amino-2-chloro-3-ethynylbenzoate replacing methyl 4-amino-2-chloro-3-ethynylbenzoate.
LC-MS (A): $t_R$=0.83 min
$^1$H NMR ((CD$_3$)$_2$SO) δ: 11.96 (s, 1 H), 8.32 (s, 1 H), 7.56 (dd, $J_1$=$J_2$=2.9 Hz, 1 H), 6.74 (dd, $J_1$=2.1 Hz, $J_2$=3.2 Hz, 1 H), 3.92 (s, 3 H), 2.72 (s, 3 H)

A.21.g. 7-Acetyl-4-chloro-1H-indole-5-carboxylic acid

This compound was prepared using a method analogous to that of 4-chloro-7-methyl-1H-indole-5-carboxylic acid, methyl 7-acetyl-4-chloro-1H-indole-5-carboxylate replacing methyl 4-chloro-7-methyl-1H-indole-5-carboxylate.
LC-MS (A): $t_R$=0.69 min
$^1$H NMR ((CD$_3$)$_2$SO) δ: 13.25 (s, 1 H), 11.91 (s, 1 H), 8.34 (s, 1 H), 7.54 (dd, $J_1$=$J_2$=2.9 Hz, 1 H), 6.72 (dd, $J_1$=2.1 Hz, $J_2$=3.1 Hz, 1 H), 2.72 (s, 3 H)

A.22. Synthesis of 7-methyl-4-(trifluoromethyl)-1H-indole-5-carboxylic acid

A.22.a. Methyl 4-amino-2-(trifluoromethyl)benzoate

This compound was prepared using a method analogous to that of methyl 4-amino-2-chlorobenzoate, 4-amino-2-(trifluoromethyl)benzoic acid replacing 4-amino-2-chlorobenzoic acid.
LC-MS (A): $t_R$=0.77 min, [M+H]+: 220.04

A.22.b. Methyl 4-amino-5-iodo-2-(trifluoromethyl)benzoate

This compound was prepared using a method analogous to that of the mixture of methyl 4-amino-2-chloro-3-iodobenzoate and methyl 4-amino-2-chloro-5-iodobenzoate, methyl 4-amino-2-(trifluoromethyl)benzoate replacing methyl 4-amino-2-chlorobenzoate except that only the 5-iodo regioisomer was isolated.
LC-MS (A): $t_R$=0.88 min, [M+H]+: 345.7

A.22.c. Methyl 4-amino-5-methyl-2-(trifluoromethyl)benzoate

To a solution of methyl 4-amino-5-iodo-2-(trifluoromethyl)benzoate (24.6 mmol) in dioxane (49 mL) was added under argon a 2M solution of methylzinc chloride in THF (61.6 mmol) followed by Pd(dppf)Cl$_2$.DCM (1.72 mmol). The mixture was stirred for 30 min at 65° C. in a sealed vial, diluted with EtOAc and filtered. The filtrate was washed with a sat. solution of Rochelle salt and with brine, dried over MgSO$_4$ and concentrated in vacuo. The crude was purified by CC (SNAP KP-SIL™ from Biotage) using DCM to give the title compound as brown solid.
LC-MS (A): $t_R$=0.81 min; [M+H]+: 234.01

A.22.d. Methyl 4-amino-3-iodo-5-methyl-2-(trifluoromethyl)benzoate

This compound was prepared using a method analogous to that of the mixture of methyl 4-amino-2-chloro-3-iodobenzoate and methyl 4-amino-2-chloro-5-iodobenzoate, methyl 4-amino-5-methyl-2-(trifluoromethyl)benzoate replacing methyl 4-amino-2-chlorobenzoate except that the reaction mixture was stirred for 7 h at 50° C.
LC-MS (A): $t_R$=0.88 min, [M+H]+: 400.78

A.22.e. Methyl 4-amino-5-methyl-2-(trifluoromethyl)-3-(trimethylsilyl)ethynyl)benzoate This compound was prepared using a method analogous to that of methyl 4-amino-2-chloro-3-((trimethylsilyl)ethynyl)benzoate, methyl 4-amino-3-iodo-5-methyl-2-(trifluoromethyl)benzoate replacing the mixture of methyl 4-amino-2-chloro-3-iodobenzoate and methyl 4-amino-2-chloro-5-iodobenzoate except that the reaction mixture was stirred for 3 h 30 at 70° C.
LC-MS (A): $t_R$=1.02 min; [M+H]+: 330.09

A.22.f. Methyl 4-amino-3-ethynyl-5-methyl-2-(trifluoromethyl)benzoate

This compound was prepared using a method analogous to that of methyl 4-amino-2-chloro-3-ethynylbenzoate, methyl 4-amino-5-methyl-2-(trifluoromethyl)-3-((trimethylsilyl) ethynyl)benzoate replacing methyl 4-amino-2-chloro-3-((trimethylsilyl)ethynyl)benzoate.
LC-MS (A): $t_R$=0.85 min; [M+H]+: 257.90

A.22.g. Methyl 7-methyl-4-(trifluoromethyl)-1H-indole-5-carboxylate

This compound was prepared using a method analogous to that of methyl 4-chloro-1H-indole-5-carboxylate, methyl 4-amino-3-ethynyl-5-methyl-2-(trifluoromethyl)benzoate replacing methyl 4-amino-2-chloro-3-ethynylbenzoate.
LC-MS (A): $t_R$=0.86 min
$^1$H NMR ((CD$_3$)$_2$SO) δ: 11.87 (s, 1 H), 7.68 (dd, $J_1$=$J_2$=2.8 Hz, 1 H), 7.22 (s, 1 H), 6.65 (m, 1 H), 3.85 (s, 3 H), 2.58 (s, 3 H)

A.22.h. 7-Methyl-4-(trifluoromethyl)-1H-indole-5-carboxylic acid

This compound was prepared using a method analogous to that of 4-chloro-7-methyl-1H-indole-5-carboxylic acid, methyl 7-methyl-4-(trifluoromethyl)-1H-indole-5-carboxylate replacing methyl 4-chloro-7-methyl-1H-indole-5-carboxylate except that the reaction mixture was stirred ON at 60° C.
LC-MS (A): $t_R$=0.73 min
$^1$H NMR ((CD$_3$)$_2$SO) δ: 13.07 (s br, 1 H), 11.79 (s, 1 H), 7.65 (dd, $J_1$=$J_2$=2.7 Hz, 1 H), 7.21 (s, 1 H), 6.63 (m, 1 H), 2.57 (s, 3 H)

A.23. Synthesis of 4-chloro-7-ethyl-1H-indole-5-carboxylic acid

A.23.a. Methyl 4-amino-2-chloro-5-ethynyl-3-iodobenzoate

This compound was prepared using a method analogous to that of methyl 4-amino-2-chloro-3-ethynylbenzoate, methyl 4-amino-2-chloro-3-iodo-5-((trimethylsilyl)ethynyl) benzoate replacing methyl 4-amino-2-chloro-3-((trimethylsilyl)ethynyl)benzoate.

LC-MS (A): $t_R$=0.88 min
$^1$H NMR ((CD$_3$)$_2$SO) δ: 7.76 (s, 1 H), 6.17 (s, 2 H), 4.65 (s, 1 H), 3.78 (s, 3 H)

A.23.b. Methyl 4-amino-2-chloro-5-ethyl-3-iodobenzoate

To a solution of methyl 4-amino-2-chloro-5-ethynyl-3-iodobenzoate (0.99 mmol) in EtOH (4 mL) was added platinum (IV) oxide (0.099 mmol). The mixture was stirred under a hydrogen atmosphere for 1 h, filtered over Celite and concentrated in vacuo. The crude was purified by CC using DCM to give the title compound as light yellow solid.

LC-MS (A): $t_R$=0.90 min, [M+H]+: 339.83

A.23.c. Methyl 4-amino-2-chloro-5-ethyl-3-(trimethylsilyl)ethynyl)benzoate

This compound was prepared using a method analogous to that of methyl 4-amino-2-chloro-3-((trimethylsilyl)ethynyl)benzoate, methyl 4-amino-2-chloro-5-ethyl-3-iodobenzoate replacing the mixture of methyl 4-amino-2-chloro-3-iodobenzoate and methyl 4-amino-2-chloro-5-iodobenzoate except that the reaction was stirred for 30 min at 80° C.

LC-MS (A): $t_R$=1.03 min; [M+H]+: 310.22

A.23.d. Methyl 4-amino-2-chloro-5-ethyl-3-ethynylbenzoate

This compound was prepared using a method analogous to that of methyl 4-amino-2-chloro-3-ethynylbenzoate, methyl 4-amino-2-chloro-5-ethyl-3-((trimethylsilyl)ethynyl) benzoate replacing methyl 4-amino-2-chloro-3-((trimethylsilyl)ethynyl)benzoate.

LC-MS (A): $t_R$=0.86 min; [M+H]+: 238.21

A.23.e. Methyl 4-chloro-7-ethyl-1H-indole-5-carboxylate

This compound was prepared using a method analogous to that of methyl 4-chloro-1H-indole-5-carboxylate, methyl 4-amino-2-chloro-5-ethyl-3-ethynylbenzoate replacing methyl 4-amino-2-chloro-3-ethynylbenzoate.

LC-MS (A): $t_R$=0.86 min, [M+H]+: 238.05

A.23.f. 4-Chloro-7-ethyl-1H-indole-5-carboxylic acid

This compound was prepared using a method analogous to that of 4-chloro-7-methyl-1H-indole-5-carboxylic acid, methyl 7-methyl-4-(trifluoromethyl)-1H-indole-5-carboxylate replacing methyl 4-chloro-7-methyl-1H-indole-5-carboxylate.

LC-MS (A): $t_R$=0.73 min, [M+H]+: 224.20

A.24. Synthesis of 7-chloro-4-methyl-1H-indole-5-carboxylic acid

A.24.a. Methyl 4-acetamido-5-chloro-2-(((trifluoromethyl)sulfonyl) oxy)benzoate To a solution of methyl 4-acetamido-5-chloro-2-hydroxybenzoate (20.5 mmol) in DCM (100 mL) was added at 0° C. Et$_3$N (22.6 mmol) and trifluoromethanesulfonic anhydride (22.6 mmol). The mixture was stirred for 1 h at RT, quenched with a sat. solution of NaHCO$_3$ and extracted with DCM. The organic phase was washed with brine, dried over MgSO$_4$ and concentrated in vacuo. The crude was purified by CC (SNAP KP-Sil™ from Biotage) using Hept/EtOAc from 100/0 to 65/35 to give the title compound as light yellow solid.

LC-MS (A): $t_R$=0.90 min
$^1$H NMR ((CD$_3$)$_2$SO) δ: 9.94 (s, 1 H), 8.35 (s, 1 H), 8.14 (s, 1 H), 3.88 (s, 3 H), 2.23 (s, 3 H)

A.24.b. Methyl 4-acetamido-5-chloro-2-methylbenzoate

A suspension of methyl 4-acetamido-5-chloro-2-(((trifluoromethyl)sulfonyl)oxy)benzoate (2.61 mmol), K$_3$PO$_4$ (5.23 mmol), methylboronic acid (5.23 mmol) and Pd(dppf) Cl$_2$.DCM (0.26 mmol) in THF (26 mL) was stirred under argon for 2 h at 65° C. The reaction mixture was quenched with a sat. solution of NaHCO$_3$ and extracted three times with EtOAc. The organic phase was washed with brine, dried over MgSO$_4$ and concentrated in vacuo. The crude was purified by CC (SNAP KP-Sil™ from Biotage) using Hept/ EtOAc from 100/0 to 60/40 to give the title compound as white solid.

LC-MS (A): $t_R$=0.77 min, [M+H]+: 241.90

A.24.c. Methyl 4-amino-5-chloro-2-methylbenzoate

To a solution of methyl 4-acetamido-5-chloro-2-methylbenzoate (2.25 mmol) in MeOH (14 mL) was added K$_2$CO$_3$ (2.48 mmol). The suspension was stirred for 3 days at RT, MeOH was evaporated off and the residue was partitioned between EtOAc and a 1M solution of HCl. The aq. phase was extracted twice with EtOAc and the combined organic phases were washed with brine, dried over MgSO$_4$ and concentrated in vacuo. The crude was purified by CC (SNAP KP-Sil™ from Biotage) using Hept/EtOAc from 100/0 to 80/20 to give the title compound as white solid.

LC-MS (A): $t_R$=0.81 min, [M+H]+: 200.12

A.24.d. Methyl 4-amino-5-chloro-3-iodo-2-methylbenzoate

This compound was prepared using a method analogous to that of the mixture of methyl 4-amino-2-chloro-3-iodobenzoate and methyl 4-amino-2-chloro-5-iodobenzoate, methyl 4-amino-5-chloro-2-methylbenzoate replacing methyl 4-amino-2-chlorobenzoate except that the reaction mixture was stirred for 1 h at RT.

LC-MS (A): $t_R$=0.91 min
$^1$H NMR ((CD$_3$)$_2$SO) δ: 7.76 (s, 1 H), 6.02 (s, 2 H), 3.77 (s, 3 H), 2.65 (s, 3 H)

A.24.e. Methyl 4-amino-5-chloro-2-methyl-3-(trimethylsilyl)ethynyl)benzoate This compound was prepared using a method analogous to that of methyl 4-amino-2-chloro-3-((trimethylsilyl)ethynyl)benzoate, methyl 4-amino-5-chloro-3-iodo-2-methyl benzoate replacing the mixture of methyl 4-amino-2-chloro-3-iodobenzoate and methyl 4-amino-2-chloro-5-iodobenzoate.

LC-MS (A): $t_R$=1.06 min; [M+H]+: 296.14

A.24.f. Methyl 4-amino-5-chloro-3-ethynyl-2-methylbenzoate

This compound was prepared using a method analogous to that of methyl 4-amino-2-chloro-3-ethynylbenzoate, methyl 4-amino-5-chloro-2-methyl-3-((trimethylsilyl)ethynyl)benzoate replacing methyl 4-amino-2-chloro-3-((trimethylsilyl)ethynyl)benzoate.

LC-MS (A): $t_R$=0.88 min; [M+H]+: 224.03

A.24.g. Methyl 7-chloro-4-methyl-1H-indole-5-carboxylate

This compound was prepared using a method analogous to that of methyl 4-chloro-1H-indole-5-carboxylate, methyl 4-amino-5-chloro-3-ethynyl-2-methylbenzoate replacing methyl 4-amino-2-chloro-3-ethynylbenzoate.

LC-MS (A): $t_R$=0.86 min, [M+H]+: 223.46

A.24.h. 7-Chloro-4-methyl-1H-indole-5-carboxylic acid

This compound was prepared using a method analogous to that of 4-chloro-7-methyl-1H-indole-5-carboxylic acid, methyl 7-chloro-4-methyl-1H-indole-5-carboxylate replacing methyl 4-chloro-7-methyl-1H-indole-5-carboxylate.

LC-MS (A): $t_R$=0.72 min
$^1$H NMR ((CD$_3$)$_2$SO) δ: 12.62 (s, 1 H), 11.77 (s, 1 H), 7.67 (s, 1 H), 7.49 (dd, J$_1$=J$_2$=2.8 Hz, 1 H), 6.78 (dd, J$_1$=2.0 Hz, J$_2$=3.0 Hz, 1 H), 2.75 (s, 3 H)

A.25. Synthesis of 7-methoxy-4-methyl-1H-indole-5-carboxylic acid

A.25.a. 5-Methoxy-2-methyl-4-nitrobenzonitrile

This compound was prepared using a method analogous to that of 2-chloro-6-methyl-4-nitrobenzonitrile, 5-methoxy-2-methyl-4-nitroaniline replacing 2-chloro-6-methyl-4-nitroaniline except that the reaction mixture was stirred for 1 h at 85° C. and ON at RT.

LC-MS (A): $t_R$=0.82 min
$^1$H NMR ((CD$_3$)$_2$SO) δ: 8.00 (s, 1H), 7.88 (s, 1H), 3.95 (s, 3H), 2.47 (s, 3H)

A.25.b. 5-Methoxy-2-methyl-4-nitrobenzoic acid

This compound was prepared using a method analogous to that of 2-chloro-6-methyl-4-nitrobenzoic acid, 5-methoxy-2-methyl-4-nitrobenzonitrile replacing 2-chloro-6-methyl-4-nitrobenzonitrile.

LC-MS (A): $t_R$=0.82 min
LC-MS (D*): $t_R$=0.17 min; [M−H]−: 210.19

A.25.c. Methyl 5-methoxy-2-methyl-4-nitrobenzoate

This compound was prepared using a method analogous to that of methyl 4-amino-2-chlorobenzoate, 5-methoxy-2-methyl-4-nitrobenzoic acid replacing 4-amino-2-chlorobenzoic acid.

LC-MS (A): $t_R$=0.85 min
$^1$H NMR ((CD$_3$)$_2$SO) δ: 7.87 (s, 1 H), 7.64 (s, 1 H), 3.95 (s, 3 H), 3.89 (s, 3 H), 2.46 (s, 3 H)

A.25.d. Methyl 4-amino-5-methoxy-2-methylbenzoate

To a solution of methyl 5-methoxy-2-methyl-4-nitrobenzoate (2.13 mmol) in MeOH (21 mL) was added zinc dust (21.3 mmol) at RT followed by ammonium formate (21.3 mmol) at 0° C. The mixture was stirred for 1 h at RT, filtered over Celite and the filtrate was concentrated in vacuo. The residue was partitioned between EtOAc and a sat. solution of NaHCO$_3$. The organic phase was washed with brine, dried over MgSO$_4$ and concentrated in vacuo. The crude was purified by CC using DCM/MeOH from 100/0 to 99/1 to give the title compound as light yellow solid.

LC-MS (A): $t_R$=0.71 min; [M+H]+: 196.15

A.25.e. Methyl 4-amino-3-iodo-5-methoxy-2-methylbenzoate

This compound was prepared using a method analogous to that of the mixture of methyl 4-amino-2-chloro-3-iodobenzoate and methyl 4-amino-2-chloro-5-iodobenzoate, methyl 4-amino-5-methoxy-2-methylbenzoate replacing methyl 4-amino-2-chlorobenzoate except that the reaction mixture was stirred for 1 h at RT.

LC-MS (A): $t_R$=0.87 min, [M+H]+: 321.73

A.25.f. Methyl 4-amino-5-methoxy-2-methyl-3-((trimethylsilyl)ethynyl)benzoate This compound was prepared using a method analogous to that of methyl 4-amino-2-chloro-3-((trimethylsilyl)ethynyl)benzoate, methyl 4-amino-3-iodo-5-methoxy-2-methyl benzoate replacing the mixture of methyl 4-amino-2-chloro-3-iodobenzoate and methyl 4-amino-2-chloro-5-iodobenzoate.

LC-MS (A): $t_R$=1.01 min; [M+H]+: 292.21

A.25.g. Methyl 4-amino-3-ethynyl-5-methoxy-2-methylbenzoate

This compound was prepared using a method analogous to that of methyl 4-amino-2-chloro-3-ethynylbenzoate, methyl 4-amino-5-methoxy-2-methyl-3-((trimethylsilyl)ethynyl) benzoate replacing methyl 4-amino-2-chloro-3-((trimethylsilyl)ethynyl)benzoate.

LC-MS (A): $t_R$=0.83 min; [M+H]+: 220.13

A.25.h. Methyl 7-methoxy-4-methyl-1H-indole-5-carboxylate

This compound was prepared using a method analogous to that of methyl 4-chloro-1H-indole-5-carboxylate, methyl 4-amino-3-ethynyl-5-methoxy-2-methylbenzoate replacing methyl 4-amino-2-chloro-3-ethynylbenzoate.

LC-MS (A): $t_R$=0.81 min; [M+H]+: 220.07

A.25.i. 7-Methoxy-4-methyl-1H-indole-5-carboxylic acid

This compound was prepared using a method analogous to that of 4-chloro-7-methyl-1H-indole-5-carboxylic acid, methyl 7-methoxy-4-methyl-1H-indole-5-carboxylate replacing methyl 4-chloro-7-methyl-1H-indole-5-carboxylate.

LC-MS (A): $t_R$=0.67 min; [M+H]+: 206.15

A.26. Synthesis of 4-chloro-7-ethoxy-1H-indole-5-carboxylic acid

A.26.a. 4-Amino-2-chloro-5-methoxybenzonitrile

This compound was prepared using a method analogous to that of 4-amino-2,5-dimethylbenzonitrile, 4-bromo-5-chloro-2-methoxyaniline replacing 4-bromo-2,5-dimethylaniline except that the reaction mixture was stirred ON at 110° C.

LC-MS (A): $t_R$=0.76 min, [M+H]+: 183.19

A.26.b. 4-Amino-2-chloro-3-iodo-5-methoxybenzonitrile

This compound was prepared using a method analogous to that of the mixture of methyl 4-amino-2-chloro-3-iodobenzoate and methyl 4-amino-2-chloro-5-iodobenzoate, 4-amino-2-chloro-5-methoxybenzonitrile replacing methyl 4-amino-2-chlorobenzoate except that the reaction mixture was stirred for 45 min at RT.

LC-MS (A): $t_R$=0.86 min
$^1$H NMR ((CD$_3$)$_2$SO) δ: 7.33 (s, 1 H), 6.11 (s, 2 H), 3.85 (s, 3 H)

A.26.c. 4-Amino-2-chloro-5-methoxy-3-((trimethylsilyl)ethynyl)benzonitrile

This compound was prepared using a method analogous to that of methyl 4-amino-2-chloro-3-((trimethylsilyl)ethynyl)benzoate, 4-amino-2-chloro-3-iodo-5-methoxybenzonitrile replacing the mixture of methyl 4-amino-2-chloro-3-iodobenzoate and methyl 4-amino-2-chloro-5-iodobenzoate.

LC-MS (A): $t_R$=1.00 min; [M+H]+: 279.04

A.26.d. 4-Amino-2-chloro-3-ethynyl-5-methoxybenzonitrile

This compound was prepared using a method analogous to that of methyl 4-amino-2-chloro-3-ethynylbenzoate, 4-amino-2-chloro-5-methoxy-3-((tri methylsilyl)ethynyl)benzonitrile replacing methyl 4-amino-2-chloro-3-((trimethylsilyl)ethynyl)benzoate.

LC-MS (A): $t_R$=0.82 min; [M+CH$_3$CN+H]+: 248.23

A.26.e. 4-Chloro-7-methoxy-1H-indole-5-carbonitrile

This compound was prepared using a method analogous to that of methyl 4-chloro-1H-indole-5-carboxylate, 4-amino-2-chloro-3-ethynyl-5-methoxybenzonitrile replacing methyl 4-amino-2-chloro-3-ethynylbenzoate.

LC-MS (A): $t_R$=0.83 min, [M+CH$_3$CN+H]+: 248.23
$^1$H NMR ((CD$_3$)$_2$SO) δ: 12.23 (s, 1 H), 7.56 (d, J=3.1 Hz, 1 H), 7.14 (s, 1 H), 6.61 (d, J=3.1 Hz, 1 H), 3.99 (s, 3 H)

A.26.f. 4-Chloro-7-hydroxy-1H-indole-5-carbonitrile

To a solution of 4-chloro-7-methoxy-1H-indole-5-carbonitrile (2.53 mmol) in DCM (106 mL) was added dropwise a 1M solution of BBr$_3$ in DCM (14.8 mmol) at −78° C. The mixture was allowed to warm up to RT and stirred for 15 h at 45° C. then for 4 h 30 at 55° C. It was quenched with MeOH (40 mL) and concentrated in vacuo. The crude was purified by CC (SNAP KP-Sil™ from Biotage) using EtOAc/MeOH from 100/0 to 90/10 to give the title compound as brownish solid.

LC-MS (A): $t_R$=0.75 min
$^1$H NMR ((CD$_3$)$_2$SO) δ: 11.99 (s, 1 H), 10.69 (s, 1 H), 7.54 (dd, J$_1$=J$_2$=2.8 Hz, 1 H), 6.80 (s, 1 H), 6.57 (m, 1 H)

A.26.g. 4-Chloro-7-ethoxy-1H-indole-5-carbonitrile

To a solution of 4-chloro-7-hydroxy-1H-indole-5-carbonitrile (1.31 mmol) in DMF (2.6 mL) was added at 0° C. K$_2$CO$_3$ (1.58 mmol) and ethyl bromide (1.44 mmol). The mixture was stirred ON at RT, quenched with water and extracted with EtOAc. The organic phase was dried over MgSO$_4$ and concentrated in vacuo. The crude was purified by CC (SNAP KP-Sil™ from Biotage) using Hept/EtOAc from 100/0 to 50/50 to give the title compound as white solid.

LC-MS (A): $t_R$=0.88 min, [M+CH$_3$CN+H]+: 262.10

A.26.h. 4-Chloro-7-ethoxy-1H-indole-5-carboxylic acid

This compound was prepared using a method analogous to that of 4,7-dimethyl-1H-indole-5-carboxylic acid, 4-chloro-7-ethoxy-1H-indole-5-carbonitrile replacing 4,7-dimethyl-1H-indole-5-carbonitrile.

LC-MS (A): $t_R$=0.73 min; [M+H]+: 240.05

A.27. Synthesis of 4-chloro-7-hydroxy-1H-indole-5-carboxylic acid

This compound was prepared using a method analogous to that of 4,7-dimethyl-1H-indole-5-carboxylic acid, 4-chloro-7-hydroxy-1H-indole-5-carbonitrile replacing 4,7-dimethyl-1H-indole-5-carbonitrile.

LC-MS (A): $t_R$=0.60 min; [M+CH$_3$CN+H]+: 253.02

A.28. Synthesis of 4-chloro-7-propyl-1H-indole-5-carboxylic acid

A.28.a. Methyl 4-amino-2-chloro-5-propylbenzoate

This compound was prepared using a method analogous to that of methyl 4-amino-2-chloro-5-isobutylbenzoate, 1-propylboronic acid replacing (2-methylpropyl)boronic acid.

LC-MS (A): $t_R$=0.86 min; [M+H]+: 228.15

A.28.b. Methyl 4-amino-2-chloro-3-iodo-5-propylbenzoate

This compound was prepared using a method analogous to that of the mixture of methyl 4-amino-2-chloro-3-iodobenzoate and methyl 4-amino-2-chloro-5-iodobenzoate, methyl 4-amino-2-chloro-5-propylbenzoate replacing methyl 4-amino-2-chlorobenzoate.

LC-MS (A): $t_R$=0.94 min; [M+H]+: 353.66

A.28.c. Methyl 4-amino-2-chloro-5-propyl-3-(trimethylsilyl)ethynyl)benzoate This compound was prepared using a method analogous to that of methyl 4-amino-2-chloro-3-((trimethylsilyl)ethynyl)benzoate, methyl 4-amino-2-chloro-3-iodo-5-propylbenzoate replacing the mixture of methyl 4-amino-2-chloro-3-iodobenzoate and methyl 4-amino-2-chloro-5-iodobenzoate.

LC-MS (A): $t_R$=1.05 min; [M+H]+: 324.10

A.28.d. Methyl 4-amino-2-chloro-3-ethynyl-5-propylbenzoate

This compound was prepared using a method analogous to that of methyl 4-amino-2-chloro-3-ethynylbenzoate, methyl 4-amino-2-chloro-5-propyl-3-((trimethylsilyl)ethynyl) benzoate replacing methyl 4-amino-2-chloro-3-((trimethylsilyl)ethynyl)benzoate.

LC-MS (A): $t_R$=0.90 min; [M+H]+: 252.25

A.28.e. Methyl 4-chloro-7-propyl-1H-indole-5-carboxylate

This compound was prepared using a method analogous to that of methyl 4-chloro-1H-indole-5-carboxylate, methyl 4-amino-2-chloro-3-ethynyl-5-propylbenzoate replacing methyl 4-amino-2-chloro-3-ethynylbenzoate.

LC-MS (A): $t_R$=0.91 min; [M+H]+: 252.21

A.28.f. 4-Chloro-7-propyl-1H-indole-5-carboxylic acid

This compound was prepared using a method analogous to that of 4-chloro-7-methyl-1H-indole-5-carboxylic acid, methyl 4-chloro-7-propyl-1H-indole-5-carboxylate replacing methyl 4-chloro-7-methyl-1H-indole-5-carboxylate.

LC-MS (A): $t_R$=0.78 min, [M+H]+: 238.19

A.29. Synthesis of 7-(2-(tert-butoxy)ethoxy)-4-chloro-1H-indole-5-carboxylic acid

A.29.a. 7-(2-(tert-Butoxy)ethoxy)-4-chloro-1H-indole-5-carbonitrile

This compound was prepared using a method analogous to that of 4-chloro-7-ethoxy-1H-indole-5-carbonitrile, 2-(2-bromoethoxy)-2-methylpropane replacing ethyl bromide except that the reaction mixture was stirred for 8 h at 80° C.

LC-MS (A): $t_R$=0.94 min, [M+CH$_3$CN+H]+: 334.12

A.29.b. 7-(2-(tert-Butoxy)ethoxy)-4-chloro-1H-indole-5-carboxylic acid

This compound was prepared using a method analogous to that of 4,7-dimethyl-1H-indole-5-carboxylic acid, 7-(2-(tert-butoxy)ethoxy)-4-chloro-1H-indole-5-carbonitrile replacing 4,7-dimethyl-1H-indole-5-carbonitrile.

LC-MS (A): $t_R$=0.80 min; [M+CH$_3$CN+H]+: 353.16

$^1$H NMR ((CD$_3$)$_2$SO) δ: 12.86 (s very br, 1 H), 11.74 (s, 1 H), 7.43 (dd, J$_1$=J$_2$=2.7 Hz, 1 H), 7.17 (s, 1 H), 6.58 (m, 1 H), 4.26 (m, 2 H), 3.74 (m, 2 H), 1.18 (s, 9 H)

A.30. Synthesis of 4,7-difluoro-1H-indole-5-carboxylic acid

A.30.a. Methyl 2,5-difluoro-4-nitrobenzoate

This compound was prepared using a method analogous to that of methyl 4-amino-2-chlorobenzoate, 2,5-difluoro-4-nitrobenzoic acid replacing 4-amino-2-chlorobenzoic acid.

LC-MS (A): $t_R$=0.80 min $^1$H NMR ((CD$_3$)$_2$SO) δ: 8.31 (dd, J$_1$=6.0 Hz, J$_2$=9.7 Hz, 1 H), 8.07 (dd, J$_1$=5.8 Hz, J$_2$=10.9 Hz, 1 H), 3.92 (s, 3 H)

A.30.b. Methyl 4-amino-2,5-difluorobenzoate

This compound was prepared using a method analogous to that of methyl 4-amino-5-methoxy-2-methylbenzoate, methyl 2,5-difluoro-4-nitrobenzoate replacing methyl 5-methoxy-2-methyl-4-nitrobenzoate.

LC-MS (A): $t_R$=0.70 min, [M+H]+: 188.22

A.30.c. Methyl 4-amino-2,5-difluoro-3-iodobenzoate

This compound was prepared using a method analogous to that of the mixture of methyl 4-amino-2-chloro-3-iodobenzoate and methyl 4-amino-2-chloro-5-iodobenzoate, methyl 4-amino-2,5-difluorobenzoate replacing methyl 4-amino-2-chlorobenzoate except that the reaction mixture was stirred for 1 h at RT.

LC-MS (A): $t_R$=0.81 min $^1$H NMR ((CD$_3$)$_2$SO) δ: 7.52 (dd, J$_1$=6.7 Hz, J$_2$=11.7 Hz, 1 H), 6.43 (s, 2 H), 3.78 (s, 3 H)

A.30.d. Methyl 4-amino-2,5-difluoro-3-(trimethylsilyl)ethynyl)benzoate

This compound was prepared using a method analogous to that of methyl 4-amino-2-chloro-3-((trimethylsilyl)ethynyl)benzoate, methyl 4-amino-2,5-difluoro-3-iodobenzoate replacing the mixture of methyl 4-amino-2-chloro-3-iodobenzoate and methyl 4-amino-2-chloro-5-iodobenzoate.

LC-MS (A): $t_R$=0.98 min; [M+H]+: 284.22

A.30.e. Methyl 4-amino-3-ethynyl-2,5-difluorobenzoate

This compound was prepared using a method analogous to that of methyl 4-amino-2-chloro-3-ethynylbenzoate, methyl 4-amino-2,5-difluoro-3-((trimethylsilyl)ethynyl) benzoate replacing methyl 4-amino-2-chloro-3-((trimethylsilyl)ethynyl)benzoate.

LC-MS (A): $t_R$=0.78 min $^1$H NMR ((CD$_3$)$_2$SO) δ: 7.48 (dd, J$_1$=6.6 Hz, J$_2$=11.8 Hz, 1 H), 6.66 (s, 2 H), 4.80 (s, 1 H), 3.78 (s, 3 H)

A.30.f. Methyl 4,7-difluoro-1H-indole-5-carboxylate

This compound was prepared using a method analogous to that of methyl 4-chloro-1H-indole-5-carboxylate, methyl 4-amino-3-ethynyl-2,5-difluorobenzoate replacing methyl 4-amino-2-chloro-3-ethynylbenzoate.

LC-MS (A): $t_R$=0.79 min, [M+H]+: 212.21

A.30.g. 4,7-Difluoro-1H-indole-5-carboxylic acid

This compound was prepared using a method analogous to that of 4-chloro-7-methyl-1H-indole-5-carboxylic acid, methyl 4,7-difluoro-1H-indole-5-carboxylate replacing methyl 4-chloro-7-methyl-1H-indole-5-carboxylate.

LC-MS (A): $t_R$=0.64 min $^1$H NMR ((CD$_3$)$_2$SO) δ: 12.96 (s, 1 H), 12.29 (s, 1 H), 7.56 (dd, J$_1$=J$_2$=2.6 Hz, 1 H), 7.32 (dd, J$_1$=4.9 Hz, J$_2$=11.3 Hz, 1 H), 6.73 (m, 1 H)

A.31. Synthesis of 4-fluoro-7-methoxy-1H-indole-5-carboxylic acid

A.31.a. 2-Fluoro-5-methoxy-4-nitrobenzoic acid

To a suspension of 2,5-difluoro-4-nitrobenzoic acid (2.46 mmol) and $Cs_2CO_3$ (12.3 mmol) in DMF was added MeOH (16.5 mmol) and the mixture was stirred for 3 h 30 at RT. It was diluted with water, acidified with a 1M solution of HCl until pH=1-2 and extracted three times with EtOAc. The organic phases were washed with brine, dried over $MgSO_4$ and concentrated in vacuo to give the title compound as light yellow solid.

LC-MS (A): $t_R$=0.67 min
$^1$H NMR ((CD$_3$)$_2$SO) δ: 13.96 (s br, 1 H), 8.03 (d, J=9.6 Hz, 1 H), 7.68 (d, J=5.8 Hz, 1 H), 3.97 (s, 3 H)

A.31.b. Methyl 2-fluoro-5-methoxy-4-nitrobenzoate

This compound was prepared using a method analogous to that of methyl 4-amino-2-chlorobenzoate, 2-fluoro-5-methoxy-4-nitrobenzoic acid replacing 4-amino-2-chlorobenzoic acid.

LC-MS (A): $t_R$=0.81 min
$^1$H NMR ((CD$_3$)$_2$SO) δ: 8.09 (d, J=9.7 Hz, 1 H), 7.70 (d, J=5.7 Hz, 1 H), 3.98 (s, 3 H), 3.92 (s, 3 H)

A.31.c. Methyl 4-amino-2-fluoro-5-methoxybenzoate

This compound was prepared using a method analogous to that of methyl 4-amino-5-methoxy-2-methylbenzoate, methyl 2-fluoro-5-methoxy-4-nitrobenzoate replacing methyl 5-methoxy-2-methyl-4-nitrobenzoate.

LC-MS (A): $t_R$=0.70 min, [M+H]+: 200.19

A.31.d. Methyl 4-amino-2-fluoro-3-iodo-5-methoxybenzoate

This compound was prepared using a method analogous to that of the mixture of methyl 4-amino-2-chloro-3-iodobenzoate and methyl 4-amino-2-chloro-5-iodobenzoate, methyl 4-amino-2-fluoro-5-methoxybenzoate replacing methyl 4-amino-2-chlorobenzoate except that the reaction mixture was stirred for 2 h at RT.

LC-MS (A): $t_R$=0.83 min, [M+H]+: 325.97

A.31.e. Methyl 4-amino-2-fluoro-5-methoxy-3-((trimethylsilyl)ethynyl)benzoate This compound was prepared using a method analogous to that of methyl 4-amino-2-chloro-3-((trimethylsilyl)ethynyl)benzoate, methyl 4-amino-2-fluoro-3-iodo-5-methoxybenzoate replacing the mixture of methyl 4-amino-2-chloro-3-iodobenzoate and methyl 4-amino-2-chloro-5-iodobenzoate.

LC-MS (A): $t_R$=0.97 min; [M+H]+: 296.03

A.31.f. Methyl 4-amino-3-ethynyl-2-fluoro-5-methoxybenzoate

This compound was prepared using a method analogous to that of methyl 4-amino-2-chloro-3-ethynylbenzoate, methyl 4-amino-2-fluoro-5-methoxy-3-((trimethylsilyl) ethynyl) benzoate replacing methyl 4-amino-2-chloro-3-((trimethylsilyl)ethynyl)benzoate.

LC-MS (A): $t_R$=0.78 min; [M+H]+: 223.92

A.31.g. Methyl 4-fluoro-7-methoxy-1H-indole-5-carboxylate

This compound was prepared using a method analogous to that of methyl 4-chloro-1H-indole-5-carboxylate, methyl 4-amino-3-ethynyl-2-fluoro-5-methoxybenzoate replacing methyl 4-amino-2-chloro-3-ethynylbenzoate.

LC-MS (A): $t_R$=0.78 min, [M+H]+: 223.76
$^1$H NMR ((CD$_3$)$_2$SO) δ: 11.96 (s, 1 H), 7.41 (dd, $J_1$=$J_2$=2.6 Hz, 1 H), 6.99 (d, J=4.9 Hz, 1 H), 6.62 (m, 1 H), 3.95 (s, 3 H), 3.85 (s, 3 H)

A.31.h. 4-Fluoro-7-methoxy-1H-indole-5-carboxylic acid

This compound was prepared using a method analogous to that of 4-chloro-7-methyl-1H-indole-5-carboxylic acid, methyl 4-fluoro-7-methoxy-1H-indole-5-carboxylate replacing methyl 4-chloro-7-methyl-1H-indole-5-carboxylate.

LC-MS (A): $t_R$=0.64 min, [M+H]+: 210.15

A.32. Synthesis of 4-chloro-7-(2-ethoxyethyl)-1H-indole-5-carboxylic acid

A.32.a. Methyl 4-amino-2-chloro-5-(2-ethoxyvinyl)benzoate

To a mixture of methyl 4-amino-2-chloro-5-iodobenzoate (1.05 mmol), KOH (2.1 mmol) Pd(OAc)$_2$ (0.03 mmol) and 2-dicyclohexylphosphino-2',6'-dimethoxybiphenyl (0.08 mmol) was added under argon $CH_3CN$ (10 mL) and trans-2-ethoxyvinylboronic acid pinacol ester (2.1 mmol). The mixture was stirred for 1 h at 70° C. in a sealed vial, quenched with a 10% solution of $NH_4Cl$ and extracted three times with DCM. The organic phases were dried over $MgSO_4$ and concentrated in vacuo. The crude was purified by CC (SNAP KP-Sil™ from Biotage) using Hept/EtOAc from 100/0 to 27/63 to give the title compound as brown oil.

LC-MS (A): $t_R$=0.85 min; [M+CH$_3$CN+H]+: 297.04

A.32.b. Methyl 4-amino-2-chloro-5-(2-ethoxyethyl)benzoate

To a solution of methyl 4-amino-2-chloro-5-(2-ethoxyvinyl)benzoate (0.63 mmol) in EtOH (4.2 mL) was added platinum (IV) oxide (0.13 mmol). The mixture was stirred under a hydrogen atmosphere for 3 h, filtered over Celite and concentrated in vacuo. The crude was purified by CC (SNAP KP-Sil™ from Biotage) using Hept/EtOAc from 100/0 to 63/37 to give the title compound as brownish oil.

LC-MS (A): $t_R$=0.81 min, [M+H]+: 257.95

A.32.c. Methyl 4-amino-2-chloro-5-(2-ethoxyethyl)-3-iodobenzoate

This compound was prepared using a method analogous to that of the mixture of methyl 4-amino-2-chloro-3-iodobenzoate and methyl 4-amino-2-chloro-5-iodobenzoate, methyl 4-amino-2-chloro-5-(2-ethoxyethyl)benzoate replacing methyl 4-amino-2-chlorobenzoate except that the reaction mixture was stirred for 1 h at RT.

LC-MS (A): $t_R$=0.91 min, [M+H]+: 384.10

A.32.d. Methyl 4-amino-2-chloro-5-(2-ethoxyethyl)-3-(trimethylsilyl)ethynyl)benzoate This compound was prepared using a method analogous to that of methyl 4-amino-2-chloro-3-((trimethylsilyl)ethynyl)benzoate, methyl 4-amino-2-chloro-5-(2-ethoxyethyl)-3-iodobenzoate replacing the mixture of methyl 4-amino-2-chloro-3-iodobenzoate and methyl 4-amino-2-chloro-5-iodobenzoate.

LC-MS (A): $t_R$=1.05 min; [M+H]+: 353.87

A.32.e. Methyl 4-amino-2-chloro-5-(2-ethoxyethyl)-3-ethynylbenzoate

This compound was prepared using a method analogous to that of methyl 4-amino-2-chloro-3-ethynylbenzoate, methyl 4-amino-2-chloro-5-(2-ethoxyethyl)-3-((trimethylsilyl)ethynyl)benzoate replacing methyl 4-amino-2-chloro-3-((trimethylsilyl)ethynyl)benzoate.

LC-MS (A): $t_R$=0.87 min; [M+H]+: 282.15

A.32.f. Methyl 4-chloro-7-(2-ethoxyethyl)-1H-indole-5-carboxylate

This compound was prepared using a method analogous to that of methyl 4-chloro-1H-indole-5-carboxylate, methyl 4-amino-2-chloro-5-(2-ethoxyethyl)-3-ethynylbenzoate replacing methyl 4-amino-2-chloro-3-ethynylbenzoate.

LC-MS (A): $t_R$=0.87 min, [M+H]+: 282.14

$^1$H NMR ((CD$_3$)$_2$SO) δ: 11.77 (s, 1 H), 7.55 (dd, $J_1$=$J_2$=2.8 Hz, 1 H), 7.49 (s, 1 H), 6.63 (dd, =2.0 Hz, $J_2$=3.1 Hz, 1 H), 3.85 (s, 3 H), 3.66 (t, J=7.0 Hz, 2 H), 3.45 (q, J=7.0 Hz, 2 H), 3.12 (t, J=6.9 Hz, 2 H), 1.09 (t, J=7.0 Hz, 3 H)

A.32.g. 4-Chloro-7-(2-ethoxyethyl)-1H-indole-5-carboxylic acid

This compound was prepared using a method analogous to that of 4-chloro-7-methyl-1H-indole-5-carboxylic acid, methyl 4-chloro-7-(2-ethoxyethyl)-1H-indole-5-carboxylate replacing methyl 4-chloro-7-methyl-1H-indole-5-carboxylate.

LC-MS (A): $t_R$=0.74 min, [M+H]+: 268.03

A.33. Synthesis of 4-chloro-7-(2-methoxypropan-2-yl)-1H-indole-5-carboxylic acid

A.33.a. Methyl 4-chloro-7-(2-hydroxypropan-2-yl)-1H-indole-5-carboxylate

To a solution of methyl 7-acetyl-4-chloro-1H-indole-5-carboxylate (0.56 mmol) in THF (11 mL) was added dropwise at −10° C. a 3M solution of methylmagnesium bromide in diethyl ether (1.12 mmol). The mixture was stirred for 1 h at RT and an additional amount of a 3M solution of methylmagnesium bromide in diethyl ether (1.12 mmol) was added at −10° C. The mixture was further stirred for 1 h at RT and cooled to 0° C. It was quenched with a sat. solution of NH$_4$Cl and extracted three times with EtOAc. The organic phases were washed with brine, dried over MgSO$_4$ and concentrated in vacuo. The crude was purified by CC (Isolute™ Silica II from Biotage) using DCM/MeOH from 100/0 to 99/1 to give the title compound as grey solid.

LC-MS (A): $t_R$=0.79 min; [M+H]+: 268.15

A.33.b. Methyl 4-chloro-7-(2-methoxypropan-2-yl)-1H-indole-5-carboxylate

To a solution of methyl 4-chloro-7-(2-hydroxypropan-2-yl)-1H-indole-5-carboxylate (0.39 mmol) in THF (1 mL) was added at 0° C. a 60% suspension of NaH in mineral oil (1.18 mmol) followed by methyl iodide (0.39 mmol). The mixture was stirred for 10 min at 0° C., ON at RT and cooled to 0° C. It was quenched with a sat. solution of NaHCO$_3$ and extracted three times with EtOAc. The organic phases were washed with brine, dried over MgSO$_4$ and concentrated in vacuo. The crude was purified by preparative LC-MS using method II to give the title compound as white solid.

LC-MS (A): $t_R$=0.88 min $^1$H NMR ((CD$_3$)$_2$SO) δ: 11.25 (s br, 1 H), 7.47 (s, 1 H), 7.45 (dd, $J_1$=$J_2$=2.9 Hz, 1 H), 6.64 (m, 1 H), 3.86 (s, 3 H), 2.97 (s, 3 H), 1.61 (s, 6 H)

A.33.c. 4-Chloro-7-(2-methoxypropan-2-yl)-1H-indole-5-carboxylic acid

This compound was prepared using a method analogous to that of 4-chloro-7-methyl-1H-indole-5-carboxylic acid, methyl 4-chloro-7-(2-methoxypropan-2-yl)-1H-indole-5-carboxylate replacing methyl 4-chloro-7-methyl-1H-indole-5-carboxylate.

LC-MS (A): $t_R$=0.75 min

B. Synthesis of Amines

B.1. Synthesis of (1-aminomethyl)cycloheptanol

This compound was synthesized according to WO2012/114268.

B.2. Synthesis of 1-(aminomethyl)-4,4-difluorocyclohexanol

This compound was synthesized according to WO2012/114268.

B.3. Synthesis of (S)-2-amino-2-(4,4-difluorocyclohexyl)ethanol hydrochloride

B.3.a. (S)-methyl 2-((tert-butoxycarbonynamino)-2-(4-hydroxycyclohexyl)acetate This compound was synthesized according to Bioorg. Med. Chem. Lett., 2004, 14(1), 43-46.

B.3.b. (S)-methyl 2-((tert-butoxycarbonynamino)-2-(4-oxocyclohexyl)acetate

To a solution of (S)-methyl 2-((tert-butoxycarbonyl)amino)-2-(4-hydroxycyclohexyl)acetate (4.7 g) in DCM (45 mL) was added dropwise a 15% solution of DMP in DCM (51 mL, 1.5 eq). The mixture was stirred ON at RT, diluted with DCM and washed with a sat. solution of NaHCO$_3$ and water. The organic phase was dried over MgSO₄ and concentrated in vacuo. The crude was purified by CC (Hept/EtOAc 1/1) to give 4.6 g of the title compound as colorless oil.

LC-MS (B): $t_R$=0.64 min; [M+H]+: 286.03

B.3.c. (S)-methyl 2-((tert-butoxycarbonyl)amino)-2-(4,4-difluorocyclohexyl)acetate To a solution of (S)-methyl 2-((tert-butoxycarbonyl)amino)-2-(4-oxocyclohexyl)acetate (4.6 g) in DCM (45 mL) was slowly added at 0° C. a 50% solution of bis(2-methoxyethyl)aminosulfur trifluoride in THF (26 mL). The mixture was stirred for 30 min at 0° C. and ON at RT and quenched at 0° C. with a sat. solution of NaHCO₃. It was extracted with DCM and washed with water. The organic phase was dried over MgSO₄ and concentrated in vacuo. The crude was purified by CC (Hept/EtOAc 2/1) to give 4.0 g of the title compound as light yellow oil.

LC-MS (B): $t_R$=0.81 min; [M+H]+: 308.08

B.3.d. (S)-tert-butyl (1-(4,4-difluorocyclohexyl)-2-hydroxyethyl)carbamate

To a solution of (S)-methyl 2-((tert-butoxycarbonyl)amino)-2-(4,4-difluorocyclohexyl) acetate (4.1 g) in EtOH (54 mL) was slowly added at 0° C. CaCl₂ (27 mg), THF (18 mL) and NaBH₄ (2 g). The mixture was stirred for 3 h at 0° C. and quenched with a citric acid solution. It was extracted with DCM and washed with water. The organic phase was dried over MgSO₄ and concentrated in vacuo. The crude was purified by CC (Hept/EtOAc 1/1) to give 1.8 g of the title compound as white solid.

LC-MS (B): $t_R$=0.69 min; [M+H]+: 280.01

B.3.e. (S)-2-amino-2-(4,4-difluorocyclohexyl)ethanol hydrochloride

To a solution of (S)-tert-butyl (1-(4,4-difluorocyclohexyl)-2-hydroxyethyl)carbamate (1.8 g) in EtOAc (25 mL) was added a 4M solution of HCl in dioxane (6.5 mL). The mixture was stirred for 24 h at RT, concentrated in vacuo and dried at HV to give the title compound as white solid.

LC-MS (B): $t_R$=0.31 min; [M+H]+: 180.18

B.4. Synthesis of 2-amino-2-cycloheptylethanol

B.4.a. 2-Amino-2-cycloheptylacetic acid tert-butyl ester

To a solution of N-(diphenylmethylene)glycerine tert-butyl ester (6.83 mmol) and (R)-4,4-dibutyl-2,6-bis(3,4,5-trifluorophenyl)-4,5-dihydro-3H-dinaphthol[7,6,1,2-cde]azepinium bromide (6.84 µmol) in 45 mL toluene were sequentially added cycloheptyl bromide (8.2 mmol) and CsOH H₂O (34.2 mmol) at −10° C. The reaction mixture was stirred at −10° C. for 10 min and then at RT for 4 days. Another portion of (R)-4,4-dibutyl-2,6-bis(3,4,5-trifluorophenyl)-4,5-dihydro-3H-dinaphthol[7,6,1,2-cde]azepinium bromide (6.84 µmol) was added and stirring was continued at RT for another 24 h. The reaction was quenched with water and extracted 3 times with DCM. The combined organic layers were combined, concentrated and the residue was redissolved in 100 mL THF. A solution of 100 mL aq. 0.5M citric acid solution was added and the mixture was stirred at RT for 4 h. The mixture was concentrated to half of its volume and extracted twice with Et₂O. The aqueous layer was basified with solid NaHCO₃ and extracted 3 times with DCM. The combined organic layers were dried over MgSO₄ and concentrated in vacuo to obtain the desired product as yellow oil.

LC-MS (B): $t_R$=0.61 min; [M+H]+: 228.29

B.4.b. 2-Amino-2-cycloheptylethanol

To a solution of 3.43 mL LiAlH₄ (1M in THF) in 8 mL THF was added a solution of 2-amino-2-cycloheptylacetic acid tert-butyl ester (1.72 mmol) in 3 mL THF at 0° C. The ice bath was removed and stirring was continued at RT for 1 h. The reaction mixture was cooled to 0° C., quenched with water and a 1M NaOH solution, filtered over a pad of celite and washed with EtOAc. The filtrate was basified with a 1M NaOH solution to pH 8-9 and extracted 3 times with EtOAc. The combined organic layers were dried over MgSO4 and concentrated in vacuo to obtain the crude product as yellow oil. The crude was dissolved in 3 mL Et₂O and a solution of 4M HCl in dioxane was dropwise added at 0° C. The resulting precipitate was separated by filtration and dried in vacuo to give the corresponding HCl salt as yellow solid.

LC-MS (B): $t_R$=0.39 min; [M+H]+: 158.14

B.5. Synthesis of (1-(hetero)aryl)cycloalkyl)methanamine

B.5.a. Synthesis of 2-(hetero)arylcyanoacetate

These compounds were synthesized according to *J. Org. Chem.*, 2008, 73 (4), 1643-1645.

B.5.a.1. Methyl 2-cyano-2-(2-(trifluoromethyl)pyrimidin-5-yl)acetate

To a suspension of KOᵗBu (618 mg) in dioxane (10 mL) were added methylcyanoacetate (0.194 mL), 5-bromo-2-(trifluoromethyl)pyrimidine (500 mg) followed by a solution of Pd(OAc)₂ (30 mg) and dppf (98 mg) in dioxane (2 mL). The mixture was flushed with argon and the vial sealed and heated ON at 90° C. It was quenched with a 2M aq. solution of AcOH and extracted with EtOAc. The organic phase was washed with brine, dried over MgSO₄ and concentrated in vacuo. The crude was purified by CC (KP-Sil™ from Biotage) using EtOAc/MeOH from 1/0 to 8/2 to give the title compound as brown oil (303 mg).

¹H NMR (CDCl₃) δ: 9.04 (s, 2 H), 4.90 (s, 1 H), 3.92 (s, 3 H)

B.5.a.2. Methyl 2-cyano-2-(6-(trifluoromethyl)pyridin-3-yl)acetate

This compound was prepared using a method analogous to that of methyl 2-cyano-2-(2-(trifluoromethyl)pyrimidin-5-yl)acetate, 5-bromo-2(trifluoromethyl)pyridine replacing 5-bromo-2-(trifluoromethyl)pyrimidine except that the mixture was heated for 1 h at 70° C.

LC-MS (B): $t_R$=0.66 min; [M+H]+: 245.13

¹H NMR (CDCl₃) δ: 8.81 (d, J=2.1 Hz, 1 H), 8.05 (m, 1 H), 7.79 (dd, J₁=8.2 Hz, J₂=0.6 Hz, 1 H), 4.88 (s, 1 H), 3.87 (s, 3 H)

B.5.b. Synthesis of 2-(hetero)arylacetonitrile

B.5.b.1. 2-(2-(Trifluoromethyl)pyrimidin-5-yl)acetonitrile

To a solution of methyl 2-cyano-2-(2-(trifluoromethyl)pyrimidin-5-yl)acetate (330 mg) in DMSO/water 9/1 (1.5 mL) was added LiCl (231 mg). The mixture was heated to 140° C. for 30 min under microwave conditions, poured onto water and extracted 2 times with EtOAc. The combined organic phases were dried over $MgSO_4$ and concentrated in vacuo. The crude was purified by CC (KP-NH™ from Biotage) using DCM/MeOH from 99/1 to 95/5 to give the title compound as yellow solid (96 mg).

LC-MS (B): $t_R$=0.51 min $^1$H NMR (CDCl$_3$) δ: 8.94 (s, 2 H), 3.89 (s, 2 H)

B.5.b.2. 2-(6-(Trifluoromethyl)pyridin-3-yl)acetonitrile

This compound was prepared using a method analogous to that of 2-(2-(trifluoromethyl)pyrimidin-5-yl)acetonitrile, methyl 2-cyano-2-(6-(trifluoromethyl)pyridin-3-yl)acetate replacing methyl 2-cyano-2-(2-(trifluoromethyl)pyrimidin-5-yl)acetate except that the mixture was heated for 1 h at 70° C.

LC-MS (B): $t_R$=0.57 min; [M+CH$_3$CN+H]+: 228.17 flushed with argon, Pd(dppf)Cl$_2$.DCM (0.58 mmol) was added and the mixture was heated for 48 h at 130° C. It was filtered over a pad of Celite and washed with EtOAc. The filtrate was partitioned between water and EtOAc and the aqueous phase was extracted twice with EtOAc. The combined organic phases were dried over $MgSO_4$ and concentrated in vacuo. The crude was purified by CC using DCM/MeOH from 1/0 to 95/5 to give the title compound as brown oil.

LC-MS (A): $t_R$=0.43 min; [M+H]+: 134.10

B.5.c. Alkylation (general procedure III)

To a solution of 2-(hetero)arylacetonitrile (0.51 mmol) and α,ω-dibromoalkane (0.51 mmol) in THF/DMSO 1/1 (6 mL) was added portionwise at 0° C. a 60% suspension of NaH in mineral oil (1.07 mmol). The mixture was allowed to warm to RT and stirred for 2 h. It was poured onto water and extracted with EtOAc. The combined organic phases were washed with brine, dried over $MgSO_4$ and concentrated in vacuo. The crude was purified by CC (KP-NH™ from Biotage) using DCM/MeOH from 99/1 to 90/10 to give the desired 1-(hetero)arylcycloalkylcarbonitriles which are listed in the table below.

| Name | LC-MS type | tR (min) | [M + H]+ |
|---|---|---|---|
| 1-(2-(trifluoromethyl)pyrimidin-5-yl)cyclohexanecarbonitrile | B | 0.80 | no ionisation |
| 1-(6-chloropyridin-3-yl)cyclohexanecarbonitrile | B | 0.78 | 221.20 |
| 1-(6-(trifluoromethyl)pyridin-3-yl)cyclohexanecarbonitrile | B | 0.83 | 255.20 |
| 1-(4-(trifluoromethyl)phenyl)cyclohexanecarbonitrile | B | 0.95 | no ionisation |
| 1-(pyridin-3-yl)cyclohexanecarbonitrile | B | 0.44 | 187.29 |
| 1-(pyridin-3-yl)cyclopentanecarbonitrile | B | 0.35 | 173.07 |
| 1-(pyridin-3-yl)cycloheptanecarbonitrile | B | 0.50 | 201.20 |
| 1-(2-methylpyrimidin-5-yl)cyclohexanecarbonitrile | A | 0.73 | 202.08 |

A.1.a.1 2-(2-Methypyrimidin-5-yl)acetonitrile

This compound was synthesized according to *J. Am. Chem. Soc.*, 2011, 133, 6948-6951.

To a solution of 5-bromo-2-methylpyrimidine (5.78 mmol) and 4-isoxazoleboronic acid pinacol ester (6.07 mmol) in DMSO (40 mL) was added a solution of potassium fluoride (17.30 mmol) in water (17 mL). The mixture was

B.5.d. Hydrogenation of nitrile (general procedure IV)

To a solution of the 1-(hetero)arylcycloalkylcarbonitrile (0.47 mmol) from the previous step in a 7M solution of NH$_3$ in MeOH (0.57 mL) was added Actimet M Raney nickel. The mixture was stirred under a hydrogen atmosphere for 2 h. It was filtered over Celite, washed with MeOH and concentrated in vacuo to give the desired (1-(hetero)arylcycloalkyl)methanamines which are listed in the table below

| Name | LC-MS type | tR (min) | [M + H]+ |
|---|---|---|---|
| (1-(2-(trifluoromethyl)pyrimidin-5-yl)cyclohexyl)methanamine | B | 0.51 | [M + CH$_3$CN + H]+: 301.09 |
| (1-(6-chloropyridin-3-yl)cyclohexyl)methanamine | B | 0.47 | 225.27 |
| (1-(6-(trifluoromethyl)pyridin-3-yl)cyclohexyl)methanamine | B | 0.53 | 259.22 |
| (1-(4-(trifluoromethyl)phenyl)cyclohexyl)methanamine | B | 0.65 | 257.96 |
| (1-(pyridin-3-yl)cyclohexyl)methanamine | B | 0.26 | 191.31 |
| (1-(pyridin-3-yl)cyclopentyl)methanamine | B | 0.20 | 177.32 |
| (1-(pyridin-3-yl)cycloheptyl)methanamine | B | 0.32 | 205.28 |
| (1-(2-methylpyrimidin-5-yl)cyclohexyl)methanamine | A | 0.45 | 206.13 |

B.5.e. Synthesis of (4,4-difluoro-1-(6-chloropyridin-3-yl)cyclohexyl)methanamine

B.5.e.1. Methyl 5-(6-chloropyridin-3-yl)-5-cyano-2-hydroxycyclohex-1-enecarboxylate To a solution of 2-(6-chloro-3-pyridinyl)acetonitrile (13.1 mmol) in 35 mL THF were added methylacrylate (26.2 mmol) and KOtBu (15.7 mmol). The reaction mixture was stirred at RT for 1 h. The mixture was acidifed with 1N HCl solution and then extracted with DCM. The combined organic layers were washed with brine, dried over MgSO4 and concentrated in vacuo. Purification with CC (KP-SIL™ from Biotage) using Hept/EtOAc (90/10 to 50/50) gives the desired compound as white solid.

LC-MS (B): $t_R$=0.74 min; [M+CH$_3$CN+H]+: 334.03

B.5.e.2. 1-(6-Chloropyridin-3-yl)-4-oxocyclohexanecarbonitrile

A mixture of methyl 5-(6-chloropyridin-3-yl)-5-cyano-2-hydroxycyclohex-1-enecarboxylate (10.6 mmol) and LiCl (21.1 mmol) in 15 mL wet DMSO was heated to 120° C. under microwave conditions for 2 h. The reaction mixture was diluted with water and extracted with EtOAc. The combined organic layers were washed with brine, dried over MgSO4 and concentrated in vacuo. Purification with CC (KP-SIL™ from Biotage) using Hept/EtOAc (95/5 to 20/80) gives the desired compound as yellow solid.

LC-MS (B): $t_R$=0.56 min; [M+CH$_3$CN+H]+: 276.12

B.5.e.3. 1-(6-Chloropyridin-3-yl)-4,4-difluorocyclohexanecarbonitrile

A solution of 1-(6-chloropyridin-3-yl)-4-oxocyclohexanecarbonitrile (3.89 mmol) in 4 mL DCM was cooled to −78° C., (diethylamino)sulfur trifluoride (7.78 mmol) was dropwise added and the mixture was stirred for 24 h allowing to reach slowly RT. The reaction mixture was quenched with sat. aq. NaHCO$_3$ solution under ice cooling and diluted with DCM. The organic phase was washed with brine, dried over MgSO4 and concentrated in vacuo. Purification with CC (KP-SIL™ from Biotage) using Hept/EtOAc (90/10 to 50/50) gives the desired compound as beige solid.

LC-MS (B): $t_R$=0.74 min; [M+CH$_3$CN+H]+: 298.00

B.5.e.4. (4,4-Difluoro-1-(6-chloropyridin-3-yl)cyclohexyl)methanamine

A solution of 1-(6-chloropyridin-3-yl)-4,4-difluorocyclohexanecarbonitrile (2.02 mmol) in 20 mL THF was added to a solution of BH$_3$ in THF (6.07 mmol, 1M). After heating to reflux for 1 h, the reaction mixture was cooled in an ice bath before a 2N HCl solution was slowly added. The mixture was then heated to reflux for another 20 min. The reaction mixture was washed with DCM, basified with 1N NaOH solution and extracted 3 times with DCM. The combined organic layers were washed with brine, dried over MgSO4 and concentrated in vacuo to give the desired product as yellow oil.

LC-MS (B): $t_R$=0.46 min; [M+CH$_3$CN+H]+: 302.03

B.5.f Synthesis of (1-(4-chlorophenyl)cyclohexyl)methanamine

To a 1M solution of BH$_3$.THF complex (6.8 mL) was added a solution of 1-(4-chlorophenyl)-1-cyclohexanecarbonitrile (500 mg) in anh. THF (23 mL). The mixture was refluxed for 1 h, acidified at RT with a 2M solution of HCl (14 mL) and refluxed for 20 min. It was washed with DCM, basified with 1M NaOH and extracted 3 times with DCM. The combined organic phases were dried and concentrated in vacuo to give the title compound as yellow oil (275 mg).

LC-MS (B): $t_R$=0.61 min; [M+H]+: 224.24

B.5.g. Synthesis of (4,4-difluoro-1-(2-methylpyrimidin-5-yl)cyclohexyl)methanamine

B.5.g.1. Methyl 5-cyano-2-hydroxy-5-(2-methylpyrimidin-5-yl)cyclohex-1-enecarboxylate This compound was prepared using a method analogous to that of methyl 5-(6-chloropyridin-3-yl)-5-cyano-2-hydroxycyclohex-1-enecarboxylate, 2-(2-methylpyrimidin-5-yl)acetonitrile replacing 2-(6-chloro-3-pyridinyl)acetonitrile.

LC-MS (A): $t_R$=0.73 min; [M+H]+: 273.93

B.5.g.2. 1-(2-Methylpyrimidin-5-yl)-4-oxocyclohexanecarbonitrile

This compound was prepared using a method analogous to that of 1-(6-chloropyridin-3-yl)-4-oxocyclohexanecarbonitrile, methyl 5-cyano-2-hydroxy-5-(2-methylpyrimidin-5-yl)cyclohex-1-enecarboxylate replacing methyl 5-(6-chloropyridin-3-yl)-5-cyano-2-hydroxycyclohex-1-enecarboxylate.

LC-MS (A): $t_R$=0.53 min; [M+H]+: 216.16

B.5.g.3. 4,4-Difluoro-1-(2-methylpyrimidin-5-yl)cyclohexanecarbonitrile

This compound was prepared using a method analogous to that of 1-(6-chloropyridin-3-yl)-4,4-difluorocyclohexanecarbonitrile, 1-(2-methylpyrimidin-5-yl)-4-oxocyclohexane-carbonitrile replacing 1-(6-chloropyridin-3-yl)-4-oxocyclohexanecarbonitrile.

LC-MS (A): $t_R$=0.71 min; [M+H]+: 238.11

B.5.g.4. (4,4-Difluoro-1-(2-methylpyrimidin-5-yl)cyclohexyl)methanamine

This compound was prepared according the general procedure IV (hydrogenation of nitriles) engaging 4,4-difluoro-1-(2-methylpyrimidin-5-yl)cyclohexanecarbonitrile.

LC-MS (A): $t_R$=0.45 min; [M+CH$_3$CN+H]+: 283.14

B.6. Synthesis of (1-aminomethyl)cyclopentanol

This compound was synthesized according to WO2012/114268.

B.7. Synthesis of (1-aminomethyl)cyclooctanol

This compound was synthesized according to WO2012/114268.

B.8. Synthesis of (1-methoxycyclohexyl)methanamine

This compound was synthesized according to WO2012/114268.

PREPARATION OF EXAMPLES

A. Synthesis of compounds of formula I (general procedure V)

To a solution of the respective carboxylic acid precursor (II) (0.23 mmol) in a mixture of DCM/DMF (0.4 mL) were consecutively added DIPEA (0.69 mmol), HOBt (0.28 mmol) and EDC.HCl (0.28 mmol) followed by a solution of the respective amine precursor (III) (0.25 mmol) in DCM (0.1 mL). The mixture was stirred ON at RT, diluted with DCM and washed twice with a 5% solution of KHSO$_4$ (for non basic product), with a sat. solution of NaHCO$_3$ and with brine. The organic phase was dried over MgSO$_4$ and concentrated in vacuo. The crude was purified using conditions which are detailed in the table below. All compounds in the following table were synthesized according to the aforementioned general procedure except compounds which are marked with "see below under section B"; such compounds were synthesized according to the specific procedures given in section "B. Post amide coupling steps" below.

| Compound | Name | Purification method | LC-MS type | tR (min) | [M + H]+ |
|---|---|---|---|---|---|
| Example 1 | 4-Chloro-1H-indole-5-carboxylic acid ((S)-1-cyclohexyl-2-hydroxy-ethyl)-amide | a | B | 0.69 | 321.11 |
| Example 2 | 4-Chloro-1H-indole-5-carboxylic acid (1-hydroxy-cyclohexylmethyl)-amide | precipitate from DCM | B | 0.62 | 307.14 |
| Example 3 | 4-Chloro-1H-indole-5-carboxylic acid (1-hydroxy-cycloheptylmethyl)-amide | a | B | 0.68 | 321.00 |
| Example 4 | 4-Chloro-1H-indole-5-carboxylic acid (4,4-difluoro-1-hydroxy-cyclohexylmethyl)-amide | b | B | 0.62 | 343.11 |
| Example 5 | 4-Chloro-1H-indole-5-carboxylic acid [(S)-1-(4,4-difluoro-cyclohexyl)-2-hydroxy-ethyl]-amide | a | B | 0.63 | 357.11 |
| Example 6 | 4-Chloro-1-methyl-1H-indole-5-carboxylic acid (1-hydroxy-cyclohexylmethyl)-amide | a | B | 0.68 | 321.10 |
| Example 7 | 4-Chloro-1-methyl-1H-indole-5-carboxylic acid ((S)-1-cyclohexyl-2-hydroxy-ethyl)-amide | a | B | 0.74 | 335.04 |
| Example 8 | 4-Chloro-3-formyl-1H-indole-5-carboxylic acid ((S)-1-cyclohexyl-2-hydroxy-ethyl)-amide | I | B | 0.59 | 349.19 |
| Example 9 | 4-Chloro-3-formyl-1H-indole-5-carboxylic acid (1-hydroxy-cyclohexylmethyl)-amide | I | B | 0.53 | 335.12 |
| Example 10 | rac-4-Chloro-1H-indole-5-carboxylic acid (1-cycloheptyl-2-hydroxy-ethyl)-amide | c | B | 0.74 | 335.19 |
| Example 11 | 4-Chloro-1H-indole-5-carboxylic acid [1-(2-trifluoromethyl-pyrimidin-5-yl)-cyclohexylmethyl]-amide | d + II | C | 0.90 | 436.90 |
| Example 12 | 4-Chloro-1H-indole-5-carboxylic acid [1-(6-chloro-pyridin-3-yl)-cyclohexylmethyl]-amide | d + precipitate from MeCN | C | 0.89 | 401.65 |
| Example 13 | 4-Chloro-1H-indole-5-carboxylic acid [1-(6-trifluoromethyl-pyridin-3-yl)-cyclohexylmethyl]-amide | d + II | B | 0.87 | 436.29 |
| Example 14 | 4-Chloro-1H-indole-5-carboxylic acid [1-(6-chloro-pyridin-3-yl)-4,4-difluoro-cyclohexylmethyl]-amide | II | B | 0.78 | 437.86 |
| Example 15 | 4-Chloro-1H-indole-5-carboxylic acid [1-(4-chloro-phenyl)-cyclohexylmethyl]-amide | III | B | 0.97 | 400.91 |
| Example 16 | 4-Chloro-1H-indole-5-carboxylic acid [1-(4-trifluoromethyl-phenyl)-cyclohexylmethyl]-amide | III | B | 0.97 | 434.86 |
| Example 17 | 4-Chloro-1H-indole-5-carboxylic acid (1-pyridin-3-yl-cyclohexylmethyl)-amide | IV | B | 0.54 | 367.99 |
| Example 18 | 4-Chloro-1H-indole-5-carboxylic acid (1-pyridin-3-yl-cyclopentylmethyl)-amide | VI | B | 0.51 | 353.77 |
| Example 19 | 4-Chloro-1H-indole-5-carboxylic acid (1-pyridin-3-yl-cycloheptylmethyl)-amide | e | B | 0.58 | 381.98 |

-continued

| Compound | Name | Purification method | LC-MS type | tR (min) | [M + H]+ |
|---|---|---|---|---|---|
| Example 20 | 4-Chloro-7-methyl-1H-indole-5-carboxylic acid (1-hydroxy-cyclohexylmethyl)-amide | a + VII | A | 0.76 | 321.18 |
| Example 21 | 4-Chloro-2-oxo-2,3-dihydro-1H-indole-5-carboxylic acid (1-hydroxy-cycloheptylmethyl)-amide | see below under section B | | | |
| Example 22 | 4-Chloro-2-methyl-1H-indole-5-carboxylic acid (1-hydroxy-cyclohexylmethyl)-amide | a | A | 0.76 | 321.25 |
| Example 23 | 4-Chloro-7-iodo-3-methylsulfanyl-1H-indole-5-carboxylic acid (1-hydroxy-cyclohexylmethyl)-amide | VII | A | 0.84 | 478.78 |
| Example 24 | 4-Chloro-7-methyl-1H-indole-5-carboxylic acid (4,4-difluoro-1-hydroxy-cyclohexylmethyl)-amide | a + VII | A | 0.76 | 357.10 |
| Example 25 | 4-Chloro-7-methyl-1H-indole-5-carboxylic acid (1-hydroxy-cycloheptylmethyl)-amide | precipitate from MeCN | A | 0.80 | 335.04 |
| Example 26 | 4-Chloro-3-fluoro-1H-indole-5-carboxylic acid (1-hydroxy-cycloheptylmethyl)-amide | VII + c | A | 0.78 | 338.99 |
| Example 27 | 4-Methoxy-1H-indole-5-carboxylic acid (1-hydroxy-cycloheptylmethyl)-amide | a | A | 0.76 | 317.29 |
| Example 28 | 3,4-Dichloro-1H-indole-5-carboxylic acid (1-hydroxy-cyclohexylmethyl)-amide | e | A | 0.77 | 340.90 |
| Example 29 | 4-Chloro-7-nitro-1H-indole-5-carboxylic acid (1-hydroxy-cyclohexylmethyl)-amide | VI | A | 0.77 | 351.91 |
| Example 30 | 1-{[(4-Chloro-1H-indole-5-carbonyl)-amino]-methyl}-cyclohexanecarboxylic acid methyl ester | a | A | 0.85 | 348.94 |
| Example 31 | 4-Chloro-1H-indole-5-carboxylic acid (1-hydroxymethyl-cyclohexylmethyl)-amide | see below under section B | | | |
| Example 32 | 7-Amino-4-chloro-1H-indole-5-carboxylic acid (1-hydroxy-cyclohexylmethyl)-amide | see below under section B | | | |
| Example 33 | 4-Chloro-3-methyl-1H-indole-5-carboxylic acid (1-hydroxy-cycloheptylmethyl)-amide | c | A | 0.80 | 335.15 |
| Example 34 | 4-Chloro-1H-indole-5-carboxylic acid (1-carbamoyl-cyclohexylmethyl)-amide | see below under section B | | | |
| Example 35 | 4-Chloro-1H-indole-5-carboxylic acid (1-methylcarbamoyl-cyclohexylmethyl)-amide | see below under section B | | | |
| Example 36 | 4-Chloro-1H-indole-5-carboxylic acid (1-cyano-cyclohexylmethyl)-amide | see below under section B | | | |
| Example 37 | (1-{[(4-Chloro-1H-indole-5-carbonyl)-amino]-methyl}-cyclohexyl)-carbamic acid tert-butyl ester | precipitate from MeCN | A | 0.90 | 406.08 |
| Example 38 | 4,6-Dichloro-1H-indole-5-carboxylic acid (4,4-difluoro-1-hydroxy-cyclohexylmethyl)-amide | VI + c | A | 0.76 | 376.92 |
| Example 39 | 4-Chloro-1H-indole-5-carboxylic acid (1-amino-cyclohexylmethyl)-amide hydrochloride | see below under section B | | | |
| Example 40 | 4-Chloro-6-methyl-1H-indole-5-carboxylic acid (1-hydroxy-cyclohexylmethyl)-amide | e + c + VI | A | 0.74 | 321.16 |
| Example 41 | 4-Chloro-1H-indole-5-carboxylic acid (1-hydroxy-cyclopentylmethyl)-amide | 5 | E | 0.78 | 292.99 |

-continued

| Compound | Name | Purification method | LC-MS type | tR (min) | [M + H]+ |
|---|---|---|---|---|---|
| Example 42 | 4-Chloro-1H-indole-5-carboxylic acid (1-hydroxy-cyclooctylmethyl)-amide | 2 | E | 1.06 | 335.04 |
| Example 43 | 4-Chloro-1H-indole-5-carboxylic acid (1-methoxy-cyclohexylmethyl)-amide | 2 | E | 1.12 | 321.02 |
| Example 44 | 4-Chloro-1H-indole-5-carboxylic acid ((S)-1-cyclohexyl-ethyl)-amide | 3 | E | 1.28 | 305.02 |
| Example 45 | 4-Chloro-1H-indole-5-carboxylic acid ((R)-1-cyclohexyl-ethyl)-amide | 3 | E | 1.28 | 305.01 |
| Example 46 | 4-Chloro-1H-indole-5-carboxylic acid (1-acetylamino-cyclohexylmethyl)-amide | see below under section B | | | |
| Example 47 | 4-Chloro-1H-indole-5-carboxylic acid (1-methanesulfonylamino-cyclohexylmethyl)-amide | see below under section B | | | |
| Example 48 | 4-Chloro-1H-indole-5-carboxylic acid (1-dimethylamino-cyclohexylmethyl)-amide | see below under section B | | | |
| Example 49 | 4-Chloro-1H-indole-5-carboxylic acid (1-benzylamino-cyclohexylmethyl)-amide | see below under section B | | | |
| Example 50 | 3-Bromo-4-chloro-7-methyl-1H-indole-5-carboxylic acid (1-hydroxy-cyclohexylmethyl)-amide | VII | A | 0.83 | 398.78 |
| Example 51 | (1-{[(4-Chloro-1H-indole-5-carbonyl)-amino]-methyl}-cyclohexylsulfamoyl)-acetic acid methyl ester | see below under section B | | | |
| Example 52 | 4-Chloro-7-isobutyl-1H-indol-5-carboxylic acid (1-hydroxy-cycloheptylmethyl)-amide | II | A | 0.90 | 376.94 |
| Example 53 | 4-Chloro-7-(3-methoxy-propyl)-1H-indole-5-carboxylic acid (1-hydroxy-cycloheptylmethyl)-amide | b | A | 0.83 | 393.05 |
| Example 54 | 4-Chloro-7-isobutyl-1H-indole-5-carboxylic acid (4,4-difluoro-1-hydroxy-cyclohexylmethyl)-amide | b | A | 0.87 | 398.97 |
| Example 55 | 4-Chloro-7-(3-methoxy-propyl)-1H-indole-5-carboxylic acid (4,4-difluoro-1-hydroxy-cyclohexylmethyl)-amide | b | A | 0.80 | 415.03 |
| Example 56 | 4-Chloro-1H-indole-5-carboxylic acid [1-(2-hydroxy-ethanesulfonylamino)-cyclohexylmethyl]-amide | see below under section B | | | |
| Example 57 | 4-Methyl-1H-indole-5-carboxylic acid (1-hydroxy-cyclohexylmethyl)-amide | d | A | 0.70 | 287.18 |
| Example 58 | 4-Chloro-1H-indole-5-carboxylic acid [1-(2-methyl-pyrimidin-5-yl)-cyclohexylmethyl]-amide | precipitate from MeCN | A | 0.76 | 382.98 |
| Example 59 | 4-Chloro-7-methoxy-1H-indole-5-carboxylic acid (4,4-difluoro-1-hydroxy-cyclohexylmethyl)-amide | b | A | 0.76 | 372.88 |
| Example 60 | 4-Chloro-1H-indole-5-carboxylic acid [4,4-difluoro-1-(2-methyl-pyrimidin-5-yl)-cyclohexylmethyl]-amide | b + e | A | 0.76 | 418.89 |
| Example 61 | 4-Chloro-7-methyl-1H-indole-5-carboxylic acid [4,4-difluoro-1-(2-methyl-pyrimidin-5-yl)-cyclohexylmethyl]-amide | c | A | 0.79 | 432.90 |
| Example 62 | 4-Chloro-7-methyl-1H-indole-5-carboxylic acid [1-(2-methyl-pyrimidin-5-yl)-cyclohexylmethyl]-amide | b | A | 0.79 | 397.01 |

-continued

| Compound | Name | Purification method | LC-MS type | tR (min) | [M + H]+ |
|---|---|---|---|---|---|
| Example 63 | 4,7-Dimethyl-1H-indole-5-carboxylic acid (4,4-difluoro-1-hydroxy-cyclohexylmethyl)-amide | b | A | 0.75 | 336.98 |
| Example 64 | 4-Methyl-1H-indole-5-carboxylic acid (4,4-difluoro-1-hydroxy-cyclohexylmethyl)-amide | b + a | A | 0.72 | 322.95 |
| Example 65 | 4-Ethyl-1H-indole-5-carboxylic acid (4,4-difluoro-1-hydroxy-cyclohexylmethyl)-amide | d | A | 0.76 | 337.08 |
| Example 66 | 7-Acetyl-4-chloro-1H-indole-5-carboxylic acid (4,4-difluoro-1-hydroxy-cyclohexylmethyl)-amide | b | A | 0.77 | 384.97 |
| Example 67 | rac-4-Chloro-7-(1-hydroxy-ethyl)-1H-indole-5-carboxylic acid (4,4-difluoro-1-hydroxy-cyclohexylmethyl)-amide | see below under section B | | | |
| Example 68 | 4-Chloro-7-(1-hydroxy-1-methyl-ethyl)-1H-indole-5-carboxylic acid (4,4-difluoro-1-hydroxy-cyclohexylmethyl)-amide | see below under section B | | | |
| Example 69 | 7-Methyl-4-trifluoromethyl-1H-indole-5-carboxylic acid (1-hydroxy-cyclohexylmethyl)-amide | b | A | 0.79 | 354.96 |
| Example 70 | 7-Methyl-4-trifluoromethyl-1H-indole-5-carboxylic acid (4,4-difluoro-1-hydroxy-cyclohexylmethyl)-amide | b | A | 0.80 | 391.02 |
| Example 71 | 4,7-Dimethyl-1H-indole-5-carboxylic acid (1-hydroxy-cyclohexylmethyl)-amide | b | A | 0.74 | 301.13 |
| Example 72 | 4-Chloro-7-ethyl-1H-indole-5-carboxylic acid (1-hydroxy-cyclohexylmethyl)-amide | b | A | 0.80 | 335.02 |
| Example 73 | 4-Chloro-7-ethyl-1H-indole-5-carboxylic acid (4,4-difluoro-1-hydroxy-cyclohexylmethyl)-amide | b | A | 0.80 | 370.94 |
| Example 74 | 7-Chloro-4-methyl-1H-indole-5-carboxylic acid (1-hydroxy-cyclohexylmethyl)-amide | b | A | 0.77 | 321.04 |
| Example 75 | 7-Chloro-4-methyl-1H-indole-5-carboxylic acid (4,4-difluoro-1-hydroxy-cyclohexylmethyl)-amide | b | A | 0.78 | 356.95 |
| Example 76 | 4-Chloro-7-methoxy-1H-indole-5-carboxylic acid (1-hydroxy-cyclohexylmethyl)-amide | b | A | 0.76 | 336.98 |
| Example 77 | 7-Methoxy-4-methyl-1H-indole-5-carboxylic acid (4,4-difluoro-1-hydroxy-cyclohexylmethyl)-amide | b – e | A | 0.74 | 353.14 |
| Example 78 | 7-Methoxy-4-methyl-1H-indole-5-carboxylic acid (1-hydroxy-cyclohexylmethyl)-amide | b – e | A | 0.73 | 317.09 |
| Example 79 | 4-Chloro-7-ethoxy-1H-indole-5-carboxylic acid (1-hydroxy-cyclohexylmethyl)-amide | b | A | 0.80 | 350.92 |
| Example 80 | 4-Chloro-7-hydroxy-1H-indole-5-carboxylic acid (4,4-difluoro-1-hydroxy-cyclohexylmethyl)-amide | VIII | A | 0.71 | 359.03 |
| Example 81 | 4-Chloro-7-ethoxy-1H-indole-5-carboxylic acid (4,4-difluoro-1-hydroxy-cyclohexylmethyl)-amide | precipitate from DCM | A | 0.80 | 387.27 |
| Example 82 | 4-Chloro-7-propyl-1H-indole-5-carboxylic acid (1-hydroxy-cyclohexylmethyl)-amide | b | A | 0.84 | 349.21 |

-continued

| Compound | Name | Purification method | LC-MS type | tR (min) | [M + H]+ |
|---|---|---|---|---|---|
| Example 83 | 4-Chloro-7-propyl-1H-indole-5-carboxylic acid (4,4-difluoro-1-hydroxy-cyclohexylmethyl)-amide | b | A | 0.84 | 385.19 |
| Example 84 | 7-(2-tert-Butoxy-ethoxy)-4-chloro-1H-indole-5-carboxylic acid (1-hydroxy-cyclohexylmethyl)-amide | b | A | 0.86 | 423.07 |
| Example 85 | 7-(2-tert-Butoxy-ethoxy)-4-chloro-1H-indole-5-carboxylic acid (4,4-difluoro-1-hydroxy-cyclohexylmethyl)-amide | VII | A | 0.86 | 459.03 |
| Example 86 | 4-Chloro-7-(2-hydroxy-ethoxy)-1H-indole-5-carboxylic acid (1-hydroxy-cyclohexylmethyl)-amide | see below under section B | | | |
| Example 87 | 4-Chloro-7-(2-hydroxy-ethoxy)-1H-indole-5-carboxylic acid (4,4-difluoro-1-hydroxy-cyclohexylmethyl)-amide | see below under section B | | | |
| Example 88 | 7-Acetyl-4-chloro-1H-indole-5-carboxylic acid (1-hydroxy-cyclohexylmethyl)-amide | d | A | 0.76 | 349.20 |
| Example 89 | 4-Chloro-7-(1-hydroxy-1-methyl-ethyl)-1H-indole-5-carboxylic acid (1-hydroxy-cyclohexylmethyl)-amide | see below under section B | | | |
| Example 90 | 4,7-Difluoro-1H-indole-5-carboxylic acid (1-hydroxy-cyclohexylmethyl)-amide | b | A | 0.76 | 309.21 |
| Example 91 | 4,7-Difluoro-1H-indole-5-carboxylic acid (4,4-difluoro-1-hydroxy-cyclohexylmethyl)-amide | b | A | 0.77 | 345.23 |
| Example 92 | 4-Fluoro-7-methoxy-1H-indole-5-carboxylic acid (1-hydroxy-cyclohexylmethyl)-amide | b | A | 0.76 | 321.09 |
| Example 93 | 4-Fluoro-7-methoxy-1H-indole-5-carboxylic acid (4,4-difluoro-1-hydroxy-cyclohexylmethyl)-amide | b | A | 0.77 | 357.04 |
| Example 94 | 4-Chloro-7-(2-ethoxy-ethyl)-1H-indole-5-carboxylic acid (4,4-difluoro-1-hydroxy-cyclohexylmethyl)-amide | g | A | 0.81 | 415.23 |
| Example 95 | 4-Chloro-7-(1-methoxy-1-methyl-ethyl)-1H-indole-5-carboxylic acid (4,4-difluoro-1-hydroxy-cyclohexylmethyl)-amide | d | A | 0.82 | 415.21 |

B. Post Amide Coupling Steps

Example 21

4-Chloro-2-hydroxy-1H-indole-5-carboxylic acid (1-hydroxy-cycloheptylmethyl)-amide 21.1 3,3-Dibromo-4-chloro-N-((1-hydroxycycloheptyl)methyl)-2-oxoindoline-5-carboxamide To a suspension of 4-chloro-1H-indole-5-carboxylic acid (1-hydroxy-cycloheptylmethyl)-amide (Example 3) (0.143 mmol) in tert-butanol (0.3 mL) was added pyridinium tribromide (0.456 mmol). The mixture was stirred for 30 min at RT, concentrated in vacuo and partitioned between EtOAc and water. The organic phase was dried over $MgSO_4$ and concentrated in vacuo. The crude was precipitated from $CH_3CN$/DMF and the solid washed with EtOH to give the title compound as yellowish solid.

LC-MS (A): $t_R$=0.78 min; [M+H]+: 494.94

21.2 4-Chloro-2-hydroxy-1H-indole-5-carboxylic acid (1-hydroxy-cycloheptylmethyl)-amide To a suspension of 3,3-dibromo-4-chloro-N4(1-hydroxy-cycloheptyl)methyl)-2-oxoindoline-5-carboxamide (intermediate 21.1) (0.036 mmol) in AcOH (0.33 mL) was added portionwise zinc dust (0.364 mmol). The mixture was stirred for 15 min at RT, filtered over a pad of celite and the cake washed with EtOAc. The filtrate was concentrated in vacuo and the crude was purified by CC using EtOAc to give the title compound as white solid.

LC-MS (A): $t_R$=0.65 min; [M+H]+: 337.04

Example 31

4-Chloro-1H-indole-5-carboxylic acid (1-hydroxymethyl-cyclohexyl methyl)-amide To a suspension of lithium aluminum hydride (0.172 mmol of a 1M solution in THF) in THF (0.5 mL) was added dropwise at 0° C. a solution of 1-{[(4-chloro-1H-indole-5-carbonyl)-amino]-methyl}-cyclohexanecarboxylic acid methyl ester (Example 30) (0.086 mmol) in THF (0.2 mL). The mixture was stirred for 5 min at 0° C. and 1 h at RT, cooled to 0° C. and quenched by the consecutive addition of water (0.043 mL) and of a 1M aqueous solution of NaOH (0.043 mL). It was extracted 3 times with EtOAc and washed with brine. The organic phases were dried over $MgSO_4$ and concentrated in vacuo. The crude was purified by CC using DCM/MeOH 95/5 to give the title compound as white solid.

LC-MS (A): $t_R$=0.79 min; [M+H]+: 321.17

Example 32

7-Amino-4-chloro-1H-indole-5-carboxylic acid (1-hydroxy-cyclohexyl methyl)-amide To a solution of 4-chloro-7-nitro-1H-indole-5-carboxylic acid (1-hydroxy-cyclohexylmethyl)-amide (Example 29) (0.043 mmol) in DMF (0.085 mL) was added tin (II) chloride dihydrate (0.128 mmol). The mixture was stirred ON at RT and quenched with water. It was basified with a 1M solution of NaOH and extracted with DCM. The organic phase was dried over $MgSO_4$ and concentrated in vacuo. The crude was purified by preparative LC-MS using method IV to give the title compound as white solid.

LC-MS (A): $t_R$=0.64 min; [M+H]+: 321.90

Example 34

4-Chloro-1H-indole-5-carboxylic acid (1-carbamoyl-cyclohexylmethyl)-amide

34.1 1-{[(4-Chloro-1H-indole-5-carbonyl)-amino]-methyl}-cyclohexanecarboxylic acid This compound was prepared using a method analogous to that of 4-chloro-1H-indole-5-carboxylic acid, 1-{[(4-chloro-1H-indole-5-carbonyl)-amino]-methyl}-cyclohexane carboxylic acid methyl ester (Example 30) replacing methyl 4-chloro-1H-indole-5-carboxylate.

LC-MS (A): $t_R$=0.75 min; [M+H]+: 335.11

34.1 4-Chloro-1H-indole-5-carboxylic acid (1-carbamoyl-cyclohexylmethyl)-amide This compound was prepared according to the general procedure V for amide coupling engaging 1-{[(4-chloro-1H-indole-5-carbonyl)-amino]-methyl}-cyclohexanecarboxylic acid as carboxylic acid and ammonium hydroxide as amine.

LC-MS (A): $t_R$=0.68 min; [M+H]+: 334.20

Example 35

4-Chloro-1H-indole-5-carboxylic acid (1-methylcarbamoyl-cyclohexylmethyl)-amide This compound was prepared according to the general procedure V for amide coupling engaging 1-{[(4-chloro-1H-indole-5-carbonyl)-amino]-methyl}-cyclohexanecarboxylic acid as carboxylic acid and methylamine (as a 2M solution in THF) as amine.

LC-MS (A): $t_R$=0.71 min; [M+H]+: 348.16

Example 36

4-Chloro-1H-indole-5-carboxylic acid (1-cyano-cyclohexylmethyl)-amide

To a solution of 4-chloro-1H-indole-5-carboxylic acid (1-carbamoyl-cyclohexylmethyl)-amide (Example 34) (0.090 mmol) in DCM (1 mL) was added under argon Burgess reagent (0.180 mmol). The mixture was stirred for 1 h 30 at RT and for 3 h at 50° C. and quenched with water. It was extracted 3 times with DCM and the combined organic phases were dried over $MgSO_4$ and concentrated in vacuo. The crude was purified by CC using DCM/MeOH from 100/0 to 97/3 to give the title compound as white solid.

LC-MS (A): $t_R$=0.80 min; [M+H]+: 316.19

Example 39

4-Chloro-1H-indole-5-carboxylic acid (1-amino-cyclohexylmethyl)-amide hydrochloride To a solution of (1-{[(4-chloro-1H-indole-5-carbonyl)-amino]-methyl}-cyclohexyl)-carbamic acid tert-butyl ester (Example 37) (1.42 mmol) in EtOAc (10 mL) was added dropwise a 4M solution of HCl in dioxane (14.2 mmol). The mixture was stirred ON at RT and concentrated in vacuo. The residue was precipitated from $Et_2O/CH_3CN$ to give the title compound as light pink solid.

LC-MS (A): $t_R$=0.58 min; [M+H]+: 306.00

Example 46

4-Chloro-1H-indole-5-carboxylic acid (1-acetylamino-cyclohexylmethyl)-amide

To a suspension of 4-chloro-1H-indole-5-carboxylic acid (1-amino-cyclohexylmethyl)-amide hydrochloride (Example 39) (0.116 mmol) and $Et_3N$ (0.578 mmol) in DCM (1 mL) was added at 0° C. acetyl chloride (0.139 mmol). The mixture was stirred for 40 min at 0° C., quenched with a sat. solution of $NaHCO_3$ and extracted 3 times with EtOAc. The combined organic phases were washed with brine, dried over $MgSO_4$ and concentrated in vacuo. The crude was purified by CC (SNAP KP-SIL™ from Biotage) using Hept./EtOAc/MeOH from 100/0/0 to 20/76/4 to give the title compound as white solid.

LC-MS (A): $t_R$=0.73 min; [M+H]+: 348.08

Example 47

4-Chloro-1H-indole-5-carboxylic acid (1-methanesulfonylamino-cyclohexylmethyl)-amide To a suspension of 4-chloro-1H-indole-5-carboxylic acid (1-amino-cyclohexylmethyl)-amide hydrochloride (Example 39) (0.116 mmol) and $Et_3N$ (0.578 mmol) in DCM (1 mL) was added at 0° C. methanesulfonyl chloride (0.139 mmol). The mixture was stirred for 40 min at 0° C., quenched with a sat. solution of $NaHCO_3$ and extracted 3 times with EtOAc. The combined organic phases were washed with brine, dried over $MgSO_4$ and concentrated in vacuo. The crude was purified by CC (SNAP KP-SIL™ from Biotage) using Hept./EtOAc/MeOH from 100/0/0 to 20/76/4 to give the title compound as light beige solid.
LC-MS (A): $t_R$=0.75 min; [M+H]+: 383.93

Example 48

4-Chloro-1H-indole-5-carboxylic acid (1-dimethylamino-cyclohexylmethyl)-amide

To a solution of 4-chloro-1H-indole-5-carboxylic acid (1-amino-cyclohexylmethyl)-amide hydrochloride (Example 39) (0.433 mmol) in DCM (4 mL) and MeOH (6 mL) was added AcOH (0.520 mmol) followed by a 37% aqueous solution of formaldehyde (0.477 mmol) and by sodium triacetoxyborohydride (0.607 mmol). The mixture was stirred for 2 h at RT and an additional amount of a 37% aqueous solution of formaldehyde (0.200 mmol) was added. It was stirred for 1 h at RT, quenched with a sat. solution of NaHCO$_3$ and extracted 3 times with EtOAc. The combined organic phases were dried over MgSO$_4$ and concentrated in vacuo. The crude was purified by CC (SNAP KP-NH™ from Biotage) using Hept./EtOAc/MeOH from 100/0/0 to 0/95/5 to give the title compound as white solid.
LC-MS (A): $t_R$=0.60 min; [M+H]+: 334.18

Example 49

4-Chloro-1H-indole-5-carboxylic acid (1-benzylamino-cyclohexylmethyl)-amide

To a solution of 4-chloro-1H-indole-5-carboxylic acid (1-amino-cyclohexylmethyl)-amide hydrochloride (Example 39) (0.144 mmol) in DCM (1 mL) was added AcOH (0.159 mmol) followed by benzaldehyde (0.173 mmol) and by sodium triacetoxyborohydride (0.296 mmol). The mixture was stirred for 2 h at RT and ON at 60° C. Additional amounts of sodium triacetoxyborohydride (2×0.471 mmol) was added and the mixture stirred for 5 h at 60° C. and ON at RT. It was quenched with a sat. solution of NaHCO$_3$ and extracted 3 times with EtOAc. The combined organic phases were dried over MgSO$_4$ and concentrated in vacuo. The crude was purified by preparative LC-MS using method VI and additionally by CC (Isolute™ NH$_2$ from Biotage) using EtOAc to give the title compound as white solid.
LC-MS (A): $t_R$=0.73 min; [M+H]+: 396.05

Example 51

(1-{[(4-Chloro-1H-indole-5-carbonyl)-amino]-methyl}-cyclohexylsulfamoyl)-acetic acid methyl ester This compound was prepared using a method analogous to that of Example 47, methyl chlorosulfonylacetate replacing methanesulfonyl chloride except that the mixture was stirred for 1.5 h at 0° C.
LC-MS (A): $t_R$=0.80 min; [M+H]+: 441.90

Example 56

4-Chloro-1H-indole-5-carboxylic acid [1-(2-hydroxy-ethanesulfonylamino)-cyclohexylmethyl]-amide This compound was prepared using a method analogous to that of Example 31, (1-{[(4-chloro-1H-indole-5-carbonyl)-amino]-methyl}-cyclohexylsulfamoyl)-acetic acid methyl ester (Example 51) replacing 1-{[(4-chloro-1H-indole-5-carbonyl)-amino]-methyl}-cyclohexanecarboxylic acid methyl ester (Example 30).
LC-MS (A): $t_R$=0.70 min; [M+H]+: 413.97

Example 67 rac-4-Chloro-7-(1-hydroxy-ethyl)-1H-indole-5-carboxylic acid (4,4-difluoro-1-hydroxy-cyclohexylmethyl)-amide To as suspension of 7-acetyl-4-chloro-1H-indole-5-carboxylic acid (4,4-difluoro-1-hydroxy-cyclohexylmethyl)-amide (example 66) (0.08 mmol) in MeOH (1 mL) was added sodium borohydride (0.18 mmol). The mixture was stirred for 5 h at RT, quenched with water and extracted three times with EtOAc. The organic phases were washed with brine, dried over MgSO$_4$ and concentrated in vacuo. The crude was purified by CC (Isolute™ Silica II from Biotage) using DCM/MeOH from 95/5 to 93/7 to give the title compound as white solid.
LC-MS (A): $t_R$=0.71 min; [M+H]+: 387.23

Example 68

4-Chloro-7-(1-hydroxy-1-methyl-ethyl)-1H-indole-5-carboxylic acid (4,4-difluoro-1-hydroxy-cyclohexylmethyl)-amide To a solution of 7-acetyl-4-chloro-1H-indole-5-carboxylic acid (4,4-difluoro-1-hydroxy-cyclohexylmethyl)-amide (example 66) (0.08 mmol) in THF (1.5 mL) was added dropwise at −10° C. a 3M solution of methylmagnesium bromide in diethyl ether (0.15 mmol). The mixture was stirred for 5 h at RT and an additional amount of a 3M solution of methylmagnesium bromide in diethyl ether (0.60 mmol) was added at RT. The mixture was further stirred ON at RT and cooled to 0° C. It was quenched with a sat. solution of NH$_4$Cl and extracted three times with EtOAc. The organic phases were washed with brine, dried over MgSO$_4$ and concentrated in vacuo. The crude was purified by CC (Isolute™ Silica II from Biotage) using DCM/MeOH 95/5 to 93/7 to give the title compound as light yellow solid.
LC-MS (A): $t_R$=0.74 min; [M+H]+: 401.18

Example 86

4-Chloro-7-(2-hydroxy-ethoxy)-1H-indole-5-carboxylic acid (1-hydroxy-cyclohexylmethyl)-amide A solution of 7-(2-tert-butoxy-ethoxy)-4-chloro-1H-indole-5-carboxylic acid (1-hydroxy-cyclohexylmethyl)-amide (example 84) (0.08 mmol) in DCM (0.33 mL) was treated with TFA (4.14 mmol). The mixture was stirred for 2 h 30 min at RT, concentrated in vacuo and coevaporated with toluene. The crude was purified by preparative LC-MS using method VIII to give the title compound as white solid.
LC-MS (A): $t_R$=0.69 min; [M+H]+: 367.03

Example 87

4-Chloro-7-(2-hydroxy-ethoxy)-1H-indole-5-carboxylic acid (4,4-difluoro-1-hydroxy-cyclohexylmethyl)-amide This compound was prepared using a method analogous to that of example 86, 7-(2-tert-butoxy-ethoxy)-4-chloro- 1H-indole-5-carboxylic acid (4,4-difluoro-1-hydroxy-cyclohexylmethyl)-amide (example 85) replacing 7-(2-tert-butoxy-ethoxy)-4-chloro-1H-indole-5-carboxylic acid (1-hydroxy-cyclohexylmethyl)-amide (example 84).

LC-MS (A): $t_R$=0.70 min; [M+H]+: 403.02

Example 89

4-Chloro-7-(1-hydroxy-1-methyl-ethyl)-1H-indole-5-carboxylic acid (1-hydroxy-cyclohexylmethyl)-amide This compound was prepared using a method analogous to that of example 68, 7-acetyl-4-chloro-1H-indole-5-carboxylic acid (1-hydroxy-cyclohexylmethyl)-amide (example 88) replacing 7-acetyl-4-chloro-1H-indole-5-carboxylic acid (4,4-difluoro-1-hydroxy-cyclohexylmethyl)-amide (example 66).

LC-MS (A): $t_R$=0.73 min, [M+H]+: 365.27

II. BIOLOGICAL ASSAYS

A. In Vitro Assay

The $P2X_7$ receptor antagonistic activity of the compounds of formula (I) is determined in accordance with the following experimental method.

B. Experimental Method

Cell line generation and YO-PRO assay

Cell line generation was performed in general according to established molecular cloning protocols. Specifically, RNA was extracted from human whole blood using the Qiagen RNeasy kit (Qiagen, CH) according to the manufacturer's instructions. Subsequently cDNA was made (Superscript II, Invitrogen AG, CH) and the human P2X7 gene (genbank ref. BC011913) was amplified with the following primers:

```
ATCGCGGCCGCTCAGTAAGGACTCTTGAAGCCACT
and

CGCCGCTAGCACCACCATGCCGGCCTGCTGCAGCTGCA.
```

The amplified sequence was subsequently ligated into a pcDNA3.1 (+) NotI, NheI digested plasmid. Human embryonic kidney (HEK) cells (ATCC CRL-1573, Manassas, Va., USA) were transfected with the pcDNA3.1 (+).hP2X7 plasmid using lipofectamine 2000 (Invitrogen AG, CH) according to the manufacturer's instructions. Following a 24 h exposure to DNA, cells were trypsinized and re-seeded at low density in the presence of 250 μg Geneticin. Geneticin resistant cells were then selected during two consecutive rounds of cloning by serial limiting dilution with visual inspection. Individual clones were screened for P2X7 expression by applying ATP and recording the resultant uptake of YO-PRO1. Specific cell clones were chosen based on RNA and protein expression. HEK cells stably expressing P2X7 were used to screen drugs using the YO-PRO1 assay. Cells were grown to confluency in adherent culture at 37° C. in a humidified 5% $CO_2$ incubator (split 1/5 every 3-4 days with DMEM, 10% FCS, 1% Penicillin/Streptomycin, 250 μg/ml Geneticin). Adherent cells were detached by incubation with Trypsine (1 ml per 165 $cm^2$ dish) for 2 minutes, then washed off with 10 ml PBS (without $Mg^{2+}$ and $Ca^{2+}$), and resuspended in DMEM, 10% FCS, 1% Penicillin/Streptomycin, no Geneticin. 10'000 cells per well (48 hours before the assay) or 25'000 cells per well (Vi-cell XR (Beckman Coulter) (24 hours before the assay) in 50 μl full medium were seeded on 384-well black-wall, clear bottom plates, that were coated before with 10 μl per well Poly-L-Lysine, incubated for 30-60 minutes at 37° C. and washed once with PBS. Medium was removed from cells and 50 μl of assay buffer containing 0.5 μM YO-PRO-1 was added into the wells. Solutions of antagonist compounds were prepared by serial dilutions of a 10 mM DMSO solution of the antagonist into PBS using a BioMek (Beckman Coulter). Each concentration was performed in duplicate. For $IC_{50}$ measurements 10 concentration points were measured (10 μM being the highest concentration followed by 9 serial dilution steps 1/3). The cells were incubated with the antagonists of the present invention together with ATP at a final concentration of 250 μM for 90 minutes. During this time period, four time points were taken. Each time point comprised the average of several measurements made within a few seconds. Fluorescence was measured in the FLIPR tetra (Molecular Devices) using the filters appropriate for YO-PRO-1 fluorescence (excitation485/20, emission 530/25). The FLIPR tetra was equipped with Molecular Devices Screen Works system control software to define and run experimental protocols. For antagonist activity measurements, the maximal intensity was expressed as a percentage of that induced by the $EC_{50}$ value for agonist activation (0.25 mM ATP for HEK-293 cells expressing human recombinant P2X7 receptor). For IC50 measurements the maximum intensity is plotted against the concentration of compound to determine IC50 values.

Antagonistic activities with respect to the $P2X_7$ receptor ($IC_{50}$ values) of exemplified compounds are displayed in Table 1.

TABLE 1

| Compound | $IC_{50}$ [nM] | Compound | $IC_{50}$ [nM] | Compound | $IC_{50}$ [nM] |
|---|---|---|---|---|---|
| Example 1 | 13 | Example 2 | 35 | Example 3 | 12 |
| Example 4 | 42 | Example 5 | 77 | Example 6 | 211 |
| Example 7 | 50 | Example 8 | 198 | Example 9 | 1152 |
| Example 10 | 57 | Example 11 | 4.1 | Example 12 | 3.2 |
| Example 13 | 17 | Example 14 | 4.5 | Example 15 | 238 |
| Example 16 | 442 | Example 17 | 14 | Example 18 | 178 |
| Example 19 | 18 | Example 20 | 6.1 | Example 21 | 302 |
| Example 22 | 1183 | Example 23 | 1147 | Example 24 | 4.7 |
| Example 25 | 2.9 | Example 26 | 11.4 | Example 27 | 682 |
| Example 28 | 151 | Example 29 | 20 | Example 30 | 221 |
| Example 31 | 38 | Example 32 | 11 | Example 33 | 44 |
| Example 34 | 130 | Example 35 | 666 | Example 36 | 27 |
| Example 37 | 420 | Example 38 | 1315 | Example 39 | 1558 |
| Example 40 | 1600 | Example 41 | 264 | Example 42 | 14 |
| Example 43 | 218 | Example 44 | 1427 | Example 45 | 81 |
| Example 46 | 209 | Example 47 | 21 | Example 48 | 1083 |
| Example 49 | 497 | Example 50 | 246 | Example 51 | 24 |
| Example 52 | 5.9 | Example 53 | 4.4 | Example 54 | 13 |
| Example 55 | 6.7 | Example 56 | 9.0 | Example 57 | 68 |
| Example 58 | 6.4 | Example 59 | 5.4 | Example 60 | 6.3 |
| Example 61 | 4.0 | Example 62 | 4.1 | Example 63 | 4.0 |
| Example 64 | 51 | Example 65 | 79 | Example 66 | 24 |
| Example 67 | 4.7 | Example 68 | 7.2 | Example 69 | 10 |
| Example 70 | 10 | Example 71 | 12 | Example 72 | 4.1 |
| Example 73 | 4.2 | Example 74 | 17 | Example 75 | 9.5 |
| Example 76 | 2.9 | Example 77 | 21 | Example 78 | 21 |
| Example 79 | 6.1 | Example 80 | 100 | Example 81 | 5.4 |
| Example 82 | 3.8 | Example 83 | 3.3 | Example 84 | 25 |
| Example 85 | 30 | Example 86 | 6.7 | Example 87 | 7.3 |
| Example 88 | 25 | Example 89 | 8.3 | Example 90 | 563 |
| Example 91 | 701 | Example 92 | 45 | Example 93 | 70 |
| Example 94 | 9.4 | Example 95 | 9.3 | | |

The invention claimed is:

1. A compound of the formula (I),

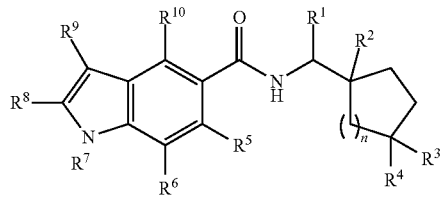

wherein
n represents 1, 2, 3 or 4;
$R^1$ represents hydrogen and $R^2$ represents hydroxy; hydroxy-$(C_1$-$C_3)$alkyl; $(C_1$-$C_3)$alkoxy; —$NHR^{11}$; —$N(CH_3)_2$; —CN; —$CONH_2$; $(C_1$-$C_4)$alkoxy-carbonyl; $(C_1$-$C_4)$alkylamino-carbonyl; aryl which is unsubstituted or mono- or di-substituted with $(C_1$-$C_3)$fluoroalkyl or halogen; or heteroaryl which is unsubstituted or mono- or di-substituted with $(C_1$-$C_4)$alkyl, $(C_1$-$C_3)$ fluoroalkyl or halogen; or
$R^1$ represents $(C_1$-$C_3)$alkyl or hydroxy-$(C_1$-$C_3)$alkyl and $R^2$ represents hydrogen;
$R^3$ represents hydrogen or fluoro;
$R^4$ represents hydrogen or fluoro;
$R^5$ represents hydrogen, $(C_1$-$C_4)$alkyl or halogen;
$R^6$ represents hydrogen, $(C_1$-$C_4)$alkyl, $(C_1$-$C_4)$alkoxy, $(C_1$-$C_4)$alkyl-carbonyl, hydroxy-$(C_1$-$C_4)$alkyl, hydroxy-$(C_2$-$C_4)$alkoxy, $(C_1$-$C_2)$alkoxy-$(C_1$-$C_4)$alkyl, $(C_1$-$C_4)$alkoxy-$(C_2$-$C_4)$alkoxy, hydroxy, amino, nitro or halogen;
$R^7$ represents hydrogen or $(C_1$-$C_3)$alkyl;
$R^8$ represents hydrogen, $(C_1$-$C_4)$alkyl or hydroxy;
$R^9$ represents hydrogen, $(C_1$-$C_4)$alkyl, $(C_1$-$C_4)$alkylthio, formyl or halogen;
$R^{10}$ represents fluoro, chloro, methyl, ethyl, $(C_1$-$C_2)$fluoroalkyl or methoxy; and
$R^{11}$ represents hydrogen, benzyl, $(C_1$-$C_4)$alkyl-carbonyl, $(C_1$-$C_4)$alkoxy-carbonyl or $(C_1$-$C_4)$alkyl-sulfonyl which is unsubstituted or mono-substituted with hydroxy or $(C_1$-$C_4)$alkoxy-carbonyl;
or a salt of such a compound.

2. The compound of formula (I) according to claim 1, wherein n represents 2, 3 or 4;
$R^1$ represents hydrogen;
$R^2$ represents hydroxy; hydroxy-$(C_1$-$C_3)$alkyl; —$NHR^{11}$; —CN; or a 5- or 6-membered monocyclic heteroaryl group which group is unsubstituted or mono-substituted with $(C_1$-$C_4)$alkyl, $(C_1$-$C_3)$ fluoroalkyl or halogen;
$R^3$ represents hydrogen or fluoro;
$R^4$ represents hydrogen or fluoro;
$R^5$ represents hydrogen;
$R^6$ represents hydrogen, $(C_1$-$C_4)$alkyl, $(C_1$-$C_4)$alkoxy or $(C_1$-$C_2)$alkoxy-$(C_1$-$C_4)$alkyl;
$R^7$ represents hydrogen;
$R^8$ represents hydrogen;
$R^9$ represents hydrogen, $(C_1$-$C_4)$alkyl or halogen;
$R^{10}$ represents chloro or methyl; and
$R^{11}$ represents $(C_1$-$C_4)$alkyl-sulfonyl which is unsubstituted or mono-substituted with hydroxy or $(C_1$-$C_4)$ alkoxy-carbonyl;
or a salt of such a compound.

3. The compound of formula (I) according to claim 1, wherein
n represents 2 or 3;
or a salt of such a compound.

4. The compound of formula (I) according to claim 1, wherein
$R^2$ represents hydroxy; hydroxy-$(C_1$-$C_3)$alkyl; —$NHR^{11}$; or —CN; and $R^{11}$ represents methyl-sulfonyl which is unsubstituted or mono-substituted with methoxy-carbonyl; or ethyl-sulfonyl which is mono-substituted with hydroxy;
or a salt of such a compound.

5. The compound of formula (I) according to claim 1, wherein
$R^2$ represents a 5- or 6-membered monocyclic heteroaryl group which group is unsubstituted or mono-substituted with $(C_1-C_4)$alkyl, $(C_1-C_3)$fluoroalkyl or halogen;
or a salt of such a compound.

6. The compound of formula (I) according to claim 1, wherein
$R^6$ represents $(C_1-C_4)$alkyl, $(C_1-C_4)$alkoxy or $(C_1-C_2)$alkoxy-$(C_1-C_4)$alkyl;
or a salt of such a compound.

7. The compound of formula (I) according to claim 1, wherein
$R^5$, $R^7$, $R^8$ and $R^9$ represent hydrogen;
or a salt of such a compound.

8. The compound of formula (I) according to claim 1, wherein
$R^{10}$ represents chloro;
or a salt of such a compound.

9. The compound of formula (I) according to claim 1, which is also a compound of formula ($I_{OH}$)

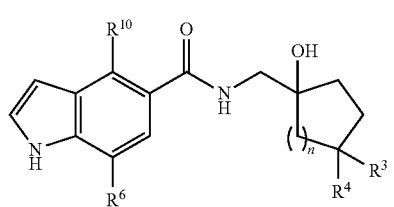

($I_{OH}$)

wherein
n represents 2 or 3;
$R^3$ represents hydrogen or fluoro;
$R^4$ represents hydrogen or fluoro;
$R^6$ represents $(C_1-C_4)$alkyl, $(C_1-C_4)$alkoxy, hydroxy-$(C_1-C_4)$alkyl, hydroxy-$(C_2-C_4)$alkoxy, $(C_1-C_2)$alkoxy-$(C_1-C_4)$alkyl or halogen; and
$R^{10}$ represents chloro, methyl or trifluoromethyl;
or a salt of such a compound.

10. The compound of formula (I) according to claim 1, which is also a compound of formula ($I_{HET}$)

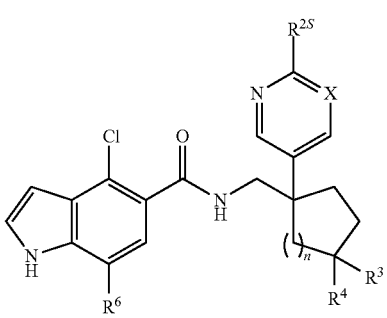

($I_{HET}$)

wherein
n represents 2 or 3;
X represents CH or N;
$R^{2S}$ represents hydrogen, $(C_1-C_4)$alkyl, $(C_1-C_3)$fluoroalkyl or halogen;
$R^3$ represents hydrogen or fluoro;
$R^4$ represents hydrogen or fluoro; and
$R^6$ represents hydrogen or $(C_1-C_4)$alkyl;
or a salt of such a compound.

11. The compound of formula (I) according to claim 1, selected from the group consisting of:
4-Chloro-1H-indole-5-carboxylic acid ((S)-1-cyclohexyl-2-hydroxy-ethyl)-amide;
4-Chloro-1H-indole-5-carboxylic acid (1-hydroxy-cyclohexylmethyl)-amide;
4-Chloro-1H-indole-5-carboxylic acid (1-hydroxy-cycloheptylmethyl)-amide;
4-Chloro-1H-indole-5-carboxylic acid (4,4-difluoro-1-hydroxy-cyclohexylmethyl)-amide;
4-Chloro-1H-indole-5-carboxylic acid [(S)-1-(4,4-difluoro-cyclohexyl)-2-hydroxy-ethyl]-amide;
4-Chloro-l-methyl-1H-indole-5-carboxylic acid (1-hydroxy-cyclohexylmethyl)-amide;
4-Chloro- 1-methyl- 1H-indole-5-carboxylic acid ((S)-1-cyclohexyl-2-hydroxy-ethyl)-amide;
4-Chloro-3-formyl- 1H-indole-5-carboxylic acid ((S)-1-cyclohexyl-2-hydroxy-ethyl)-amide;
4-Chloro-3-formyl-1H-indole-5-carboxylic acid (1-hydroxy-cyclohexylmethyl)-amide;
4-Chloro-1H-indole-5-carboxylic acid (1-cycloheptyl-2-hydroxy-ethyl)-amide;
4-Chloro-1H-indole-5-carboxylic acid [1-(2-trifluoromethyl-pyrimidin-5-yl)-cyclohexylmethyl]-amide;
4-Chloro-1H-indole-5-carboxylic acid [1-(6-chloro-pyridin-3-yl)-cyclohexylmethyl]-amide;
4-Chloro-1H-indole-5-carboxylic acid [1-(6-trifluoromethyl-pyridin-3-yl)-cyclohexylmethyl]-amide;
4-Chloro-1H-indole-5-carboxylic acid [1-(6-chloro-pyridin-3-yl)-4,4-difluoro-cyclohexylmethyl ]-amide;
4-Chloro-1H-indole-5-carboxylic acid [1-(4-chloro-phenyl)-cyclohexylmethyl]-amide;
4-Chloro-1H-indole-5-carboxylic acid [1-(4-trifluoromethyl-phenyl)-cyclohexylmethyl]-amide;
4-Chloro-1H-indole-5-carboxylic acid (1-pyridin-3-yl-cyclohexylmethyl)-amide;
4-Chloro-1H-indole-5-carboxylic acid (1-pyridin-3-yl-cyclopentylmethyl)-amide;
4-Chloro-1H-indole-5-carboxylic acid (1-pyridin-3-yl-cycloheptylmethyl)-amide;
4-Chloro-7-methyl-1H-indole-5-carboxylic acid (1-hydroxy-cyclohexylmethyl)-amide;
4-Chloro-2-oxo-2,3-dihydro-1H-indole-5-carboxylic acid (1-hydroxy-cycloheptylmethyl)-amide;
4-Chloro-2-methyl-1H-indole-5-carboxylic acid (1-hydroxy-cyclohexylmethyl)-amide;
4-Chloro-7-iodo-3-methylsulfanyl-1H-indole-5-carboxylic acid (1-hydroxy-cyclohexylmethyl)-amide;
4-Chloro-7-methyl-1H-indole-5-carboxylic acid (4,4-difluoro- 1 -hydroxy-cyclohexylmethyl)-amide;
4-Chloro-7-methyl-1H-indole-5-carboxylic acid (1-hydroxy-cycloheptylmethyl)-amide;
4-Chloro-3-fluoro-1H-indole-5-carboxylic acid (1-hydroxy-cycloheptylmethyl)-amide;
4-Methoxy-1H-indole-5-carboxylic acid (1-hydroxy-cycloheptylmethyl)-amide;
3,4-Dichloro-1H-indole-5-carboxylic acid (1-hydroxy-cyclohexylmethyl)-amide;
4-Chloro-7-nitro-1H-indole-5-carboxylic acid (1-hydroxy-cyclohexylmethyl)-amide;

1-{[(4-Chloro-1H-indole-5-carbonyl)-amino]-methyl}-cyclohexanecarboxylic acid methyl ester;
4-Chloro-1H-indole-5-carboxylic acid (1-hydroxymethyl-cyclohexylmethyl)-amide;
7-Amino-4-chloro-1H-indole-5-carboxylic acid (1-hydroxy-cyclohexylmethyl)-amide;
4-Chloro-3-methyl-1H-indole-5-carboxylic acid (1-hydroxy-cycloheptylmethyl)-amide;
4-Chloro-1H-indole-5-carboxylic acid (1-carbamoyl-cyclohexylmethyl)-amide;
4-Chloro-1H-indole-5-carboxylic acid (1-methylcarbamoyl-cyclohexylmethyl)-amide;
4-Chloro-1H-indole-5-carboxylic acid (1-cyano-cyclohexylmethyl)-amide;
(1-{[(4-Chloro-1H-indole-5-carbonyl)-amino]-methyl}-cyclohexyl)-carbamic acid tert-butyl ester;
4,6-Dichloro-1H-indole-5-carboxylic acid (4,4-difluoro-1-hydroxy-cyclohexylmethyl)-amide;
4-Chloro-1H-indole-5-carboxylic acid (1-amino-cyclohexylmethyl)-amide;
4-Chloro-6-methyl-1H-indole-5-carboxylic acid (1-hydroxy-cyclohexylmethyl)-amide;
4-Chloro-1H-indole-5-carboxylic acid (1-hydroxy-cyclopentylmethyl)-amide;
4-Chloro-1H-indole-5-carboxylic acid (1-hydroxy-cyclooctylmethyl)-amide;
4-Chloro-1H-indole-5-carboxylic acid (1-methoxy-cyclohexylmethyl)-amide;
4-Chloro-1H-indole-5-carboxylic acid ((S)-1-cyclohexyl-ethyl)-amide;
4-Chloro-1H-indole-5-carboxylic acid ((R)-1-cyclohexyl-ethyl)-amide;
4-Chloro-1H-indole-5-carboxylic acid (1-acetylamino-cyclohexylmethyl)-amide;
4-Chloro-1H-indole-5-carboxylic acid (1-methanesulfonylamino-cyclohexylmethyl)-amide;
4-Chloro-1H-indole-5-carboxylic acid (1-dimethylamino-cyclohexylmethyl)-amide;
4-Chloro-1H-indole-5-carboxylic acid (1-benzylamino-cyclohexylmethyl)-amide;
3-Bromo-4-chloro-7-methyl-1H-indole-5-carboxylic acid (1-hydroxy-cyclohexylmethyl)-amide;
(1-{[(4-Chloro-1H-indole-5-carbonyl)-amino]-methyl}-cyclohexylsulfamoyl)-acetic acid methyl ester;
4-Chloro-7-isobutyl-1H-indole-5-carboxylic acid (1-hydroxy-cycloheptylmethyl)-amide;
4-Chloro-7-(3-methoxy-propyl)-1H-indole-5-carboxylic acid (1-hydroxy-cycloheptylmethyl)-amide;
4-Chloro-7-isobutyl-1H-indole-5-carboxylic acid (4,4-difluoro-1-hydroxy-cyclohexylmethyl)-amide;
4-Chloro-7-(3-methoxy-propyl)-1H-indole-5-carboxylic acid (4,4-difluoro-1-hydroxy-cyclohexylmethyl)-amide;
4-Chloro-1H-indole-5-carboxylic acid [1-(2-hydroxy-ethanesulfonylamino)-cyclohexylmethyl]-amide;
4-Methyl-1H-indole-5-carboxylic acid (1-hydroxy-cyclohexylmethyl)-amide;
4-Chloro-1H-indole-5-carboxylic acid [1-(2-methyl-pyrimidin-5-yl)-cyclohexylmethyl]-amide;
4-Chloro-7-methoxy-1H-indole-5-carboxylic acid (4,4-difluoro-1-hydroxy-cyclohexylmethyl)-amide;
4-Chloro-1H-indole-5-carboxylic acid [4,4-difluoro-1-(2-methyl-pyrimidin-5-yl)-cyclohexylmethyl]-amide;
4-Chloro-7-methyl-1H-indole-5-carboxylic acid [4,4-difluoro-1-(2-methyl-pyrimidin-5-yl)-cyclohexylmethyl]-amide;
4-Chloro-7-methyl-1H-indole-5-carboxylic acid [1-(2-methyl-pyrimidin-5-yl)-cyclohexylmethyl]-amide;
4,7-Dimethyl-1H-indole-5-carboxylic acid (4,4-difluoro-1-hydroxy-cyclohexylmethyl)-amide;
4-Methyl-1H-indole-5-carboxylic acid (4,4-difluoro-1-hydroxy-cyclohexylmethyl)-amide;
4-Ethyl-1H-indole-5-carboxylic acid (4,4-difluoro-1-hydroxy-cyclohexylmethyl)-amide;
7-Acetyl-4-chloro-1H-indole-5-carboxylic acid (4,4-difluoro-1-hydroxy-cyclohexylmethyl)-amide;
4-Chloro-7-(1-hydroxy-ethyl)-1H-indole-5-carboxylic acid (4,4-difluoro-1-hydroxy-cyclohexylmethyl)-amide;
4-Chloro-7-(1-hydroxy-1-methyl-ethyl)-1H-indole-5-carboxylic acid (4,4-difluoro-1-hydroxy-cyclohexylmethyl)-amide;
7-Methyl-4-trifluoromethyl-1H-indole-5-carboxylic acid (1-hydroxy-cyclohexylmethyl)-amide;
7-Methyl-4-trifluoromethyl-1H-indole-5-carboxylic acid (4,4-difluoro-1-hydroxy-cyclohexylmethyl)-amide;
4,7-Dimethyl-1H-indole-5-carboxylic acid (1-hydroxy-cyclohexylmethyl)-amide;
4-Chloro-7-ethyl-1H-indole-5-carboxylic acid (1-hydroxy-cyclohexylmethyl)-amide;
4-Chloro-7-ethyl-1H-indole-5-carboxylic acid (4,4-difluoro-1-hydroxy-cyclohexylmethyl)-amide;
7-Chloro-4-methyl-1H-indole-5-carboxylic acid (1-hydroxy-cyclohexylmethyl)-amide;
7-Chloro-4-methyl-1H-indole-5-carboxylic acid (4,4-difluoro-1-hydroxy-cyclohexylmethyl)-amide;
4-Chloro-7-methoxy-1H-indole-5-carboxylic acid (1-hydroxy-cyclohexylmethyl)-amide;
7-Methoxy-4-methyl-1H-indole-5-carboxylic acid (4,4-difluoro-1-hydroxy-cyclohexylmethyl)-amide;
7-Methoxy-4-methyl-1H-indole-5-carboxylic acid (1-hydroxy-cyclohexylmethyl)-amide;
4-Chloro-7-ethoxy-1H-indole-5-carboxylic acid (1-hydroxy-cyclohexylmethyl)-amide;
4-Chloro-7-hydroxy-1H-indole-5-carboxylic acid (4,4-difluoro-1-hydroxy-cyclohexylmethyl)-amide;
4-Chloro-7-ethoxy-1H-indole-5-carboxylic acid (4,4-difluoro-1-hydroxy-cyclohexylmethyl)-amide;
4-Chloro-7-propyl-1H-indole-5-carboxylic acid (1-hydroxy-cyclohexylmethyl)-amide;
4-Chloro-7-propyl-1H-indole-5-carboxylic acid (4,4-difluoro-1-hydroxy-cyclohexylmethyl)-amide;
7-(2-tert-Butoxy-ethoxy)-4-chloro-1H-indole-5-carboxylic acid (1-hydroxy-cyclohexylmethyl)-amide;
7-(2-tert-Butoxy-ethoxy)-4-chloro-1H-indole-5-carboxylic acid (4,4-difluoro-1-hydroxy-cyclohexylmethyl)-amide;
4-Chloro-7-(2-hydroxy-ethoxy)-1H-indole-5-carboxylic acid (1-hydroxy-cyclohexylmethyl)-amide;
4-Chloro-7-(2-hydroxy-ethoxy)-1H-indole-5-carboxylic acid (4,4-difluoro-1-hydroxy-cyclohexylmethyl)-amide;
7-Acetyl-4-chloro-1H-indole-5-carboxylic acid (1-hydroxy-cyclohexylmethyl)-amide;
4-Chloro-7-(1-hydroxy-1-methyl-ethyl)-1H-indole-5-carboxylic acid (1-hydroxy-cyclohexylmethyl)-amide;
4,7-Difluoro-1H-indole-5-carboxylic acid (1-hydroxy-cyclohexylmethyl)-amide;
4,7-Difluoro-1H-indole-5-carboxylic acid (4,4-difluoro-1-hydroxy-clohexylmethyl)-amide;
4-Fluoro-7-methoxy-1H-indole-5-carboxylic acid (1-hydroxy-cyclohexylmethyl)-amide;

4-Fluoro-7-methoxy-1H-indole-5-carboxylic acid (4,4-difluoro-1-hydroxy-cyclohexylmethyl)-amide;

4-Chloro-7-(2-ethoxy-ethyl)-1H-indole-5-carboxylic acid (4,4-difluoro-1-hydroxy-cyclohexylmethyl)-amide; and 4-Chloro-7-(1-methoxy-1-methyl-ethyl)-1H-indole-5-carboxylic acid (4,4-difluoro-1-hydroxy-cyclohexylmethyl)-amide;

or a salt of such a compound.

12. A pharmaceutical composition containing, as active principle, a compound of formula (I) according to claim 1 or a pharmaceutically acceptable salt thereof, and at least one therapeutically inert excipient.

13. A method for the treatment of a $P2X_7$-mediated disease selected from pain; neurodegenerative and neuroinflammatory diseases; bone and joint diseases; obstructive diseases of the airways; cardiovascular diseases; eye diseases; skin diseases; abdominal and gastrointestinal tract diseases; genitourinary diseases; cancer; auto-immune and allergic disorders selected from the group consisting of Hashimoto's thyroiditis, Graves' disease, Addison's disease, diabetes mellitus, idiopathic thrombocytopaenic purpura, eosinophilic fasciitis, hyper-IgE syndrome and antiphospholipid syndrome; and disorders with an inflammatory or immunological component selected from the group consisting of acquired immune deficiency syndrome (AIDS), leprosy, Sezary syndrome and paraneoplastic syndromes comprising administering to a subject a pharmaceutically active amount of the compound of formula (I) according to claim 1 or a pharmaceutically acceptable salt thereof.

14. A method for the treatment of a $P2X_7$-mediated disease selected from pain; neurodegenerative and neuroinflammatory diseases; bone and joint diseases; obstructive diseases of the airways; cardiovascular diseases; eye diseases; skin diseases; abdominal and gastrointestinal tract diseases; genitourinary diseases; cancer; auto-immune and allergic disorders selected from the group consisting of Hashimoto's thyroiditis, Graves' disease, Addison's disease, diabetes mellitus, idiopathic thrombocytopaenic purpura, eosinophilic fasciitis, hyper-IgE syndrome and antiphospholipid syndrome; and disorders with an inflammatory or immunological component selected from the group consisting of acquired immune deficiency syndrome (AIDS), leprosy, Sezary syndrome and paraneoplastic syndromes component comprising administering to a subject a pharmaceutically active amount of the compound of formula ($I_{HET}$) according to claim 10 or a pharmaceutically acceptable salt thereof.

* * * * *

UNITED STATES PATENT AND TRADEMARK OFFICE
CERTIFICATE OF CORRECTION

PATENT NO.         : 9,556,117 B2
APPLICATION NO.    : 14/653363
DATED              : January 31, 2017
INVENTOR(S)        : Kurt Hilpert et al.

Page 1 of 1

It is certified that error appears in the above-identified patent and that said Letters Patent is hereby corrected as shown below:

In the Claims

Column 114, Line 1-2, Claim 10, "$^{2S}$ represents hydrogen, (C1–C4)alkyl, (C1-C3)fluoroalkyl or halogen" should be "$R^{2S}$ represents hydrogen, (C1–C4)alkyl, (C1-C3)fluoroalkyl or halogen".

Signed and Sealed this
Sixteenth Day of May, 2017

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 35
<212> TYPE: DNA
<213> ORGANISM: Homo sapiens
<220> FEATURE:
<221> NAME/KEY: source
<222> LOCATION: 1..35
<223> OTHER INFORMATION: /mol_type="DNA"
      /organism="Homo sapiens"

<400> SEQUENCE: 1
atcgcggccg ctcagtaagg actcttgaag ccact                              35

<210> SEQ ID NO 2
<211> LENGTH: 38
<212> TYPE: DNA
<213> ORGANISM: Homo sapiens
<220> FEATURE:
<221> NAME/KEY: source
<222> LOCATION: 1..38
<223> OTHER INFORMATION: /mol_type="DNA"
      /organism="Homo sapiens"

<400> SEQUENCE: 2
cgccgctagc accaccatgc cggcctgctg cagctgca                           38
```